United States Patent
Barda et al.

(10) Patent No.: US 7,449,477 B2
(45) Date of Patent: Nov. 11, 2008

(54) 7-PHENYL-ISOQUINOLINE-5-SULFONYLAMINO DERIVATIVES AS INHIBITORS OF AKT (PROTEIN KINASE B)

(75) Inventors: David Anthony Barda, Indianapolis, IN (US); Kenneth James Henry, Jr., Carmel, IN (US); Jianping Huang, Carmel, IN (US); Sajan Joseph, Indianapolis, IN (US); Ho-Shen Lin, Indianapolis, IN (US); Michael Enrico Richett, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/595,798

(22) PCT Filed: Nov. 22, 2004

(86) PCT No.: PCT/US2004/037189

§ 371 (c)(1),
(2), (4) Date: May 12, 2006

(87) PCT Pub. No.: WO2005/054202

PCT Pub. Date: Jun. 16, 2005

(65) Prior Publication Data

US 2007/0037796 A1    Feb. 15, 2007

Related U.S. Application Data

(60) Provisional application No. 60/524,963, filed on Nov. 25, 2003.

(51) Int. Cl.
   *C07D 217/22*  (2006.01)
   *C07D 401/12*  (2006.01)
   *A61K 31/4725* (2006.01)
   *A61K 31/472*  (2006.01)

(52) U.S. Cl. .......... 514/307; 514/218; 514/227.8; 514/232.8; 514/253.05; 540/575; 544/60; 544/128; 544/363; 546/139; 546/148

(58) Field of Classification Search ........ 540/575; 544/60, 128, 363; 546/143, 148; 514/218, 514/227.8, 232.8, 253.05
See application file for complete search history.

(56) References Cited

U.S. PATENT DOCUMENTS

| 4,525,589 A | 6/1985 | Hidaka et al. |
| 4,678,783 A | 7/1987 | Hidaka et al. |
| 5,747,507 A | 5/1998 | Ikegaki et al. |

FOREIGN PATENT DOCUMENTS

| EP | 0 520 336    | 6/1992  |
| JP | 06 100540    | 4/1994  |
| WO | WO 01/64238  | 9/2001  |
| WO | WO 01/91754  | 12/2001 |
| WO | WO 02/50019  | 6/2002  |
| WO | WO 02/083064 | 10/2002 |
| WO | WO 2004/094386 | 11/2004 |
| WO | WO 2005/011697 | 2/2005  |

OTHER PUBLICATIONS

Reuveni, Hadas, et al., "Toward a PKB Inhibitor: Modification of a Selective PKA Inhibitor by Rational Design," Biochemistry, vol. 41, No. 32, pp. 10304-10314 (2002); XP002267237.

*Primary Examiner*—Zinna N Davis
(74) *Attorney, Agent, or Firm*—Danica Hostettler; Manisha A. Desai

(57) ABSTRACT

The present invention relates to compounds Formula (I) as inhibitors of AKT activity, which are useful for the treatment of susceptible neoplasms and viral infections.

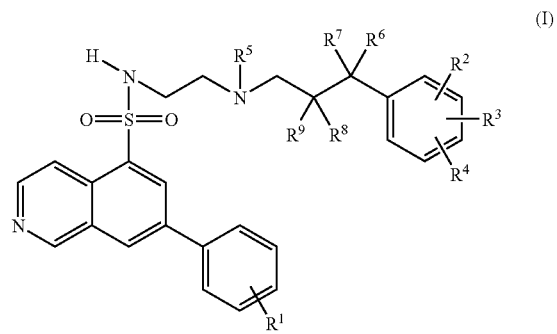

9 Claims, No Drawings

7-PHENYL-ISOQUINOLINE-5-SULFONYLAMINO DERIVATIVES AS INHIBITORS OF AKT (PROTEIN KINASE B)

This application is a U.S. National Phase Entry pursuant to 35 U.S.C. Section 371 for PCT/US2004/037189, filed Nov. 22, 2004, which claims the benefit of priority under 35 U.S.C. Section 119(e) of U.S. Provisional Patent Application No. 60/524,963, filed Nov. 25, 2003.

The present invention provides compounds of Formula (I), compositions thereof, and a method of inhibiting Protein Kinase B (Akt) that comprises administering to a patient in need thereof an effective amount of a compound of Formula (I). In addition, the present invention relates to processes for preparing the compounds of Formula (I) and intermediates thereof.

BACKGROUND OF THE INVENTION

Protein kinases are involved in the signal transduction pathways linking growth factors, hormones and other cell regulation molecules to cell growth, survival and metabolism under both normal and pathological conditions. One such protein kinase, protein kinase B (also known as Akt), is a serine/threonine kinase that plays a central role in promoting the proliferation and survival of a wide range of cell types, thereby protecting cells from apoptosis (programmed cell death) (Khwaja, *Nature* 33-34 (1990)). Three members of the Akt/PKB subfamily of second-messenger regulated serine/threonine protein kinases have been identified and are termed Akt1/PKBα, Akt2/PKBβ, and Akt3/PKBγ. A number of proteins involved in cell proliferation and survival have been described as substrates of Akt in cells. Two examples of such substrates include glycogen synthase kinase-3 (GSK3) and Forkhead transcription factors (FKs). See Brazil and Hemmings, *Trends in Biochemical Sciences* 26, 675-664.

A number of protein kinases and phosphatases regulate the activity of Akt. For instance, activation of Akt is mediated by phosphatidylinositol 3-kinase (PI3-K), which initiates the binding of second messenger phospholipids to the pleckstrin homology (PH) binding domain of Akt. The binding anchors Akt to plasma membrane and results in phosphorylation and activation of the enzyme. Amplifications of the catalytic subunit of PI3-K, p110α, or mutations in the PI3-K regulatory subunit, p85α, lead to activation of Akt in several types of human cancer. (Vivanco and Sawyers, *Nature Reviews in Cancer* (2002) 2: 489-501.

The tumor suppressor, PTEN, is a critical negative regulator of Akt activation by PI3-K. Myers et al. *Proc. Nat. Acad. Sci.* 95, *USA* (1998) 13513-13518. Inactivating mutations in the PTEN gene have been found at high frequencies in a large number of human tumors and tumor cell lines, including prostate cancer, breast cancer, ovarian cancer, glioblastoma, melanoma and other cancer types. Inactivation of the PTEN protein results in elevated levels of phosphorylated Akt and increased Akt activity in tumor cells. Li, et al., *Science* (1997) 275: 1943-1947; Guldberg, et al., *Cancer Research* (1997) 57: 3660-3663; Risinger, et al., *Cancer Research* (1997) 57: 4736-4738; Vivanco and Sawyers, *Nature Reviews in Cancer* (2002) 2: 489-501. In addition to overactivation of Akt due to defects in PTEN, direct amplication and/or overexpression of Akt2 and Akt3 have been found in human neoplasia, for example ovarian, pancreatic, prostate and breast cancer cells (Cheung et al., *Proc. Nat. Acad. Sci. USA* (1992) 89:9267-9271; Cheung et al., *Proc. Nat. Acad. Sci. USA* (1996) 93:3636-3641; Nakatani et al., J. Biol. Chem. (1999) 274: 21528-21532).

The critical role of Akt in cell proliferation and survival is further strengthened by studies showing that germline knockout of Akt1 results in partial embryonic lethality. The surviving littermates display stunted growth, increased organismal apoptosis, and early deaths. (Cho et al., *J. Biol. Chem.* (2001) 276: 38349-38520; Chen et al., *Genes Dev.* (2001) 15: 2203-2208). It has also been demonstrated that pharmacological inactivation of Akt induces apoptosis in cultured human ovarian cancer cells (Yuan et al., *Oncogene* 19, 2324-2340, 2000) and decreases growth of a human ovarian carcinoma xenograft in mice (Hu et al., *Clin. Cancer Res.* 6, 880-886, 2000).

Recent studies have also demonstrated the role of the PI3-K/AKT pathway in the life cycle of numerous viruses. Some viral proteins have been shown to directly activate the PI3-K/Akt pathway, thus providing an environment favorable for viral replication. These include the Tat protein of human immunodeficiency virus (HIV), Protein X of hepatitis B virus, and NS5A of hepatitis C virus (Borgatti et al., *Eur. J. Immunol.* (1997) 27: 2805-2811; Lee et al., *J. Biol. Chem.* (2001) 276: 16969-16977; He et al., *J. Virol.* (2002) 76: 9207-9217). The PI3-K/Akt pathway is also required for initiation and completion of the replication cycle of human cytomegalovirus (HCMV). In fact, pharmacological inactivation of this pathway results in abortive production of HCMV and survival of the host cells (Johnson et al., *J. Virol.* (2001) 75: 6022-6032).

Because of its pivotal role in the regulation of cell survival, Akt provides a novel therapeutic target for the effective treatment of various disorders, particularly cancer and viral infections. However, such treatment requires the development of potent, selective inhibitors of Akt. Thus, the present invention provides a class of novel inhibitors of Akt, compositions comprising these compounds, and methods of using the compounds.

BRIEF SUMMARY OF THE INVENTION

The present invention provides compounds of Formula (I):

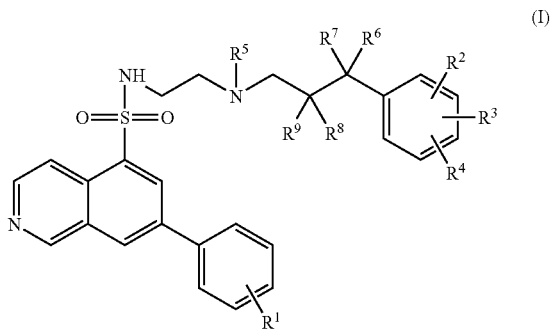

wherein $R^1$ is hydrogen, halogen, hydroxy, amino, —$CHF_2$, —$CF_3$, or —$NHSO_2CH_3$;

$R^2$, $R^3$, and $R^4$ are each independently selected from the group consisting of:

hydrogen;

halogen;

—($C_1$-$C_4$)alkyl;

—$CF_3$;

amino;

nitro;

—(CH$_2$)$_p$OR$^{10}$;
—(CH$_2$)$_n$CN;
—C(O)NR$^{11}$R$^{12}$
—C(O)OR$^{16}$;
—NHC(O)R$^{13}$;
—O(CH$_2$)$_o$Y;
—SCH$_3$;
—SO$_2$R$^{14}$;
N-morpholino;
N-piperazine or N-piperazine substituted with (C$_1$-C$_4$)alkyl;
N-pyrrolidine or N-pyrrolidine substituted with —(CH$_2$)$_p$OH;
N-1,1-dioxothiomorpholine;
N-[1,4]-diazepinyl;
phenyl or phenyl substituted with —CF$_3$, nitro, amino, halogen, hydroxy, (C$_1$-C$_4$) alkyl,
(C$_1$-C$_4$)alkoxy or —NHSO$_2$CH$_3$; and
piperidine or piperidine substituted on the nitrogen with —C(O)(C$_1$-C$_4$) alkyl;

or R$^2$ and R$^3$ may, together with the phenyl ring to which they are attached, form a naphthaline (benzo-fused ring) of the structure:

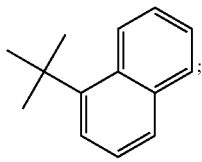

R$^5$, R$^6$ and R$^8$ are hydrogen;
R$^7$ and R$^9$ are each independently hydrogen or hydroxy;
R$^{10}$ is hydrogen, (C$_1$-C$_4$)alkyl, —(CF$_2$)$_t$CHF$_2$, —(CH$_2$)$_q$NR$^{17}$R$^{18}$, —(CH$_2$)$_q$O(C$_1$-C$_4$ alkyl), pyrrolidine, or phenyl; which pyrrolidine may be optionally substituted on the nitrogen with C$_1$-C$_4$ alkyl.
R$^{11}$ and R$^{12}$ are each independently hydrogen or (C$_1$-C$_4$) alkyl;
R$^{13}$ is (C$_1$-C$_4$)alkyl, cyclopropyl or —(CH$_2$)—OR$^{19}$;
R$^{14}$ is (C$_1$-C$_4$)alkyl, —NR$^{20}$R$^{21}$, N-pyrrolidine, phenyl, or —CF$_3$;
R$^{16}$, R$^{17}$, R$^{18}$, R$^{19}$, R$^{20}$, and R$^{21}$ are each independently hydrogen or C$_1$-C$_4$ alkyl;
m is 0, 1, 2, or 3;
n is 0 or 1;
o is 1, 2 or 3;
p is 0, 1 or 2;
q is 1, 2, or 3;
t is 0 or 1;
Y is morpholine, pyrrolidine, or pyrrolidine substituted on the nitrogen by (C$_1$-C$_4$)alkyl;

and the pharmaceutically acceptable salts thereof.

In another embodiment, the present invention provides compounds of Formula (I):

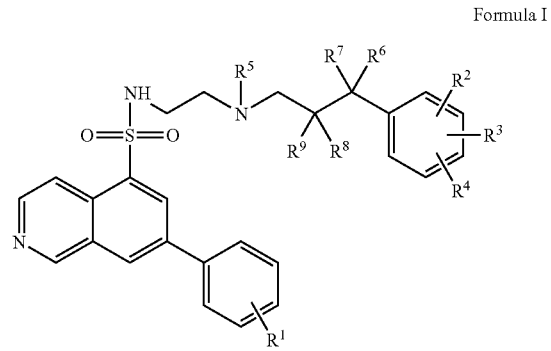

Formula I wherein R$^1$ is hydrogen, halogen, hydroxy, amino, —CHF$_2$ or —NHSO$_2$CH$_3$;
R$^2$, R$^3$, and R$^4$ are each independently:
hydrogen;
halogen;
—(C1-C4)alkyl;
—CF$_3$;
amino;
nitro;
—(CH$_2$)$_p$OR$^{10}$;
—(CH$_2$)$_n$CN;
—C(O)NR$^{11}$R$^{12}$;
—C(O)OR$^{11}$;
—NHC(O)R$^{13}$;
—O(CH$_2$)$_o$Y;
—SCH$_3$;
—SO$_2$R$^{14}$;
N-morpholino;
N-piperazine or N-piperazine substituted with (C1-C4)alkyl;
N-pyrrolidine or N-pyrrolidine substituted with —(CH$_2$)$_p$OH;
N-1,1-dioxothiomorpholine;
N-[1,4]-diazepinyl;
phenyl or phenyl substituted with —CF$_3$, nitro, amino, halogen, hydroxy, (C1-C4) alkyl, (C1-C4)alkoxy or —NHSO$_2$CH$_3$;
piperidine or piperidine substituted on the nitrogen with —C(O)(C1-C4) alkyl;

or wherein R$^2$ and R$^3$ may together with the phenyl ring of formula I form a naphthaline (benzo-fused ring) of the structure:

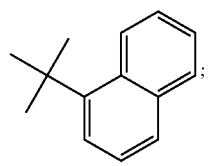

R$^5$, R$^6$ and R$^8$ are hydrogen;
R$^7$ and R$^9$ are each independently hydrogen or hydroxy;
R$^{10}$ is hydrogen, (C1-C4)alkyl, —(CF$_2$)$_n$CHF$_2$, —(CH$_2$)$_m$NR$^{11}$R$^{12}$, —(CH$_2$)$_o$O(C1-C4alkyl), or phenyl;

$R^{11}$ and $R^{12}$ are each independently hydrogen or (C1-C4)alkyl;
$R^{13}$ is (C1-C4)alkyl, cyclopropyl or —$(CH_2)_o R^{11}$;
$R^{14}$ is (C1-C4)alkyl, —$NR^1 R^{12}$, N-pyrrolidine, phenyl, or —$CF_3$;
m is 0, 1, 2, or 3;
n is 0 or 1;
o is 1, 2 or 3;
p is 0, 1 or 2;
Y is morpholine, pyrrolidine or pyrrolidine substituted on the nitrogen by (C1-C4)alkyl;

and the pharmaceutically acceptable salts thereof.

One preferred embodiment of the invention is compounds of Formula II:

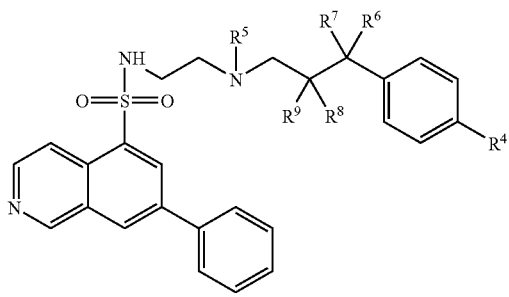

Formula II wherein $R^5$, $R^6$, $R^7$, $R^8$, $R^9$ are defined as above;
$R^4$ is halogen; nitro; cyano; —$CF_3$; —$(CH_2)_p OR^{10}$; or —$SO_2 R^{14}$;
p is 0;
$R^{10}$ is —$CHF_2$;
$R^{14}$ is $(C_1-C_4)$alkyl; —$CF_3$; or —$NR^{20}R^{21}$, and the pharmaceutically acceptable salts thereof.

A more preferred embodiment of the invention is a compound of Formula II as above, wherein $R^5$, $R^6$, $R^7$, $R^8$ and $R^9$ are as defined above and wherein $R^4$ is nitro;

and the pharmaceutically acceptable salts thereof.

Another preferred embodiment of the invention includes compounds of Formula III:

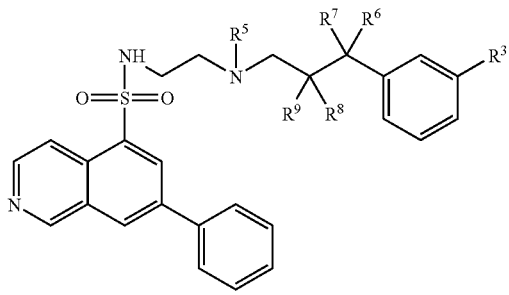

Formula III wherein $R^5$, $R^6$, $R^7$, $R^8$, and $R^9$ are defined as above;
$R^3$ is hydroxy;

and the pharmaceutically acceptable salts thereof.

Compounds of Formula (I) are inhibitors of Akt. Because these compounds inhibit the effects of Akt activation, the compounds are useful in the treatment of disorders related to Akt activity. Thus, compounds of Formula (I) are antiviral and antineoplastic agents.

The present compounds are believed to be useful in treating carcinomas such as neoplasms of the central nervous system: glioblastoma multiforme, astrocytoma, oligodendroglial tumors, ependymal and choroid plexus tumors, pineal tumors, neuronal tumors, medulloblastoma, schwannoma, meningioma, meningeal sarcoma; neoplasms of the eye: basal cell carcinoma, squamous cell carcinoma, melanoma, rhabdomyosarcoma, retinoblastoma; neoplasms of the endocrine glands: pituitary neoplasms, neoplasms of the thyroid, neoplasms of the adrenal cortex, neoplasms of the neuroendocrine system, neoplasms of the gastroenteropancreatic endocrine system, neoplasms of the gonads; neoplasms of the head and neck: head and neck cancer, oral cavity, pharynx, larynx, odontogenic tumors; neoplasms of the thorax: large cell lung carcinoma, small cell lung carcinoma, non-small cell lung carcinoma, neoplasms of the thorax, malignant mesothelioma, thymomas, primary germ cell tumors of the thorax; neoplasms of the alimentary canal: neoplasms of the esophagus, neoplasms of the stomach, neoplasms of the liver, neoplasms of the gallbladder, neoplasms of the exocrine pancreas, neoplasms of the small intestine, veriform appendix and peritoneum, adneocarcinoma of the colon and rectum, neoplasms of the anus; neoplasms of the genitourinary tract: renal cell carcinoma, neoplasms of the renal pelvis and ureter, neoplasms of the bladder, neoplasms of the urethra, neoplasms of the prostate, neoplasms of the penis, neoplasms of the testis; neoplasms of the female reproductive organs: neoplasms of the vulva and vagina, neoplasms of the cervix, adenocarcinoma of the uterine corpus, ovarian cancer, gynecologic sarcomas; neoplasms of the breast; neoplasms of the skin: basal cell carcinoma, squamous cell carcinoma, dermatofibrosarcoma, Merkel cell tumor; malignant melanoma; neoplasms of the bone and soft tissue: osteogenic sarcoma, malignant fibrous histiocytoma, chondrosarcoma, Ewing's sarcoma, primitive neuroectodermal tumor, angiosarcoma; neoplasms of the hematopoietic system: myelodysplastic sydromes, acute myeloid leukemia, chronic myeloid leukemia, acute lymphocytic leukemia, HTLV-1 and T-cell leukemia/lymphoma, chronic lymphocytic leukemia, hairy cell leukemia, Hodgkin's disease, non-Hodgkin's lymphomas, mast cell leukemia; and neoplasms of children: acute lymphoblastic leukemia, acute myelocytic leukemias, neuroblastoma, bone tumors, rhabdomyosarcoma, lymphomas, renal tumors.

Thus, in one embodiment, the present invention provides a method for the treatment of susceptible neoplasms comprising: administering to a patient in need thereof an effective amount of a compound of Formula (I), or a pharmaceutically acceptable salt thereof. That is, the present invention provides for the use of a compound of Formula (I), or a pharmaceutical composition thereof, for the treatment of susceptible neoplasms.

The present invention provides a compound of Formula (I), or a pharmaceutically acceptable salt thereof, for use in therapy.

The term "susceptible neoplasm", as defined herein, represents an abnormal growth of tissue in mammals capable of being treated by a compound of formula I.

In another aspect, the present invention provides for the use of a compound of Formula (I), or a pharmaceutically acceptable salt thereof, in the manufacture of a medicament for inhibiting Akt activity. Thus, the present invention provides for the use of a compound of Formula (I), or a pharmaceutically acceptable salt thereof, in the manufacture of a medicament for the treatment of susceptible neoplasms by means of the method described above.

The compounds of the present invention are particularly useful for the treatment of neoplasms that exhibit defects in PTEN, neoplasms with deregulated PI3-Kinase activity, or neoplasms that exhibit elevated Akt activity. Specifically, the compounds of Formula (I) are useful for the treatment of neuroblastoma, melanoma, breast cancer, prostate cancer, ovarian cancer, liver cancer, lung cancer, and cancers of the digestive tract, kidney, endometrium, or thyroid.

In particular, the present compounds are believed to be useful in treating solid tumors. Thus, the compounds of the present invention are useful for the treatment of prostate cancer, ovarian cancer, and breast cancer.

In a preferred embodiment, the present invention provides a method for treating prostate cancer comprising: administering to a patient in need thereof an effective amount of a compound of Formula (I), or a pharmaceutically acceptable salt thereof.

In another preferred embodiment, the present invention provides a method for treating ovarian cancer comprising: administering to a patient in need thereof an effective amount of a compound of Formula (I), or a pharmaceutically acceptable salt thereof.

In another preferred embodiment, the present invention provides a method for treating breast cancer comprising: administering to a patient in need thereof an effective amount of a compound of Formula (I), or a pharmaceutically acceptable salt thereof.

In another embodiment, the present invention provides a method for inhibiting Akt activity comprising: administering to a patient in need thereof an effective amount of a compound of Formula (I), or a pharmaceutically acceptable salt thereof.

In another embodiment, the present invention provides a method for the treatment of viral infections comprising: administering to a patient in need thereof an effective amount of a compound of Formula (I), or a pharmaceutically acceptable salt thereof. Thus, the present invention provides for the use of a compound of Formula (I), or a pharmaceutical composition thereof, as antiviral agents.

In a further embodiment, this invention provides a pharmaceutical composition comprising, as an active ingredient, a compound of Formula (I), or a pharmaceutically acceptable salt thereof, in combination with one or more pharmaceutically acceptable carriers, diluents, or excipients.

In another embodiment, the present invention relates to a method of making a compound represented by Formula (I), and intermediates thereof.

DETAILED DESCRIPTION OF THE INVENTION

The terms and abbreviations used in the preparations and examples have their normal meanings unless otherwise designated. For example "° C." refers to degrees Celsius; "N" refers to normal or normality; "mol" refers to mole or moles; "h" refers to hour(s); "eq" refers to equivalent; "g" refers to gram or grams; "L" refers to liter or liters; "M" refers to molar or molarity; "brine" refers to a saturated aqueous sodium chloride solution; "MS" refers to mass spectrometry; "NMR" refers to nuclear magnetic resonance spectroscopy; "TLC" refers to thin layer chromatography; "ACN" refers to acetonitrile; "DMF" refers to N,N-dimethylformamide; "DMSO" refers to dimethylsulfoxide; "Et$_2$O" refers to diethyl ether; "EtOAc" refers to ethyl acetate; "MeOH" refers to methanol; "EtOH" refers to ethanol; "iPrOH" refers to isopropanol; "TEA" refers to triethylamine; "TFA" refers to trifluoroacetic acid; "THF" refers to tetrahydrofuran; "DIBAL-H" refers to diisobutylaluminum hydride.

As used herein, the term "$C_1$-$C_4$ alkyl" refers to straight or branched, monovalent, saturated aliphatic chains of 1 to 4 carbon atoms and includes, but is not limited to, methyl, ethyl, propyl, isopropyl, butyl, isobutyl, sec-butyl, and tert-butyl. The terms "$C_1$-$C_3$ alkyl" and "$C_1$-$C_2$ alkyl" are encompassed within the definition of "$C_1$-$C_4$ alkyl."

"$C_2$-$C_4$ alkenyl" refers to a straight or branched hydrocarbon chain of 2 to 4 carbon atoms with at least one carbon-carbon double bond. Examples of $C_2$-$C_4$ alkenyl groups include, but are not limited to, ethenyl(vinyl), propen-1-yl, propen-2-yl (isoprenyl), propen-3-yl(allyl), 2-methyl-propen-3-yl, 2-buten-4-yl, 2-methyl-propen-1-yl, and 1-buten-1-yl.

"$C_1$-$C_4$ alkoxy" represents a $C_1$-$C_4$ alkyl group, as defined above, linked to the parent molecule through an oxygen atom. Typical $C_1$-$C_4$ alkoxy groups include methoxy, ethoxy, propoxy, isopropoxy, butoxy, sec-butoxy, tert-butoxy, and the like. The term "$C_1$-$C_4$ alkoxy" includes within its definition the term "$C_1$-$C_3$ alkoxy" and "$C_1$-$C_2$ alkoxy."

"$C_1$-$C_4$ alkoxycarbonyl" represents a straight or branched $C_1$-$C_4$ alkoxy chain, as defined above, that is attached via the oxygen atom of the alkoxy to a carbonyl moiety. Typical $C_1$-$C_4$ alkoxycarbonyl groups include methoxycarbonyl, ethoxycarbonyl, propoxycarbonyl, isopropoxycarbonyl, butoxycarbonyl, t-butoxycarbonyl and the like. The term "$C_1$-$C_4$ alkoxycarbonyl" is equivalent to the term "Carbo-($C_1$-$C_4$) alkoxy."

"$C_3$-$C_6$ cycloalkyl" represents a saturated hydrocarbon ring structure containing from three to six carbon atoms. Typical $C_3$-$C_6$ cycloalkyl groups include cyclopropyl, cyclopentyl, cyclohexyl, and the like.

"Aryl" refers to an unsaturated aromatic carbocyclic group of 6 to 14 carbon atoms having a single ring (e.g., phenyl) or multiple condensed (fused) rings (e.g., naphthyl or anthryl).

"Halo," "halogen," and "halide" represent a chloro, fluoro, bromo or iodo atom. Preferred halogens include chloro and fluoro.

As used herein, a "benzo-fused ring" refers to a bicyclic ring in which $R^2$ and $R^3$ form a ring that is ortho-fused to the phenyl ring to which they are attached. It will be understood that when $R^2$ and $R^3$ form a benzo-fused ring, $R^4$ may be a substituent on any position of the bicyclic ring that allows substitution. Preferred benzo-fused rings of the present invention include naphthalene, benzofuran, and benzodioxole.

The skilled artisan will recognize that when $R^2$, $R^3$, or $R^4$ are N-[1,4]-diazepinyl, the substituent is the following:

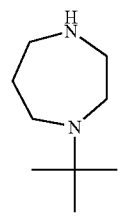

The term "Pg" refers to an alcohol, carboxyl, or amino protecting group. Typical protecting groups include tetrahydropyranyl (THP), silanes such as trimethylsilane (TMS), tert-butyldimethylsilane (TBDMS), and tert-butyldiphenylsilane (TBDPS), methoxymethyl (MOM), benzyl (Bn), p-methoxybenzyl, formyl, acetyl (Ac), and tert-butoxycarbonyl (t-BOC). Typical carboxyl protecting groups may include methyl, ethyl, and tert-butyl. The selection and use of protecting groups is well known and appreciated in the art. See for example, *Protecting Groups in Organic Synthesis*, Theodora Greene (Wiley-Interscience); *Protecting Groups*, Philip J. Kocienski, Thieme Medical Publishers, inc: New York 1994, chapters 2, 4, 6.

This invention includes the pharmaceutically acceptable salts of the compounds of Formula (I). A compound of this invention can possess a sufficiently basic functional group, which can react with any of a number of inorganic and organic acids, to form a pharmaceutically acceptable salt.

The term "pharmaceutically-acceptable salt" as used herein, refers to a salt of a compound of the above Formula (I). It should be recognized that the particular counterion forming a part of any salt of this invention is usually not of a critical nature, so long as the salt as a whole is pharmacologically acceptable and as long as the counterion does not contribute undesired qualities to the salt as a whole.

The compounds of Formula (I) and the intermediates described herein form pharmaceutically-acceptable acid addition salts with a wide variety of organic and inorganic acids, and include the physiologically-acceptable salts which are often used in pharmaceutical-chemistry. Such salts are also part of this invention. A pharmaceutically-acceptable acid addition salt is formed from a pharmaceutically-acceptable acid, as is well known in the art. Such salts include the pharmaceutically acceptable salts listed in *Journal of Pharmaceutical Science*, 66:2-19 (1977), which are known to the skilled artisan. See also, The Handbook of Pharmaceutical Salts; Properties, Selection, and Use. P. H. Stahl and C. G. Wermuth (ED.s), Verlag, Zurich (Switzerland) 2002.

Typical inorganic acids used to form such salts include hydrochloric, hydrobromic, hydriodic, nitric, sulfuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkanedioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, p-toluenesulfonate, xylenesulfonate, tartarate, and the like. Preferred salts of the compounds of Formula (I) include hydrochloride salts and mesylate salts.

As used herein, the term "patient" refers to a mammal that is afflicted with one or more disorders associated with Akt activity. It will be understood that the most preferred patient is a human. It is also understood that this invention relates specifically to the inhibition of mammalian Akt/PKB.

It is recognized that one skilled in the art may affect the disorders associated with Akt activity by treating a patient presently afflicted with the disorders with an effective amount of the compound of Formula (I). Thus, the terms "treatment" and "treating" are intended to refer to all processes wherein there may be a slowing, interrupting, arresting, controlling, or stopping of the progression of the disorders described herein, but does not necessarily indicate a total elimination of all symptoms.

As used herein, the term "effective amount" of a compound of Formula (I) refers to an amount that is effective in treating the disorders described herein.

Additional preferred embodiments of the compounds of the current invention include the following.

(a) $R^1$ is hydrogen;
(b) $R^1$ is hydroxy;
(c) $R^1$ is amino;
(d) $R^1$ is halogen;
(e) $R^2$ is hydrogen;
(f) $R^2$ is $C_1$-$C_4$ alkyl;
(g) $R^2$ is phenyl;
(h) $R^3$ is hydrogen;
(i) $R^3$ is hydroxy;
(j) $R^4$ is halogen;
(k) $R^4$ is nitro;
(l) $R^7$ is hydrogen;
(m) $R^7$ is hydroxy;
(n) $R^9$ is hydrogen;
(o) $R^9$ is hydroxy.

The skilled artisan will appreciate that additional preferred embodiments may be selected by combining the preferred embodiments above, or by reference to the examples given herein.

Compounds Exemplified in the Application Include the Following

It will be understood that the reference number preceding each compound name corresponds to the example wherein the compound is exemplified.

1) 7-Phenyl-isoquinoline-5-sulfonic acid [2-(3-naphthalen-1-yl-propylamino)-ethyl]-amide, dihydrochloride salt;
2) 7-Phenyl-isoquinoline-5-sulfonic acid {2-[3-(4-trifluoromethyl-phenyl)-propylamino]-ethyl}-amide, dihydrochloride salt;
3) 7-Phenyl-isoquinoline-5-sulfonic acid {2-[3-(4-nitrophenyl)-propylamino]-ethyl}-amide, dihydrochloride salt;
4) 7-Phenyl-isoquinoline-5-sulfonic acid {2-[3-(4-bromophenyl)-propylamino]-ethyl}-amide, dihydrochloride salt;
5) 7-Phenyl-isoquinoline-5-sulfonic acid {2-[3-(3-cyanomethylphenyl)-propylamino]-ethyl}-amide, dihydrochloride salt;
6) 7-Phenyl-isoquinoline-5-sulfonic acid {2-[3-(2-methoxycarbonylphenyl)-propylamino]-ethyl}-amide, dihydrochloride salt;
7) 7-Phenyl-isoquinoline-5-sulfonic acid {2-[3-(2-[1,4]diazepin-1-yl-phenyl)-propylamino]-ethyl}-amide, tetrahydrochloride salt;
8) 7-Phenyl-isoquinoline-5-sulfonic acid [2-(3-biphenyl-2-yl-propylamino)-ethyl]-amide, dihydrochloride salt;
9) 7-Phenyl-isoquinoline-5-sulfonic acid {2-[3-(2-phenoxyphenyl)-propylamino]-ethyl}-amide, dihydrochloride salt;
10) 7-Phenyl-isoquinoline-5-sulfonic acid {2-[3-(2-(N-morpholinyl)phenyl)-propylamino]-ethyl}-amide, tetrahydrochloride salt;

11) 7-Phenyl-isoquinoline-5-sulfonic acid {2-[3-(2-(piperazin-1-yl-phenyl)-propylamino]-ethyl}-amide, tetrahydrochloride salt;
12) 7-Phenyl-isoquinoline-5-sulfonic acid {2-[3-(2-isopropylphenyl)-propylamino]-ethyl}-amide, dihydrochloride salt;
13) 7-Phenyl-isoquinolirne-5-sulfonic acid {2-[3-(2-cyanophenyl)-propylamino]-ethyl}-amide, dihydrochloride salt;
14) 7-Phenyl-isoquinoline-5-sulfonic acid {2-[3-(2-phenylsulfonyl-phenyl)-propylamino]-ethyl}-amide, dihydrochloride salt;
15) 7-Phenyl-isoquinoline-5-sulfonic acid {2-[3-(2-(N-piperidinyl)-phenyl)-propylamino]-ethyl}-amide, trihydrochloride salt;
16) 7-Phenyl-isoquinoline-5-sulfonic acid {2-[3-(2-propylphenyl)-propylamino]-ethyl}-amide, dihydrochloride salt;
17) 7-Phenyl-isoquinoline-5-sulfonic acid {2-[3-(2-(2-hydroxyethyl)-phenyl)-propylamino]-ethyl}-amide, dihydrochloride salt;
18) 7-Phenyl-isoquinoline-5-sulfonic acid {2-[3-(3-hydroxyphenyl)-propylamino]-ethyl}-amide, dihydrochloride salt;
19) 7-Phenyl-isoquinoline-5-sulfonic acid {2-[3-(4-hydroxyphenyl)-propylamino]-ethyl}-amide, dihydrochloride salt;
20) 7-Phenyl-isoquinoline-5-sulfonic acid {2-[3-(4-(N,N-dimethyl-aminocarbonyl)phenyl)-propylamino]-ethyl}-amide, dihydrochloride salt;
21) 7-Phenyl-isoquinoline-5-sulfonic acid {2-[3-(4-(N-propylamino-sulfonyl)phenyl)-propylamino]-ethyl}-amide, dihydrochloride salt;
22) 7-Phenyl-isoquinoline-5-sulfonic acid {2-[3-(2-hydroxyphenyl)-propylamino]-ethyl}-amide, dihydrochloride salt;
23) 7-Phenyl-isoquinoline-5-sulfonic acid {2-[3-(4-(N-propylamino-carbonyl)phenyl)-propylamino]-ethyl}-amide, dihydrochloride salt;
24) 7-Phenyl-isoquinoline-5-sulfonic acid {2-[3-(4-(N,N-dimethyl-aminosulfonyl)phenyl)-propyl-amino]-ethyl}-amide, dihydrochloride salt;
25) 7-Phenyl-isoquinoline-5-sulfonic acid {2-[3-(4-(cyclopropyl-carbonylamino)phenyl)-propylamino]-ethyl}-amide, dihydrochloride salt;
26) 7-Phenyl-isoquinoline-5-sulfonic acid {2-[3-(4-(propionylamino)-phenyl)-propylamino]-ethyl}-amide, dihydrochloride salt;
27) 7-Phenyl-isoquinoline-5-sulfonic acid {2-[3-(4-(1,1,2,2-tetrafluoroethoxy)phenyl)-propylamino]-ethyl}-amide, dihydrochloride salt;
28) 7-Phenyl-isoquinoline-5-sulfonic acid {2-[3-(4-acetamidophenyl)-propylamino]-ethyl}-amide, dihydrochloride salt;
29) 7-Phenyl-isoquinoline-5-sulfonic acid {2-[3-(4-aminocarbonyl-phenyl)-propylamino]-ethyl}-amide, dihydrochloride salt;
30) 7-Phenyl-isoquinoline-5-sulfonic acid {2-[3-(4-difluoromethoxy-phenyl)-propylamino]-ethyl}-amide, dihydrochloride salt;
31) 7-Phenyl-isoquinoline-5-sulfonic acid {2-[3-(3-methoxyphenyl)-propylamino]-ethyl}-amide, dihydrochloride salt;
32) 7-Phenyl-isoquinoline-5-sulfonic acid {2-[3-(3-cyanophenyl)-propylamino]-ethyl}-amide, dihydrochloride salt;
33) 7-Phenyl-isoquinoline-5-sulfonic acid {2-[3-(4-cyanophenyl)-propylamino]-ethyl}-amide, dihydrochloride salt;
34) 2-Methoxy-N-(4-{3-[2-(7-phenyl-isoquinoline-5-sulfonylamino)-ethylamino]-propyl}-phenyl)-acetamide, dihydrochloride salt;
35) 7-Phenyl-isoquinoline-5-sulfonic acid {2-[3-(4-methylthiophenyl)-propylamino]-ethyl}-amide, dihydrochloride salt;
36) 7-Phenyl-isoquinoline-5-sulfonic acid {2-[3-(5-fluoro-biphenyl-2-yl)-propylamino]-ethyl}-amide, dihydrochloride salt;
37) 7-Phenyl-isoquinoline-5-sulfonic acid {2-[3-(2,4-bis-trifluoro-methylphenyl)-propylamino]-ethyl}-amide, dihydrochloride salt;
38) 7-Phenyl-isoquinoline-5-sulfonic acid {2-[3-(2-chloro-4-nitrophenyl)-propylamino]-ethyl}-amide, dihydrochloride salt;
39) 7-Phenyl-isoquinoline-5-sulfonic acid {2-[3-(2-methyl-5-nitrophenyl)-propylamino]-ethyl}-amide, dihydrochloride salt;
40) 7-Phenyl-isoquinoline-5-sulfonic acid {2-[3-(2-methyl-4-nitrophenyl)-propylamino]-ethyl}-amide, dihydrochloride salt;
41) 7-Phenyl-isoquinoline-5-sulfonic acid {2-[3-(6-chloro-biphenyl-3-yl)-propylamino]-ethyl}-amide, dihydrochloride salt;
42) 7-Phenyl-isoquinoline-5-sulfonic acid {2-[3-(5-nitro-biphenyl-2-yl)-propylamino]-ethyl}-amide, dihydrochloride salt;
43) 7-Phenyl-isoquinoline-5-sulfonic acid {2-[3-(5-trifluoromethyl-biphenyl-2-yl)-propylamino]-ethyl}-amide, dihydrochloride salt;
44) 7-Phenyl-isoquinoline-5-sulfonic acid {2-[3-(4-chloro-2-piperazin-1-yl-phenyl)-propylamino]-ethyl}-amide, tetrahydrochloride salt;
45) 7-Phenyl-isoquinoline-5-sulfonic acid {2-[3-(5-chloro-3'-trifluoromethyl-biphenyl-2-yl)-propylamino]-ethyl}-amide, dihydrochloride salt;
46) 7-Phenyl-isoquinoline-5-sulfonic acid {2-[3-(5-chloro-biphenyl-2-yl)-propylamino]-ethyl}-amide, dihydrochloride salt;
47) 7-Phenyl-isoquinoline-5-sulfonic acid {2-[3-(5-chloro-3'-nitro-biphenyl-2-yl)-propylamino]-ethyl}-amide, dihydrochloride salt;
48) 7-Phenyl-isoquinoline-5-sulfonic acid {2-[3-(4-chloro-2-fluoro-phenyl)-propylamino]-ethyl}-amide, dihydrochloride salt;
49) 7-Phenyl-isoquinoline-5-sulfonic acid {2-[3-(4-chloro-2-(4-methyl-piperazin-1-yl)-phenyl)-propylamino]-ethyl}-amide, tetrahydrochloride salt;
50) 7-Phenyl-isoquinoline-5-sulfonic acid {2-[3-(4-chloro-2-(N-pyrrolidinyl)-phenyl)-propylamino]-ethyl}-amide, trihydrochloride salt;
51) 7-Phenyl-isoquinoline-5-sulfonic acid {2-[3-(4-chloro-2-(N-morpholino)-phenyl)-propylamino]-ethyl}-amide, trihydrochloride salt;
52) 7-Phenyl-isoquinoline-5-sulfonic acid {2-[3-(4-chloro-2-(1,1-dioxo-thiomorpholin-4-yl)-phenyl)-propylamino]-ethyl}-amide, trihydrochloride salt;
53) 7-Phenyl-isoquinoline-5-sulfonic acid {2-[3-(4-chloro-2-(piperidin-4-yl)-phenyl)-propylamino]-ethyl}-amide, trihydrochloride salt;
54) 7-Phenyl-isoquinoline-5-sulfonic acid {2-[3-(4-chloro-2-(3-methyl-piperazin-1-yl)-phenyl)-propylamino]-ethyl}-amide, tetrahydrochloride salt;

55) 7-Phenyl-isoquinoline-5-sulfonic acid {2-[3-(4-chloro-2-(1-methyl-pyrrolidin-3-yl)oxy-phenyl)-propylamino]-ethyl}-amide, trihydrochloride salt;
56) 7-Phenyl-isoquinoline-5-sulfonic acid {2-[3-(4-chloro-2-(pyrrolidin-3-yl)oxy-phenyl)-propylamino]-ethyl}-amide, trihydrochloride salt;
57) 7-Phenyl-isoquinoline-5-sulfonic acid {2-[3-(2-(1-acetyl-piperidin-4-yl)-4-chloro-phenyl)-propylamino]-ethyl}-amide, dihydrochloride salt;
58) 7-Phenyl-isoquinoline-5-sulfonic acid {2-[3-(2-(2-hydroxy-ethyl)-4-nitro-phenyl)-propylamino]-ethyl}-amide, dihydrochloride salt;
59) 7-Phenyl-isoquinoline-5-sulfonic acid {2-[3-(4-chloro-2-(2-dimethylamino-ethoxy)-phenyl)-propylamino]-ethyl}-amide, dihydrochloride salt;
61) 7-Phenyl-isoquinoline-5-sulfonic acid {2-[3-(4-nitro-2-trifluoromethylphenyl)-propylamino]-ethyl}-amide, dihydrochloride salt;
62) 7-Phenyl-isoquinoline-5-sulfonic acid {2-[3-(2-methoxycarbonyl-4-nitrophenyl)-propylamino]-ethyl}-amide, dihydrochloride salt;
63) 7-Phenyl-isoquinoline-5-sulfonic acid {2-[3-(2-methoxy-4-nitrophenyl)-propylamino]-ethyl}-amide, dihydrochloride salt;
64) 7-Phenyl-isoquinoline-5-sulfonic acid {2-[3-(2-carboxy-4-nitrophenyl)-propylamino]-ethyl}-amide, dihydrochloride salt;
65) 7-Phenyl-isoquinoline-5-sulfonic acid {2-[3-(2,4-dichlorophenyl)-propylamino]-ethyl}-amide, dihydrochloride salt;
66) 7-Phenyl-isoquinoline-5-sulfonic acid {2-[3-(2,3-dichlorophenyl)-propylamino]-ethyl}-amide, dihydrochloride salt;
67) 7-Phenyl-isoquinoline-5-sulfonic acid {2-[3-(4-cyano-3-trifluoromethylphenyl)-propylamino]-ethyl}-amide, dihydrochloride salt;
68) 7-Phenyl-isoquinoline-5-sulfonic acid {2-[3-(2,3-difluorophenyl)-propylamino]-ethyl}-amide, dihydrochloride salt;
69) 7-Phenyl-isoquinoline-5-sulfonic acid (2-{3-[4-chloro-2-(morpholino-4-yl-ethoxy)-phenyl]-propylamino}-ethyl)-amide, dihydrochloride salt;
70) 7-Phenyl-isoquinoline-5-sulfonic acid {2-[3-(2,4-difluorophenyl)-propylamino]-ethyl}-amide, dihydrochloride salt;
71) 7-Phenyl-isoquinoline-5-sulfonic acid {2-[3-(4-(N-pyrrolidinesulfonyl)-phenyl)-propylamino]-ethyl}-amide, hydrochloride salt;
72) 7-Phenyl-isoquinoline-5-sulfonic acid [2-(3-(4-aminophenyl)-propylamino)-ethyl]-amide, dihydrochloride salt;
73) 7-Phenyl-isoquinoline-5-sulfonic acid [2-(3-hydroxy-3-(4-nitrophenyl)-propylamino)-ethyl]-amide, dihydrochloride salt;
74) 7-Phenyl-isoquinoline-5-sulfonic acid [2-(3-hydroxy-3-(4-fluorophenyl)-propylamino)-ethyl]-amide;
75) 7-Phenyl-isoquinoline-5-sulfonic acid [2-(3-hydroxy-3-(4-cyanophenyl)-propylamino)-ethyl]-amide, dihydrochloride salt;
76) 7-Phenyl-isoquinoline-5-sulfonic acid [2-(3-hydroxy-3-phenyl-propylamino)-ethyl]-amide;
77) 7-Phenyl-isoquinoline-5-sulfonic acid [2-(3-hydroxy-3-(3-nitrophenyl)-propylamino)-ethyl]-amide, dihydrochloride salt;
78) (R)-7-Phenyl-isoquinoline-5-sulfonic acid [2-(3-hydroxy-3-phenyl-propylamino)-ethyl]-amide, dihydrochloride salt;
79) 7-Phenyl-isoquinoline-5-sulfonic acid [2-(3-hydroxy-3-(4-methanesulfonyl-phenyl)-propylamino)-ethyl]-amide, dihydrochloride salt;
80) 7-Phenyl-isoquinoline-5-sulfonic acid [2-(3-hydroxy-3-(4-trifluoromethanesulfonyl-phenyl)-propylamino)-ethyl]-amide, dihydrochloride salt;
81) (R)-7-Phenyl-isoquinoline-5-sulfonic acid [2-(3-hydroxy-3-(4-nitrophenyl)-propylamino)-ethyl]-amide, mesylate salt;
82) (S)-7-Phenyl-isoquinoline-5-sulfonic acid [2-(3-hydroxy-3-(4-nitrophenyl)-propylamino)-ethyl]-amide, mesylate salt;
83) 7-Phenyl-isoquinoline-5-sulfonic acid [2-(2-hydroxy-3-(4-nitrophenyl)-propylamino)-ethyl]-amide, dihydrochloride salt;
84) 7-Phenyl-isoquinoline-5-sulfonic acid [2-(2-hydroxy-3-phenyl-propylamino)-ethyl]-amide, dihydrochloride salt;
85) 7-Phenyl-isoquinoline-5-sulfonic acid [2-(2-hydroxy-3-(4-nitrophenyl)-propylamino)-ethyl]-amide isomer 1, dihydrochloride salt;
86) 7-Phenyl-isoquinoline-5-sulfonic acid [2-(2-hydroxy-3-(4-nitrophenyl)-propylamino)-ethyl]-amide isomer 2, dihydrochloride salt;
87) 7-Phenyl-isoquinoline-5-sulfonic acid [2-(2,3-dihydroxy-3-(4-nitrophenyl)-propylamino)-ethyl]-amide, dihydrochloride salt;
88) 7-Phenyl-isoquinoline-5-sulfonic acid [2-(2,3-dihydroxy-3-(4-nitrophenyl)-propylamino)-ethyl]-amide isomer 1, dihydrochloride salt;
89) 7-Phenyl-isoquinoline-5-sulfonic acid [2-(2,3-dihydroxy-3-(4-nitrophenyl)-propylamino)-ethyl]-amide isomer 2, dihydrochloride salt;
90) 7-(4-aminophenyl)-isoquinoline-5-sulfonic acid [2-(3-(4-nitrophenyl)-propylamino)-ethyl]-amide, trihydrochloride salt;
91) 7-(2-hydroxy-phenyl)-isoquinoline-5-sulfonic acid {2-[3-(4-nitro-phenyl)-propylamino]-ethyl}-amide, dihydrochloride salt;
92) 7-(3-aminophenyl)-isoquinoline-5-sulfonic acid [2-(3-(4-nitrophenyl)-propylamino)-ethyl]-amide, trihydrochloride salt;
93) 7-(3-fluorophenyl)-isoquinoline-5-sulfonic acid [2-(3-(4-nitrophenyl)-propylamino)-ethyl]-amide;
94) 7-(3-methanesulfonylamino-phenyl)-isoquinoline-5-sulfonic acid {2-[3-(4-nitro-phenyl)-propylamino]-ethyl}-amide, dihydrochloride salt;
95) 7-(3-Amino-phenyl)-isoquinoline-5-sulfonic acid {2-[3-(5-chloro-3'-nitro-biphenyl-2-yl)-propylamino]-ethyl}-amide, trihydrochloride salt;
96) 7-(4-methanesulfonylaminophenyl)-isoquinoline-5-sulfonic acid {2-[3-(4-nitro-phenyl)-propylamino]-ethyl}-amide, dihydrochloride salt;
97) 7-(3-Difluoromethylphenyl)-isoquinoline-5-sulfonic acid {2-[3-(4-nitro-phenyl)-propylamino]-ethyl}-amide, dihydrochloride salt;
98) 7-(4-hydroxy-phenyl)-isoquinoline-5-sulfonic acid {2-[3-(4-nitro-phenyl)-propylamino]-ethyl}-amide, dihydrochloride salt;
99) 7-(3-hydroxy-phenyl)-isoquinoline-5-sulfonic acid {2-[3-(4-nitro-phenyl)-propylamino]-ethyl}-amide, dihydrochloride salt;
100) 7-Phenyl-isoquinoline-5-sulfonic acid {2-[3-(4-methanesulfonyl-phenyl)-propylamino]-ethyl}-amide, dihydrochloride salt;

101) 7-Phenyl-isoquinoline-5-sulfonic acid {2-[3-(3-nitro-phenyl)-propylamino]-ethyl}-amide, dihydrochloride salt;
102) 7-Phenyl-isoquinoline-5-sulfonic acid {2-[3-(4-trifluoromethanesulfonyl-phenyl)-propylamino]-ethyl}-amide, dihydrochloride salt;
103) 7-Phenyl-isoquinoline-5-sulfonic acid {2-[3-(2-ethyl-4-nitro-phenyl)-propylamino]-ethyl}-amide, dihydrochloride salt;
104) 7-Phenyl-isoquinoline-5-sulfonic acid {2-[3-(4-cyano-2-methyl-phenyl)-propylamino]-ethyl}-amide, dihydrochloride salt;
105) 7-Phenyl-isoquinoline-5-sulfonic acid {2-[3-(3-hydroxy-4-nitro-phenyl)-propylamino]-ethyl}-amide, dihydrochloride salt;
106) 7-Phenyl-isoquinoline-5-sulfonic acid {2-[3-(4-cyano-3-hydroxy-phenyl)-propylamino]-ethyl}-amide, bis-trifluoroacetate salt;
107) 7-(3-Hydroxy-phenyl)-isoquinoline-5-sulfonic acid {2-[3-(3-hydroxy-phenyl)-propylamino]-ethyl}-amide;
108) 7-(4-Hydroxy-phenyl)-isoquinoline-5-sulfonic acid {2-[3-(2-fluoro-4-methoxy-phenyl)-propylamino]-ethyl}-amide;
109) 7-(4-Hydroxy-phenyl)-isoquinoline-5-sulfonic acid {2-[3-(3-hydroxy-phenyl)-propylamino]-ethyl}-amide;
110) 7-(3-Hydroxy-phenyl)-isoquinoline-5-sulfonic acid {2-[3-(2-fluoro-4-methoxy-phenyl)-propylamino]-ethyl}-amide;
111) 7-Phenyl-isoquinoline-5-sulfonic acid {2-[3-(4-cyano-phenyl)-2-hydroxy-propylamino]-ethyl}-amide, dihydrochloride salt, dihydrochloride salt;
112) 7-Phenyl-isoquinoline-5-sulfonic acid {2-[3-(4-cyano-phenyl)-2,3-dihydroxy-propylamino]-ethyl}-amide, dihydrochloride salt;
113) 7-Phenyl-isoquinoline-5-sulfonic acid {2-[2,3-dihydroxy-3-(4-trifluoromethanesulfonyl-phenyl)-propylamino]-ethyl}-amide, dihydrochloride salt.
114) 7-Phenyl-isoquinoline-5-sulfonic acid {2-[3-(4-nitro-phenyl)-propylamino]-ethyl}-amide, dihydrochloride
115) 7-Phenyl-isoquinoline-5-sulfonic acid {2-[3-(4-nitro-phenyl)-propylamino]-ethyl}-amide, dimesylate.

The compounds exemplified above are merely representative of the invention and are not limiting in any fashion.

The skilled artisan will appreciate that additional preferred embodiments may be selected by combining the preferred embodiments above, or by reference to the examples given herein.

The compounds of the present invention can be prepared by a variety of procedures, some of which are illustrated in the schemes and examples below. The schemes and examples should in no way be understood to be limiting in any way as to how the compounds may be made.

The skilled artisan will appreciate that the introduction of certain substituents will create asymmetry in the compounds of Formula (I). The present invention contemplates all stereoisomers, enantiomers, and mixtures of enantiomers, including racemates and diastereomers. It is preferred that the compounds of the invention containing chiral centers are single enantiomers.

It will be recognized by one of skill in the art that the individual steps in the following schemes may be varied to provide the compounds of Formula (I). The particular order of steps required to produce the compounds of Formula (I) is dependent upon the particular compound being synthesized, the starting compound, and the relative lability of the substituted moieties.

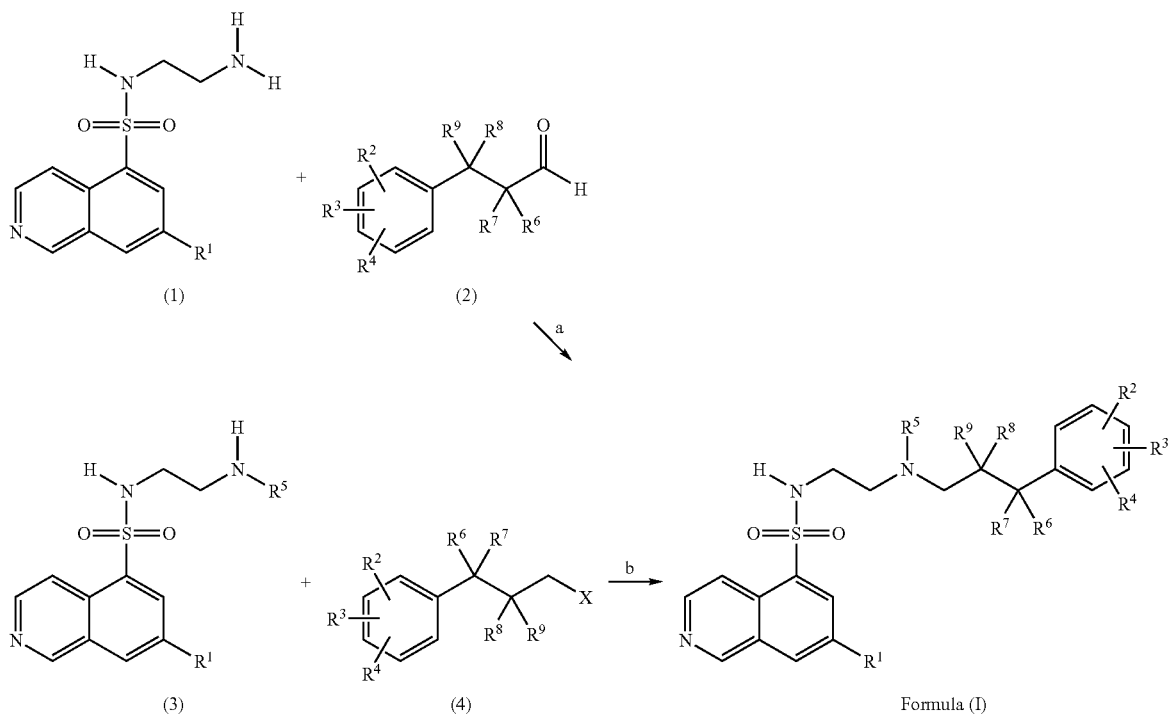

Scheme 1

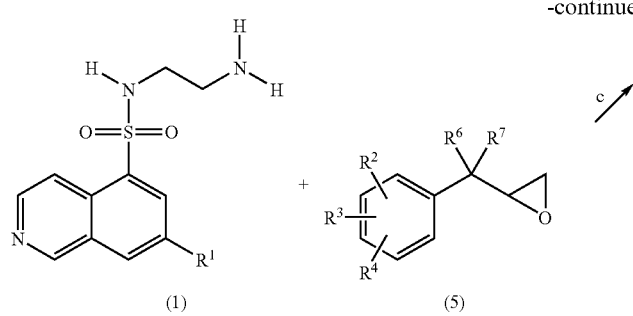

As depicted in Scheme 1, step a, a two-step procedure is used to give compounds of Formula (I) in which $R^5$ through $R^9$ are hydrogen. The compound of Formula (2) is added to a stirred solution of an organic base, such as triethylamine, and the compound of Formula (1) in anhydrous methylsulfoxide (DMSO) and dichloroethane (DCE), followed by stirring for 6 hours, or until the reaction is complete, to form imines in situ. Without isolation, the imines are reduced to the corresponding desired amines by sodium triacetoxyborohydride. The product of Formula (I) can be isolated and purified by techniques well known in the art, such as precipitation, filtration, extraction, evaporation, trituration, chromatography, or recrystallization.

The skilled artisan will recognize that when $R^6$ and $R^8$ are hydrogen, and $R^7$ and $R^9$ are combined to represent an olefin, the structures of Formula (2) would be cinnamaldehyde derivatives, and the result of performing step a on such a compound would be an allylic amine of Formula (I). This compound could be further elaborated (e.g. by dihydroxylation) to provide compounds of Formula (I) wherein $R^7$ and $R^9$ would both be hydroxyl.

Alternatively, as shown in Scheme 1, step b, a compound of Formula (3) in which $R^5$ is hydrogen or a suitable protecting group such as benzyl or trityl (See for example, *Protecting Groups in Organic Synthesis*, Theodora Greene, Wiley-Interscience); is coupled with a compound of Formula (4), where X is a suitable leaving group such as halogen or alkylsulfonate or arylsulfonate, in the presence of an appropriate base, such as diisopropyl ethyl amine, and subsequently deprotected by methods well known to the skilled artisan to give compounds of Formula (I). The skilled artisan will appreciate that compounds of Formula (4) may be prepared by following known literature procedures, or by methods described below.

Alternatively, as shown in Scheme 1, step c, a compound of Formula (1) is coupled with a compound of formula (5), with heating in an appropriate solvent, to give compounds of Formula (I) where $R^9$ is hydroxyl.

Scheme 2

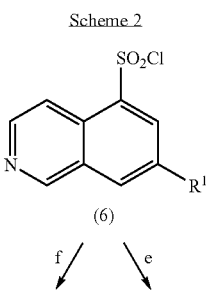

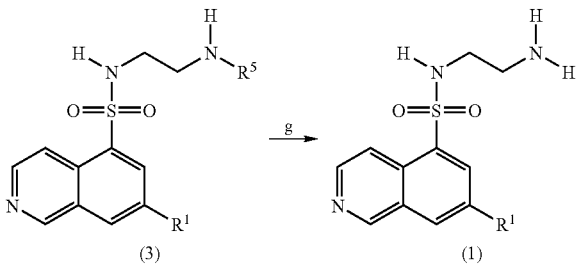

The compounds of Formula (1) may be made directly from the isoquinoline of Formula (6), as shown in Scheme 2, step e. The isoquinoline of Formula (6) is added in small portions to a stirred solution of ethylenediamine in a solvent such as $CH_2Cl_2$, THF, 1,4-dioxane, or preferably, $CHCl_3$. The mixture is filtered, dried, and chromatographed by methods well known to the skilled artisan to give the compound of Formula (1).

Alternatively, the compound of Formula (6) may be added to a solution of (2-amino-ethyl)-carbamic acid tert-butyl ester or other suitably monoprotected derivative of ethylenediamine in the presence of TEA or N,N-diisopropylethylamoine in anhydrous $CH_2Cl_2$ under $N_2$. The mixture is stirred at 0° C. to ambient temperature for about 4-24 hours. The mixture is filtered, dried, and chromatographed by methods well known to the skilled artisan to give the compound of Formula (3).

The compound of Formula (3) is de-protected by methods well known to the skilled artisan, as depicted in Step g.

It will be recognized that if $R^1$ is bromo or other suitable leaving group, then Suzuki coupling methodology, or alternative methods known to the skilled artisan, may be used to transform the substitutent to defined $R^1$ groups such as phenyl or substituted phenyl.

Scheme 3

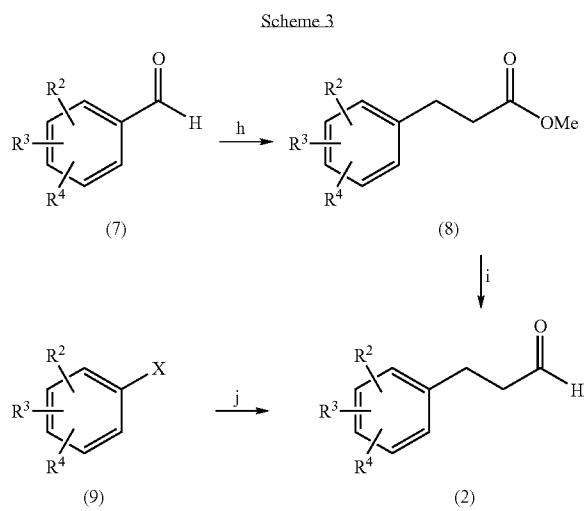

Compounds of Formula (2) may be prepared by a variety of routes, as depicted in Scheme 3. A brief description of two such routes is given below.

In step h, a suitable aryl aldehyde is added to a Horner-Wadsworth-Emmons reagent followed by reduction of the resulting olefin to give compounds of Formula (8). In step i, DIBAL-H is added dropwise to a solution of the compound of Formula (8) in a solvent, preferably $CH_2Cl_2$ at −78° C. under an inert atmosphere. The solution is stirred, followed by addition of methanol and diethyl ether. The cold bath is removed, and a HCl solution is added in small portions. The organic layer is separated, dried, filtered and concentrated to give the compound of Formula (2).

Alternatively, as shown in step j, a suitable aryl halide (compound (9), in which X is a halide) is coupled to allyl alcohol in the presence of $NaHCO_3$, palladium acetate, and tetrabutylammonium bromide, according to established literature precedence (Taylor, Gillespie and Patel, *Journal of Organic Chemistry*, (1992) 57, 3218-3225) in a solvent such as DMF at a temperature between 80° C. and 140° C. The product is extracted, purified and isolated by methods well known in the art.

The skilled artisan will recognize that when $R^4$ is a suitable leaving group, such as bromo, chloro, fluoro, or iodo, the substituent may be transformed to other $R^4$ groups, such as phenyl, isoxazolyl, furyl, or thienyl by Suzuki coupling methodology or other methods known to one skilled in the art, or to alkoxy or alkylamine by nucleophilic aromatic substitution methodology.

PREPARATIONS

General Preparation of Aryl Propionaldehyde Derivatives

Purge a mixture of aryl iodide (1.62 mmol), allyl alcohol (0.166 mL, 2.44 mmol), sodium bicarbonate (0.34 g, 4.06 mmol), tetrabutylammonium chloride (0.45 g, 1.62 mmol) and palladium acetate (18 mg, 0.081 mmol) in 5 mL anhydrous DMF with nitrogen and heat at 40° C. for 16 h. Cool the mixture to room temperature and dissolve in $Et_2O$. Wash the organic layer several times with water and brine, dry over $MgSO_4$, filter, and concentrate. Purify the product by flash chromatography on silica gel using hex/EtOAc as eluent to give the desired aldehyde.

The following compounds may be prepared using this general procedure or other well-known procedures described in Scheme 3.

| Preparation | R | Example |
|---|---|---|
| 1 | naphth-1-yl | 1 |
| 2 | 4-trifluoromethylphenyl | 2 |
| 3 | 4-nitrophenyl | 3 |
| 4 | 4-bromophenyl | 4 |
| 5 | 3-cyanomethylphenyl | 5 |
| 6 | 2-carboxymethylphenyl | 6 |
| 7 | Biphenyl-2-yl | 8 |
| 8 | 2-phenoxyphenyl | 9 |
| 9 | 2-isopropylphenyl | 12 |
| 10 | 2-cyanophenyl | 13 |
| 11 | 2-phenylsulfonylphenyl | 14 |
| 12 | 2-propylphenyl | 16 |
| 13 | 3-hydroxyphenyl | 19 |
| 14 | 4-(N,N-dimethylcarboxamido)phenyl | 21 |
| 15 | 4-(N-propylsulfonamido)phenyl | 22 |
| 16 | 2-hydroxyphenyl | 23 |
| 17 | 4-(N-propylcarboxamido)phenyl | 24 |
| 18 | 4-(N,N-dimethylsulfonamido)phenyl | 25 |
| 19 | 4-aminophenyl cyclopropanecarboxylic acid amide | 26 |
| 20 | 4-aminophenyl propionic acid amide | 27 |
| 21 | 4-(1,1,2,2-tetrafluoroethoxy)phenyl | 28 |
| 22 | 4-acetamidophenyl | 29 |
| 23 | 4-carboxamidophenyl | 30 |
| 24 | 4-difluoromethoxyphenyl | 31 |
| 25 | 3-methoxyphenyl | 32 |
| 26 | 3-cyanophenyl | 33 |
| 27 | 4-cyanophenyl | 34 |
| 28 | 4-N-(2-methoxyacetamido)phenyl | 35 |
| 29 | 4-methylsulfanylphenyl | 36 |
| 30 | 2,4-bistrifluoromethylphenyl | 38 |
| 31 | 2-chloro-4-nitrophenyl | 39 |
| 32 | 2-methyl-5-nitrophenyl | 40 |
| 33 | 2-methyl-4-nitrophenyl | 41 |
| 34 | 6-chloro-biphenyl-3-yl | 42 |
| 35 | 4-chloro-2-fluorophenyl | 49 |
| 36 | 4-nitro-2-trifluoromethylphenyl | 62 |
| 37 | 2-carbomethoxyl-4-nitrophenyl | 63 |
| 38 | 2-methoxy-4-nitrophenyl | 64 |
| 39 | 2-carboxy-4-nitrophenyl | 65 |
| 40 | 2,4-dichlorophenyl | 66 |
| 41 | 2,3-dichlorphenyl | 67 |
| 42 | 4-cyano-3-trifluoromethylphenyl | 68 |
| 43 | 2,3-difluorophenyl | 69 |
| 44 | 2,4-difluorophenyl | 71 |
| 45 | 4-(pyrrolidine-1-sulfonyl)-phenyl | 72 |
| 46 | 4-(tetrahydro-pyran-2-yloxy)-phenyl | 20 |
| 47 | 2-(2-(tetrahydro-pyran-2-yloxy)-ethyl)phenyl | 18 |
| 48 | 2-(2-(tetrahydro-pyran-2-yloxy)-ethyl)-4-nitro-phenyl | 59 |

Preparation 49

3-(4-chloro-2-pyrrolidin-1-yl-phenyl)propionaldehyde

Add pyrrolidine (0.97 g, 13.67 mmol) to a solution of 4-chloro-2-fluoro-1-nitrobenzene (2 g, 11.40 mmol) in 8 mL anhydrous DMSO under $N_2$. Stir the reaction mixture at 80° C. for 1 h. Cool the mixture, pour into ice-$H_2O$ and extract with $Et_2O$ (3×30 mL). Wash the organic phase with water and brine, dry over $MgSO_4$, filter, and concentrate. Chromatograph the residue on silica gel using hex/EtOAc 9:1 as eluent to afford 2.29 g (89%) of 1-(5-chloro-2-nitro-phenyl)-pyrrolidine as a yellow solid. Add tin chloride (10 g, 44.15 mmol)

to a solution of 1-(5-chloro-2-nitrophenyl)pyrrolidine (2 g, 8.83 mmol) in 25 mL of EtOH under nitrogen. Heat the reaction mixture at 70° C. for 3 h. After cooling, pour the mixture into ice-water, basify (pH=9) with NH₄OH, and extract with EtOAc (3×100 mL). Dry the organic phase over MgSO₄, concentrate, and purify the residue by silica gel chromatography using hex/EtOAc 8:2 as eluent to obtain 1.56 g (88%) of 1-(2-amino-5-chlorophenyl)pyrrolidine as an oil.

Add a solution of 0.58 g (8.45 mmol) of sodium nitrite in 3 mL of water to a mixture of the aniline (1.66 g, 8.45 mmol), 19 mL of water and 5 mL of concentrated sulfuric acid cooled at 5° C. in an ice bath, while maintaining the temperature below 10° C. Stir the mixture for 30 min and pour the solution into a solution of 1.75 g (10.56 mmol) of potassium iodide in 10 mL of water. Heat the aqueous solution at 60° C. for 3 h. Cool the black solution and add chloroform. Separate the organic layer and wash with 10% sodium hydroxide, 1M sodium thiosulfate, 10% hydrochloric acid, water, saturated sodium bicarbonate and brine. Dry the organic layer over MgSO₄, filter, concentrate the solvent under reduced pressure and chromatograph the residue using Hex/EtOAc 98:2 to provide 1-(5-chloro-2-iodo-phenyl)-pyrrolidine (60% yield). From this material, prepare the title compound using a procedure similar to Preparation 1.

Scheme 4

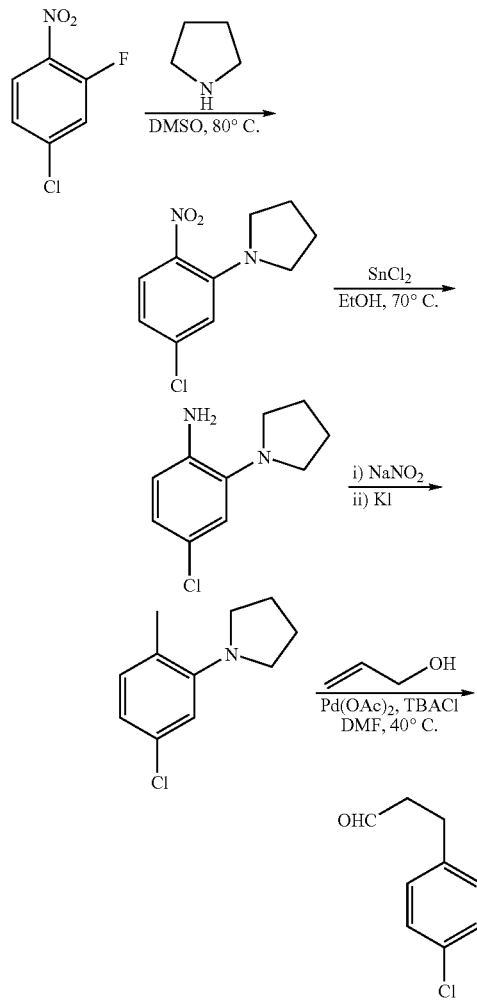

Using a procedure similar to preparation 49 (depicted in Scheme 4), with the appropriate starting materials, the following compounds may be prepared:

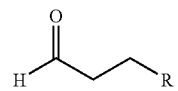

| Preparation | R | Example |
|---|---|---|
| 50 | 4-chloro-2-(4-methyl-piperazin-1-yl)-phenyl | 49 |
| 51 | 2-[1,4]diazepin-1-yl-phenyl | 7 |
| 52 | 2-(N-morpholinyl)phenyl | 10 |
| 53 | 2-piperazin-1-yl-phenyl | 11 |
| 54 | 2-N-piperidinylphenyl | 15 |
| 55 | 4-chloro-2-piperazin-1-ylphenyl | 44 |
| 56 | 4-chloro-2-morpholin-4-ylphenyl | 51 |
| 57 | 4-chloro-2-(1,1-dioxo-thiomorpholin-4-yl)-phenyl | 52 |
| 58 | 4-chloro-2-(3-methyl-piperazin-1-yl)-phenyl | 54 |

Preparation 60

3-[5-Chloro-2-(3-oxopropyl)-phenoxy]-pyrrolidine-1-carboxylic acid tert butyl ester Slowly add di-tert-butyl dicarbonate (5.5 g 25.29 mmol) to a solution of 3-hydroxypyrrolidine (2 g, 23 mmol) and triethylamine (6.45 mL, 45.98 mmol) in 30 mL of anhydrous dichloromethane under nitrogen at 0° C. Stirr the reaction mixture at ambient temperature for 16 h. After dilution with CH₂Cl₂, wash the organics with dilute acetic acid, saturated NaHCO₃ and water. Dry over MgSO₄, filter and concentrate to afford the carbamate as an orange solid (4.18 g, 97%).

To a stirred solution of 4-chloro-2-fluoro-1-nitrobenzene (2 g, 11.40 mmol) and 3-hydroxypyrrolidine-1-carboxylic acid tert-butyl ester in 40 mL of anhydrous DMF, add NaH (0.55 g, 22.79 mmol) at 0° C. in portions. Stir the mixture at room temperature for 1 h, then, pour into ice-water, extract with EtOAc (3×50 mL), dry over MgSO₄ and evaporate to afford the compound pure enough to use in the following step without further purification (yellow solid, 4.15 g). Follow a procedure similar to preparation 49 substituting 3-(5-chloro-2-nitro-phenoxy)-pyrrolidine-1-carboxylic acid tert butyl ester for 1-(5-chloro-2-nitro-phenyl)-pyrrolidine to prepare the title compound.

Following a procedure similar to preparation 60 using the appropriate starting materials affords the following compounds:

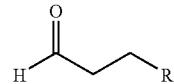

| Preparation # | Compound | Example # |
|---|---|---|
| 59 | 4-chloro-2-(1-methyl-pyrrolidin-3-yloxy)-phenyl | 55 |
| 61 | 4-chloro-2-(2-dimethylamino-ethoxy)-phenyl | 59 |
| 63 | 4-chloro-2-(2-morpholin-4-yl-ethoxy)-phenyl | 69 |

Preparation 69

3-(5-chloro-3'-nitro-biphenyl-2-yl)-propionaldehyde

Heat a mixture of 2-bromo-4-chloro-phenylamine (8.24 g, 40 mmol), 3-nitrophenylboronic acid (10.0 g, 60 mmol), Pd(PPh$_3$)$_4$ (2.8 g) and Na$_2$CO$_3$ (17.0 g) in toluene (200.0 mL), EtOH (30.0 mL) and water (80.0 mL) to 80° C. (oil bath) with stirring overnight. Cool to room temperature, dilute the mixture with EtOAc, filter and concentrate. Dissolve the residue in EtOAc, wash with brine and dry over Na$_2$SO$_4$. Chromatograph the crude material on silica (gradient 25% EtOAc in hexane) to give 5.27 g of the desired product as a yellowish crystal.

To a solution of amine (5.27 g, 21.19) in CH$_2$I$_2$ (22.7 mL), add isopentyl nitrite (7.5 g, 63.57 mmol) at room temperature. Stir the mixture for 2 hours, and then heat to 80° C. for one hour. After cooling to room temperature, add piperidine (56.8 mL) and CH$_3$CN (56.8 mL). Stir for one hour and then concentrate. Wash the residue with 10% HCl, and purify via silica gel with hexane to afford 7.0 g of 5-chloro-2-iodo-3'-nitro-biphenyl. From this material, prepare the title compound using a procedure similar to Preparation 1.

Using a procedure similar to preparation 69 with the appropriate starting materials the following compounds may be prepared:

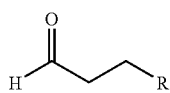

| Preparation | R | Example |
|---|---|---|
| 64 | 5-fluoro-biphenyl-2-yl | 36 |
| 65 | 5-nitro-biphenyl-2-yl | 42 |
| 66 | 5-trifluoromethyl-biphenyl-2-yl | 43 |
| 67 | 5-chloro-3'-trifluoromethyl-biphenyl-2-yl | 45 |
| 68 | 5-chloro-biphenyl-2-yl | 46 |

Preparation 70

4-[5-cloro-2-(3-oxo-propyl)-phenyl]-piperidine-1-carboxylic acid tert-butyl ester Stir a mixture of 2-bromo-4-chloro-phenylamine (1.2 g, 5.81 mmol), 4-(4,4,5,5-tetramethyl-[1,3,2]dioxaborolan-2-yl)-3,6-dihydro-2H-pyridine-1-carboxylic acid tert-butyl ester (1.98 g, 6.39 mmol), potassium carbonate (2.41 g, 17.4 mmol) and PdCl$_2$dppf ([1,1'-bis(diphenylphosphino)ferrocene]dichloropalladium(II)) (280 mg, 0.35 mmol) in 35 mL of DMF under argon atmosphere at 80° C. overnight. Cool to room temperature, and add Et$_2$O. Wash the mixture twice with water, dry over MgSO$_4$ and concentrate to afford the crude product.

Stir a solution of crude 4-(2-amino-5-chloro-phenyl)-3,6-dihydro-2H-pyridine-1-carboxylic acid tert-butyl ester (1.9 g, 6.15 mmol) and (Ph$_3$P)$_3$RhCl (560 mg, 0.61 mmol) in 20 mL of toluene at 60° C. overnight while bubbling H$_2$ into the solution. Filter the mixture through diatomaceous earth and evaporate the solvent. Chromatograph the crude product on silica gel, using hexane/EtOAc 2:1 as eluent, to afford purified material (57% yield, 2 steps).

Following a procedure similar to preparation 49 substituting 4-(5-cloro-2-nitro-phenyl)-piperidine-1-carboxylic acid tert-butyl ester for 1-(5-chloro-2-nitro-phenyl)-pyrrolidine gives the title compound.

Preparation 71

3-[2-(1-acetyl-piperidin-4-yl)-4-chloro-phenyl]-propionaldehyde

Add a 4N HCl dioxane solution (604 μL, 2.42 mmol) to a solution of 4-(5-chloro -2-iodo-phenyl)-piperidine-1-carboxylic acid tert-butyl ester (prepared according to preparation 70, 170 mg, 0.40 mmol) in CH$_2$Cl$_2$ (6 mL) at room temperature under argon, and stir the mixture overnight. Add triethylamine (450 μL, 3.20 mmol), DMAP (catalytic amount) and acetyl chloride (56 μL, 0.80 mmol), and stir the mixture overnight. Quench the reaction by addition of Et$_2$O, wash with 1N NaOH and water, dry over MgSO$_4$ and concentrate to afford 1-[4-(5-chloro-2-iodo-phenyl)-piperidin-1-yl]-ethanone. Purify the crude product by flash chromatography on silica gel, eluent hexane/EtOAc 3:2 (65% yield). Follow a procedure similar to preparation 49 substituting 1-[4-(5-chloro-2-iodo-phenyl)-piperidin-1-yl]-ethanone for 1-(5-chloro-2-iodo-phenyl)-pyrrolidine to obtain the title compound.

Preparation 72

7-Phenyl-isoquinoline-5-sulfonic acid (2-{[bis-(4-methoxy-phenyl)-methyl]-amino}-ethyl)-amide Add gaseous HCl to a solution of 4,4'-dimethoxybenzhydrol (10.3 g, 42 mmol) in ether (120 mL) until saturated, seal tightly and stir at room temperature for 45 minutes. Remove volatiles under reduced pressure, redissolve in ether, treat with anhydrous magnesium sulfate, filter and remove volatiles under reduced pressure to afford bis-4-methoxyphenyl-methyl chloride. Dissolve the dark red solid in THF (100 mL), and add the solution dropwise to neat ethylenediamine (56 mL, 84 mmol) over 20 minutes. Stir 30 minutes at room temperature and remove volatiles under reduced pressure. Partition the residue between brine (200 mL) and ether (200 mL). Wash the brine with two additional volumes of ether, then wash the combined ether solutions with two small portions of brine. Dry the organic solution with anhydrous sodium sulfate, decant and evaporate to afford N-[Bis-(4-methoxy-phenyl)-methyl]-ethane-1,2-diamine as a straw-colored oil in quantitative yield. $^1$H NMR (CDCl$_3$): δ 7.31 (d, J=8.4 Hz, 4H), 6.85 (d, J=8.4 Hz, 4H), 4.77 (s, 1H), 3.80 (s, 6H), 2.82 (t, J=5.5 Hz, 2H), 2.66 (t, J=5.5 Hz, 2H).
ESIMS: m/z 287 (M+H)$^+$.

Add 7-bromoisoquinoline-5-sulfonylchloride (428 mg, 1.39 mmol) to a solution of N-[Bis-(4-methoxy-phenyl)-methyl]-ethane-1,2-diamine (0.55 g, 2.09 mmol) and diisopropylethylamine (0.487 mL, 2.79 mmol) in dichloroethane (5.0 mL). After 30 minutes, partition the reaction between dichloromethane and water, and apply the organic phase to a silica gel cartridge (40 g). Elute the product from the silica gel with a continuous gradient from dichloromethane to 20% dichloromethane, and evaporate the appropriate fractions to afford the title compound (0.79 g, 98%). $^1$H NMR (DMSO): δ 9.46 (s, 1H), 8.77 (d, J=1.3 Hz, 1H), 8.74(d, J=6.2 Hz, 1H), 8.41 (d, J=6.2 Hz, 1H), 8.34 (d, J=1.8 Hz, 1H), 7.05 (t of d J1=1.7 Hz, J2=8.3 Hz, 4H), 6.76(t of d J1=1.7 Hz, J2=8.8 Hz, 4H), 4.44 (s, 1H), 3.71 (s, 6H), 2.99(t, J=6.1 Hz, 2H), 2.32 (t, J=5.9 Hz, 2H). LCMS: m/z 558 (M+H)$^+$, 556(M−H).

Add tetrakis(triphenylphosphine)palladium (0.816 g, 0.706 mmol) to a degassed mixture of phenylboronic acid (0.1.72 g, 14.1 mmol), cesium carbonate (9.20 g, 3.5928.2 mmol), and 7-bromo-isoquinoline-5-sulfonic acid (2-{[bis-(4-methoxy-phenyl)-methyl]-amino}-ethyl)-amide (3.93 g, 7.06 mmol) in toluene (75.0 mL) and water (100.0 mL). Warm to 100° C. for 2 hours, and cool to room temperature. Dilute with toluene (100 mL), separate layers, wash sequentially with water and brine, then dry with anhydrous MgSO$_4$, filter and evaporate. Apply the residue to a cation exchange cartridge, wash the cartridge with methanol, and then elute with 2M methanolic ammonia. Evaporation affords the title compound (2.25 g, 58%). $^1$H NMR (DMSO): δ9.56 (s, 1H), 8.78(d, J=1.8 Hz, 1H), 8.70(d, J=6.2 Hz, 1H), 8.75(d, J=2.0 Hz, 1H), 8.45 (d, J=6.2 Hz, 1H), 7.91(d of t J1=1.3 Hz, J=7.0 Hz, 2H), 7.62(t of t, J1=1.7 Hz, J2=7.4 Hz, 2H), 7.53 (t of t, J1=1.3 Hz, J2=7.4 Hz, 1H), 7.04 (d of t, J1=1.7 Hz, J2=8.8 Hz, 4H), 6.72 (d of t, J1=1.7 Hz, J2=8.8 Hz, 4H), 4.44 (s, 1H), 3.68(s, 6H), 3.01 (t, J=6.1 Hz, 2H), 2.35 (t, J=5.9 Hz, 2H). LCMS: m/z 554 (M+H)$^+$, 552(M−H).

Preparation 73

1-(4-nitrophenyl)propenone

Add tetrakis(triphenylphosphine)palladium (2.9 mg, 0.0025 mmol) to a solution of 4-nitrobenzoyl chloride (0.464 g, 2.5 mmol) and tributylvinyltin (0.767 mL, 2.62 mmol) in chloroform (3 mL), and warm the solution to 65° C. until precipitation of palladium black signals reaction completion. Cool the reaction, dilute with diethyl ether, wash with water, then shake with half saturated potassium fluoride. After standing 15 minutes, filter through diatomaceous earth, and wash again with half saturated potassium fluoride, then brine. Dry with anhydrous magnesium sulfate, filter and evaporate. Purify the residue by silica gel chromatography eluting with a gradient from hexanes to 1:1 hexanes:ethyl acetate to afford the title compound (246 mg, 55%). (Used in Example 73)

Using a method similar to Preparation 73, the following compounds may be prepared and isolated:

| Prep. # | Compound | Example |
|---|---|---|
| 74 | 1-(4-cyanophenyl)propenone | 75 |
| 75 | 1-(4-fluorophenyl)propenone | 74 |
| 76 | 1-phenylpropenone | 76 |
| 77 | 1-(3-nitrophenyl)propenone | 77 |
| 78 | 1-(4-methanesulfonylphenyl)propenone | To prep 82 |
| 79 | 1-(4-trifluoromethanesulfonylphenyl)propenone | To prep 83 |

Preparation 80

1-(R)-3-iodo-1-(4-nitro-phenyl)-propan-1-ol

Add 4M hydrochloric acid-dioxane (0.59 mL, 2.37 mmol) to a solution of 1-(4-nitrophenyl)propenone (0.4 g, 2.26 mmol) in dioxane (5 mL), stir 2 hours at room temperature, and evaporate under reduced pressure to afford crude chloroketone (0.43 g, 90%). Add this material (0.3 g, 1.4 mmol) to a solution of (+)-DIP-Chloride™ ((+)-B-Chlorodiisopinocampheylborane)(0.495 g, 0.154 mmol) in THF (1.1 mL) at −30° C. Allow to stand for 16 hours at −35° C. Evaporate under reduced pressure and replace the solvent with ether (5 mL). Add diethanolamine (0.3 mL, 0.3 mmol) and stir vigorously. Filter through diatomaceous earth and evaporate. Purify the residue by silica gel chromatography using a ethyl acetate-hexanes gradient to afford chloro alcohol (0.22 g, 74%, >95% ee). Add sodium iodide (0.7 g, 4.65 mmol) to a solution of the chloro alcohol (0.20 mg, 0.93 mmol) in acetone (3 mL) and heat to reflux for 15 hours. Cool, filter and evaporate the reaction, then redissolve the residue in ether, filter and evaporate to afford the title compound as a brown oil. $^1$H NMR (CDCl$_3$): δ8.26 (d, J=8.8 Hz, 2H), 7.60 (d, J=8.4 Hz, 2H), 5.04-5.01 (m, 1H), 3.48-3.37 (m, 1H), 3.29-3.24 (m, 1H), 2.26-2.20 (m, 2H). (Used in example 81)

Using a method similar to Preparation 80, substituting (−)-DIP-Chloride™ for (+)-DIP-Chloride™, or substituting sodium borohydride in methanol at room temperature for (+)-DIP-Chloride™ in THF the following compounds may be prepared and isolated:

| Prep. # | Compound | Example # |
|---|---|---|
| 81 | 1-(S)-3-Iodo-1-(4-nitro-phenyl)-propan-1-ol | 82 |
| 82 | 3-Iodo-1-(4-methanesulfonyl-phenyl)-propan-1-ol | 79 |
| 83 | 3-Iodo-1-(4-trifluoromethanesulfonyl-phenyl)-propan-1-ol | 80 |

Preparation 84

2-(4-Nitro-benzyl)-oxirane

Add allyl tri-n-butylstannane (30.10 mmol, 9.33 ml) dropwise to a stirred solution of 4-iodo-nitrobenzene (5 g, 20.07 mmol), tetrakis-(triphenylphosphine) palladium(0) (1.16 g, 1 mmol) and copper (I) iodide (306 mg, 1.6 mmol) in 50 ml of dry 1,4-dioxane under argon atmosphere. Reflux the mixture for 24 hours and then cool to room temperature. Dilute the solution with 40 ml of diethyl ether and add 20 ml of saturated solution of KF and stir for 2 hours. Filter the mixture and wash the organic layer with water (20 ml), brine (20 ml) and dry over sodium sulfate. Evaporate the solution under reduced pressure and purify the residue by flash chromatography on silica gel using hexane-ethyl acetate as eluent (20:1) to afford 1.80 g (55%) of 1-allyl-4-nitrobenzene. Add a solution of 3-chloro-peroxybenzoic acid (5.98 g, 24.28 mmol), in 20 ml of dichloromethane to a solution of 1-allyl-4-nitro-benzene (1.8 g, 11.04 mmol) in 50 ml of dichloromethane and stir the mixture at room temperature overnight. Quench with saturated NaHCO$_3$ (15 ml), and wash the organic layer three times with saturated NaHCO$_3$ and dry over magnesium sulfate. Evaporate under reduced pressure to afford 1.4 g (71%) of the title compound.

Scheme 5
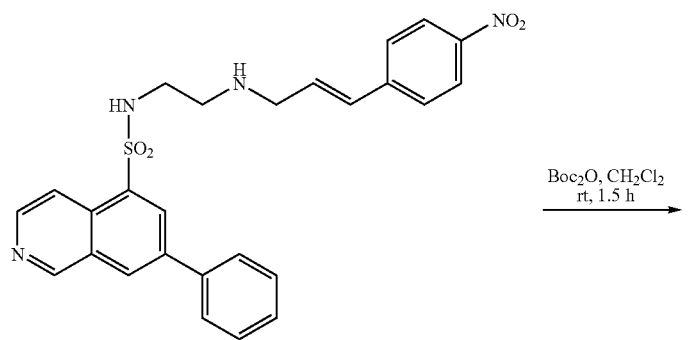
Boc₂O, CH₂Cl₂
rt, 1.5 h
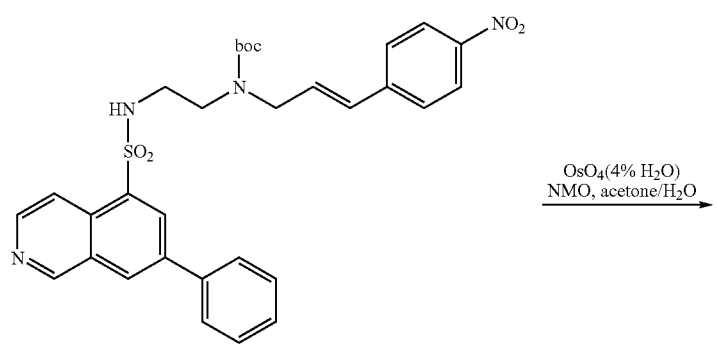
OsO₄(4% H₂O)
NMO, acetone/H₂O
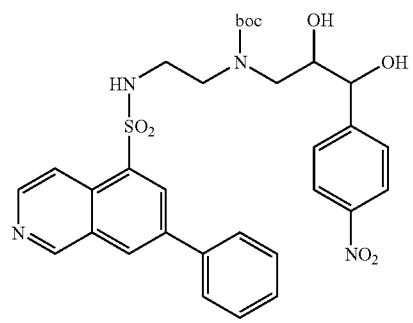

Preparation 85 (Scheme 5)

[2,3-Dihydroxy-3-(4-nitro-phenyl)-propyl]-[2-(7-phenyl-isoquinoline-5-sulfonylamino)-ethyl]-carbonic acid tert-butyl ester Perform a reductive amination of 4-nitrocinnamaldehyde with 7-phenyl-isoquinoline -5-sulfonic acid (2-amino-ethyl)-amide dihydrochloride following a procedure similar to example 1 to give 7-phenyl-isoquinoline-5-sulfonic acid {2-[3-(4-nitro-phenyl)-allylamino]-ethyl}-amide in 85% yield after flash column purification on silica gel (eluent $CH_2Cl_2/CH_3OH$ 95:5).

Add di-tert-butyl dicarbonate (130 mg, 0.60 mmol) to a stirred solution of 7-phenyl-isoquinoline-5-sulfonic acid {2-[3-(4-nitro-phenyl)-allylamino]-ethyl}-amide (272 mg, 0.56 mmol) in anhydrous $CH_2Cl_2$ (5 mL) at room temperature under nitrogen and, stir for 1.5 hours. Quench the reaction by addition of saturated $NaHCO_3$, extract with $CH_2Cl_2$ and dry over $MgSO_4$. Chromatograph the crude product on silica gel, eluent $CH_2Cl_2/CH_3OH$ 96:4 to afford the expected product (58% yield).

Add N-methylmorpholine-N-oxide (42 mg, 0.35 mmol)) and then osmium tetroxide (217 µL 4% in $H_2O$, 0.035 mmol) to a solution of [3-(4-nitro-phenyl)-allyl]-[2-(7-phenyl-isoquinoline-5-sulfonylamino)-ethyl]-carbamic acid tert-butyl ester (190 mg, 0.32 mmol) in acetone (6 mL) and $H_2O$ (6 drops) under nitrogen, and stir at room temperature for 24 hours. Add aqueous $NaHSO_3$ and stir for additional 30 minutes. Extract the mixture with EtOAc, wash with brine, dry over $MgSO_4$ and concentrate. Chromatograph the crude product on silica gel, eluent $CH_2Cl_2$/acetone 5:2 (54% yield). (Used in Example 87)

Preparation 86

{2-[7-(4-hydroxy-phenyl)-isoquinoline-5-sulfonylamino]-ethyl}-[3-(4-nitro-phenyl)-propyl]-carbamic acid tert-butyl ester Bubble HCl (g) into a solution of [2-(7-bromo-isoquinoline-5-sulfonylamino)-ethyl]-carbamic acid tert-butyl ester, (2.88 g, 6.69 mmol) in 110 ml (10:1) $CH_2Cl_2$/MeOH was for several minutes. Stir for 4 h, concentrate the reaction mixture to give the desired solid product as the HCl salt. Dissolve the solid in 200 ml MeOH and add 5N NaOH (2.68 ml, 13.4 mmol). Concentrate the mixture to dryness, then dissolve in (1:1) $CH_2Cl_2$/MeOH and filter to remove NaCl. Concentrate the filtrate to afford 2.55 g of 7-bromo-isoquinoline-5-sulfonic acid (2-amino-ethyl)-amide (approximately 87% pure). ES Positive Ion MS [M+H]$^+$ ions observed: m/z 330 ($^{79}$Br) and m/z 332 ($^{81}$Br).

Add 3-(4-nitro-phenyl)-propionaldehyde (0.390 g, 2.18 mmol to 7-bromo-isoquinoline-5-sulfonic acid (2-amino-ethyl)-amide, [0.75 g (87% purity), 1.98 mmol) in 110 ml (6:5) $CH_2Cl_2$/MeOH. Stir the mixture for 18 h, then placed in an icebath. Add NaBH$_4$ (0.150 g, 3.96 mmol) and stir for 1 h at 0° C. and 2 h at room temperature. Concentrate the reaction mixture, dissolve the residue in $CH_2Cl_2$/MeOH and load onto a silica gel column. Elute with 100% $CH_2Cl_2$, then a gradient of 0-10% (2M NH$_3$ in MeOH) in $CH_2Cl_2$ to give 0.677 g of 7-bromo-isoquinoline-5-sulfonic acid {2-[3-(4-nitro-phenyl)-propylamino]-ethyl}-amide, as a yellow gum in 68% yield. ES Positive Ion MS [M+H]$^+$ ions observed: m/z 493 ($^{79}$Br) and m/z 495 ($^{81}$Br).

Add di-tert-butyldicarbonate to 7-bromo-isoquinoline-5-sulfonic acid {2-[3-(4-nitro-phenyl)-propylamino]-ethyl}-amide, (0.641 g, 1.30 mmol) in 10 ml $CH_2Cl_2$ at RT. After 1 h, concentrate the reaction mixture, then chromatograph on silica gel with a gradient of 0-10% MeOH in $CH_2Cl_2$ to give 0.705 g of [2-(7-bromo-isoquinoline-5-sulfonylamino)-ethyl]-[3-(4-nitro-phenyl)-propyl]-carbamic acid tert-butyl ester, as a white foam in 91% yield. ES Positive Ion MS [M+H]$^+$ ions observed: m/z 593 ($^{79}$Br) and m/z 595 ($^{81}$Br).

Add Pd(dppb)Cl$_2$ (0.0051 g, 0.0085 mmol), 4-hydroxyphenylboronic acid (0.0258 g, 0.187 mmol) and 2M Na$_2$CO$_3$ (0.21 ml, 0.425 mmol) to [2-(7-bromo-isoquinoline-5-sulfonylamino)-ethyl]-[3-(4-nitro-phenyl)-propyl]-carbamic acid tert-butyl ester, (0.101 g, 0.170 mmol) in 3 ml DMF and 0.75 ml MeOH. Heat the reaction mixture at 85° C. for 1 h, then dilute with EtOAc (20 ml) and wash with H$_2$O (2×20 ml) and brine (10 ml). Concentrate the organic layer and chromatograph on silica gel using a gradient of 0-2% MeOH in $CH_2Cl_2$ to give 0.093 g of {2-[7-(4-hydroxy-phenyl)-isoquinoline-5-sulfonylamino]-ethyl}-[3-(4-nitro-phenyl)-propyl]-carbamic acid tert-butyl ester, as a yellow solid in 90% yield. ES Positive Ion MS [M+H]$^+$ ion observed: m/z 607. (Used in Example 98).

Using methods similar to Preparation 86, with the appropriate starting materials, the following compounds may be prepared.

| Preparation # | R | Data | To: Example |
|---|---|---|---|
| 87 | 2-OH | m/z 607 | 91 |
| 88 | 3-NHSO2Me | m/z 684 | 94 |
| 89 | 3-OH | m/z 607 | 99 |

Preparation 90

7-(3-difluoromethylphenyl)-isoquinoline-5-sulfonic acid (2-amino-ethyl)-amide Dissolve [2-(7-bromo-isoquinoline-5-sulfonylamino)-ethyl]-carbamic acid tert-butyl ester (0.13 g, 0.30 mmol) and 3-(difluoromethyl)phenylboronic acid (0.057 g, 0.33 mmol) in DME-methanol (8:1, 10 ml). To the mixture, add K$_3$PO$_4$ (0.13 g, 0.60 mmol), and PdCl$_2$(dppf) (0.012 g, 0.015 mmol). Heat this mixture at 82° C. overnight. Cool the reaction mixture, dilute with water and extract with EtOAc. Wash with brine and evaporate to dryness. Purify by silica gel chromatography to give the desired compound (0.10 g, 71% yield): $^1$H NMR (CDCl$_3$): δ9.39 (s, 1H), 8.66 (m, 2H), 8.43 (d, J=5.7 Hz, 2H), 7.86 (m, 2H), 7.61 (m, 2H), 6.76 (t, J=52.1 Hz, 1H), 5.00 (br s, 1H), 3.18 (m, 2H), 3.03 (m, 2H), 1.37 (s, 9H); ESIMS: m/z 478 (M+H)$^+$.

Suspend {2-[7-(3-difluoromethylpheny)-isoquinoline-5-sulfonylamino]-ethyl}-carbamic acid tert-butyl ester in ethyl acetate (11 mL), and add an excess of 4 M HCl in 1,4-dioxane. Stir overnight, filter the precipitate, wash with dichloromethane, and dry under vacuum to give the desired compound as a white solid (0.092 g, 95% yield): $^1$H NMR (CD$_3$OD): δ9.92 (s, 1H), 9.10 (d, J=7.0 Hz, 1H), 9.04 (m, 2H), 8.80 (d, J=7.0 Hz, 1H), 8.09 (m, 2H), 7.74 (m, 2H), 6.94 (t, J=52.1 Hz, 1H), 3.25 (m, 2H), 3.15 (m, 2H). Load the product onto ion exchange resin and elute with 1N NH$_3$ in methanol and concentrate to dryness to give the free base. (Used in example 97).

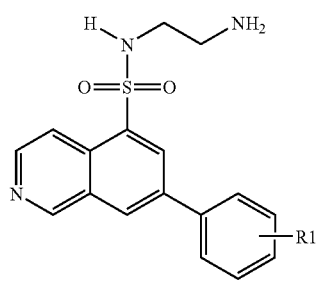

Following a procedure similar to preparation 90, the following compounds may be prepared:

| Preparation # | R1 | To Example # |
|---|---|---|
| 91 | 4-NH$_2$ | 90 |
| 92 | 3-NH$_2$ | 92, 95 |
| 93 | 3-F | 93 |
| 94 | 4-NHSO$_3$CH$_3$ | 96 |

Using the general procedure for preparation of arylpropionaldehyde derivatives, described above, or other well-known procedures described in Scheme 3, the following compounds may be prepared.

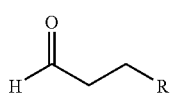

| Preparation | R | Example |
|---|---|---|
| 95 | 4-methanesulfonyl-phenyl | 100 |
| 96 | 3-nitro-phenyl | 101 |
| 97 | 4-trifluoromethanesulfonyl-phenyl | 102 |
| 98 | 2-ethyl-4-nitro-phenyl | 103 |
| 99 | 4-cyano-2-methyl-phenyl | 104 |
| 100 | 3-hydroxy-4-nitro-phenyl | 105 |
| 101 | 4-cyano-3-hydroxy-phenyl | 106 |
| 102 | 3-(tetrahydropyran-2-yloxy)-ethyl)phenyl | |
| 103 | 2-fluoro-4-methoxy-phenyl | |

Following a procedure similar to preparation 90, the following compounds may be prepared:

| Preparation | R1 | Example |
|---|---|---|
| 104 | 3-OH | |
| 105 | 4-OH | |

Preparation 106

4-oxiranylmethyl benzonitrile

Add allyl tri-n-butylstannane (39.3 mmol, 12.18 ml) dropwise to a stirred solution of 4-iodo-benzonitrile (6 g, 26.2 mmol), tetrakis(triphenylphosphine)palladium(0) (1.31 g, 1.5 mmol) and copper (I) iodide (399 mg, 2.09 mmol) in 30 ml of dry 1,4-dioxane under argon atmosphere. Reflux the mixture for 24 hours and then cool to room temperature. Dilute with 40 ml of diethyl ether and add 20 ml of saturated solution of KF and stir for 2 hours. Filter the mixture and wash the organic layer with water (20 ml), brine (20 ml) and dry over sodium sulfate. Evaporate in vacuo and purify by flash chromatography in silica using hexane-ethyl acetate as eluent (20:1) to afford 2.66 g (70%) of 4-allylbenzonitrile Add a solution of 3-chloro-peroxybenzoic acid (5.44 g, 40.92 mmol), in 25 ml of dichloromethane to a solution of 4-allyl-benzonitrile (2.66 g, 18.60 mmol) in 50 ml of dichloromethane. stir at room temperature overnight. Quench with NaHCO$_3$ (15 ml) saturated solution and wash the organic layer three times with NaHCO$_3$ solution and dry over magnesium sulfate. Evaporate in vacuo, and purify by flash chromatography in Hexane-AcOEt (7:1, 1% Et$_3$N) affording 1.44 g (49%) of the title compound. MS m/z 160 (M+H)$^+$.

Preparation 107

4-oxiranylmethyl nitrobenzene

Prepare the title compound using a method similar to Preparation 106, substituting 4-iodonitrobenzene for 4-iodobenzonitrile. MS m/z 180 (M+H)$^+$.

According to the general procedure found in preparation 85, prepare the following intermediates:

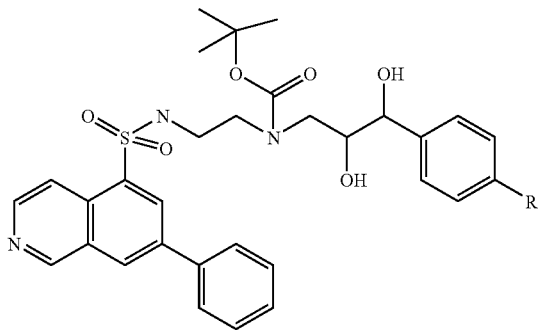

| Preparation | R | Example |
|---|---|---|
| 108 | CN | 112 |
| 109 | SO₂CF3 | 113 |

Preparation 110

3-(4-Nitro-phenyl)-propionaldehyde

Add 1-iodo-4-nitrobenzene (100 g, 400 mmol), allyl alcohol (40 mL, 590 mmol), sodium bicarbonate (80 g, 940 mmol), palladium acetate (4.5 g, 0.05 mmol), tetra-N-butylammonium chloride (110 g, 390 mmol) and dimethylformamide (500 mL) to a 2 L flask and stir. Degas the reaction by pump purging with nitrogen, then heat to 35° C. for 30 hours. Cool the reaction to 0° C. and add methyl tert-butyl ether and water. Stir for 30 minutes then filter over Hyflo Super Cel®. Separate the layers and add tetrahydrofuran to the organic layer and wash with lithium chloride (5% aqueous) and brine. Dry the organic phase over MgSO₄, filter over silica gel and concentrate under reduced pressure to give an oily residue. The title compound was used without purification. $^1$H NMR (CDCl₃, 500.0 MHz): δ 9.81-9.85 (m, 1H), 8.10-8.18 (m, 2H), 7.34-7.40 (m, 2H), 3.00-3.10 (m, 2H), 2.80-3.10 (m, 2H).

Preparation 111

N$^1$-[3-(4-Nitro-phenyl)-propyl]-ethane-1,2-diamine

Add ethylene diamine (200 mL, 3000 mmol) and toluene (1200 mL) to a 3 L flask and cool to <5° C. Add a solution of 3-(4-Nitro-phenyl)-propionaldehyde (63 g, 280 mmol) in toluene (300 mL) via addition funnel over 45 minutes with vigorous stirring. Remove the cooling bath and heat to reflux to remove water by azeotropic distillation (Dean Stark trap). Concentrate the reaction under reduced pressure to an oil. Dilute the crude oil with methanol (450 mL) and cool to 0° C. Add sodium borohydride (13 g, 340 mmol) in 1-2 g portions with stirring, holding the temperature below 5° C. Stir the reaction for 20 minutes at 5° C. and then allow the reaction to warm to room temperature and stir for an additional 30 minutes. Cool to <0° C. and add water and dichloromethane. Separate the layers and extract the aqueous layer with dichloromethane. Combine the organic layers and wash with brine and dry over MgSO₄. Filter the slurry and concentrate under reduced pressure to a red oil (73 g). The title compound was used without purification. $^1$H NMR (CDCl₃, 500.0 MHz): δ 8.12 (d, 2H, J=8 Hz), 7.32 (d, 2H, J=8 Hz), 2.74-2.81 (m, 4H), 2.61-2.67 (m, 4H), 1.84 (p, 2H, J=7.5 Hz), 1.57 (br s, 2H).

Preparation 112

[3-(4-Nitro-phenyl)-propyl]-[2-(2,2,2-trifluoro-acetylamino)-ethyl]carbamic acid tert-butyl ester Add N$^1$-[3-(4-Nitro-phenyl)-propyl]-ethane-1,2-diamine (73 g, 221 mmol) and anhydrous tetrahydrofuran (750 mL) to a 2 L flask and cool to 0° C. Add ethyl trifluoroacetate (28 mL, 234 mmol) dropwise over 15 min via addition funnel. Stir for 30 min before adding di-tert-butyldicarbonate (75 g, 340 mmol) and stir for another 30 min. Allow the reaction to warm to room temperature. Add water and methyl tert-butylmethyl ether and dichloromethane. Separate the layers and add brine to the aqueous layer and extract with dichloromethane. Wash the organic layer with brine, dry over MgSO₄, filter and concentrate under reduced pressure to obtain an oily residue. Purify the residue by flash chromatography (eluting CH₂Cl₂→4% MeOH/CH₂Cl₂) to obtain the title compound. $^1$H NMR (CDCl₃, 500.0 MHz): δ 8.14 (d, 2H, J=8.5 Hz), 7.32 (d, 2H, J=8.5 Hz), 3.42-3.50 (m, 4H), 3.20-3.25 (m, 2H), 2.69 (t, 2H, J=7.5 Hz), 1.87 (p, 2H, J=7.5 Hz), 1.41 (s, 9H).

Preparation 113

(2-Amino-ethyl)-[3-(4-nitro-phenyl)-propyl]-carbamic acid tert-butyl ester

Add [3-(4-Nitro-phenyl)-propyl]-[2-(2,2,2-trifluoro-acetylamino)-ethyl]carbamic acid tert-butyl ester (16 g, 33 mmol), potassium carbonate (23 g, 170 mmol), methanol (100 mL) and water (45 mL) to a 500 mL flask. Heat to 50° C. for 1 hr. Cool the reaction and filter off any solids. Add dichloromethane and water, stir and separated the layers. Extract the aqueous layer with dichloromethane. Combine the organic layers, wash with brine, dry over MgSO₄ and concentrate under reduced pressure to obtain the title compound as an oily residue. The title compound was used without purification. $^1$H NMR (CDCl₃, 500.0 MHz): δ 8.13 (d, 2H, J=9 Hz), 7.32 (d, 2H, J=8.5 Hz), 3.24 (br m, 4H), 2.82 (br m, 2H), 2.69 (t, 2H, J=7.5 Hz), 1.87 (p, J=7.5 Hz), 1.48 (br s, 2H), 1.43 (s, 9H).

Preparation 114

7-Bromo-isoquinoline-5-sulfonic acid sodium salt

Add 7-bromoisoquinoline hydrochloride salt (20 g, 76.1 mmol) in portions to cold (0° C.) fuming sulfuric acid (70 mL, 913 mmol) over 10 minutes keeping the temperature below 3° C. Heat to 90° C. for, 6 hours. Add fuming sulfuric acid (15 mL) and stir 15 h. Cool to room temperature and pour the reaction into ice-water with vigorous stirring. Filter the resulting solids and wash the filter cake with diethyl ether. Transfer the filter cake to a flask with water (100 mL) and adjust the pH with sodium hydroxide until basic. Filter the resulting slurry and dry in a vacuum oven to afford the title compound as an off white solid. The title compound is used with further purification. $^1$H NMR (DMSO, 500.0 MHz): δ 9.32 (s, 1H), 8.6 (d, 1H, J=6 Hz), 8.55 (d, 1H, J=6 Hz), 8.44 (d, 1H, J=2 Hz), 8.17 (d, 1H, J=2 Hz).

Preparation 115

7-Phenyl-isoquinoline-5-sulfonic acid hydrochloride

Add 7-Bromo-isoquinoline-5-sulfonic acid sodium salt (17.8 g, 55.7 mmol), phenylboronic acid (10.2 g, 83.5 mmol), N)N-dimethylformamide (178 mL), 1M sodium carbonate (111 mL, 111 mmol), palladium acetate (0.125 g, 0.56 mmol) and 1,4-bis(diphenylphosphino)butane (0.285 g, 0.67 mmol) to a flask. Heat the slurry to 70° C. for 40 minutes. Cool and filter the solids from the reaction. Add 5N hydrochloric acid to the filtrate until a thick precipitate forms. Filter the precipitate and wash the filter cake with water and then with acetone. Dry the solid in a vacuum oven at 40° C. to provide the title compound as a yellow solid. $^1$H NMR (DMSO, 500.0 MHz): δ 9.87 (s, 1H), 9.15 (d, 1H, J=6.5 Hz), 8.79 (s, 1H), 8.70-8.75 (m, 2H), 7.87 (d, 2H, J=8.5 Hz), 7.63 (t, 2H, J=7.5 Hz), 7.54 (t, 1H, J=7.5 Hz).

Preparation 116

[3-(4-Nitro-phenyl)-propyl]-[2-(7-phenyl-isoquinoline-5-sulfonylamino)-ethyl]-carbamic acid tert-butyl ester Add 7-Phenyl-isoquinoline-5-sulfonic acid hydrochloride (6.2 g, 19 mmol), dimethylformamide (3 mL, 39 mmol) and 1,2-dichloroethane to a 250 mL flask. Cool to −5° C. and add oxalyl chloride (17 mL, 200 mmol) slowly via syringe, holding temperature below 0° C. After addition, heat the reaction to 60° C. for 1 hour. Add additional 1,2-dichloroethane and remove the unreacted oxalyl chloride by distillation. Cool the reaction to <0° C. and add ice water (70 mL), holding temperature below 5° C. Slowly add sodium hydroxide to adjust the pH to 4.

Warm to room temperature and separate the layers. Extract the aqueous layer with dichloromethane (50 mL). Place the organic layer in a 500 ml flask followed by (2-Amino-ethyl)-[3-(4-nitro-phenyl)-propyl]-carbamic acid tert-butyl ester (8.5 g, 23 mmol) dissolved in dichloromethane and stir. Add 1 M aqueous sodium bicarbonate (100 ml, 100 mmol) and stir for 1 hour. Separate the layers and extract the aqueous layer with dichloromethane. Combine the organic layers, wash with brine, and concentrated under reduced pressure to a residue. Purify the residue by flash chromatography (CH$_2$Cl$_2$→2% MeOH/CH$_2$Cl$_2$) to obtain the title compound. $^1$H NMR (CDCl$_3$, 500.0 MHz): δ 9.4 (s, 1H), 8.67-8.70 (m, 2H), 8.41 (d, 1H, J=6 Hz), 8.35 (s, 1H), 8.12 (d, 2H, 8.5 Hz), 7.74 (d, 2H, 8 Hz), 7.56 (t, 2H, J=7.5 Hz), 7.49 (t, 1H, J=7 Hz), 7.24-7.28 (m, 2H), 6.2 (br s, 1H), 3.32 (m, 2H), 3.02-3.17 (m, 4H), 2.61 (t, 2H, J=8 Hz), 1.75 (p, 2H, 7 Hz), 1.42 (s, 9H).

Preparation 117

7-phenyl-isoquinoline-5-sulfonic acid (2-amino-ethyl)-amide

A mixture of 7-bromoisoquinoline (6.5 g, 31.24 mmol) in HSO$_3$Cl (60 mL) is heated to 155° C. with stirring under N$_2$ overnight, and then cooled to room temperature and slowly poured into ice water. After neutralizing with NaHCO$_3$ at 0° C., sulfonyl chloride is extracted with methylene chloride. The organic layer is dried over Na$_2$SO$_4$ and concentrated to 100 mL and dropped to a solution of N-t-butoxycarbonylethylene diamine (5.01 g, 31.24 mmol) in pyridine (2.54 mL, 31.24 mmol) and CH$_2$Cl$_2$ (120 mL). After stirring overnight, the mixture is concentrated, and the residue is dissolved in EtOAc, which is washed with citric acid solution (50%) and brine. The crude material is purified by chromatography over silica gel (gradient 20% hexane in EtOAc) to give 6.50 g (50% yield) of desired product A mixture of 7-bromo-isoquinoline-5-sulfonic acid (2-amino-ethyl)-amide carbamic acid t-butyl ester (1.50 g, 3.49 mmol), 2-phenyl-1,3,2-dioxaborinane (1.129 g, 6.98 mmol), Pd(dppb)Cl$_2$ (211 mg, 0.0349 mmol) and Na$_2$CO$_3$ (2.0M, 12 mL) in ethylene glycol dimethyl ether (60 mL) and CH$_3$OH (15 mL) is heated to 80° C. (oil bath) with stirring overnight. After cooling to room temperature, the mixture is diluted with EtOAc, filtered and concentrated. The residue is dissolved in EtOAc, washed with brine and dried over Na$_2$SO$_4$. The crude material is chromatographed on silica gel (gradient 50% EtOAc in hexane) to give 1.45 g (97% yield) 7-phenyl-isoquinoline-5-sulfonic acid (2-amino-ethyl)-amide carbamic acid t-butyl ester.

7-Phenyl-isoquinoline-5-sulfonic acid (2-amino-ethyl)-amide carbamic acid t-butyl ester (1.44 g, 3.37 mmol) is dissolved in CH$_3$OH (20 mL) and CH$_2$Cl$_2$ (20 mL) and HCl (37%, 5.0 mL) is added. After the mixture is stirred overnight, the mixture is concentrated and dried under high vacuum to give 1.34 g (100% yield) 7-phenyl-isoquinoline-5-sulfonic acid (2-amino-ethyl)-amide hydrochloride. Load the product onto ion exchange resin and elute with 1N NH$_3$ in methanol and concentrate to dryness to give the free base.

EXAMPLES

Example 1

7-Phenyl-isoquinoline-5-sulfonic acid [2-(3-naphthalen-1-yl-propylamino)-ethyl]-amide dihydrochloride

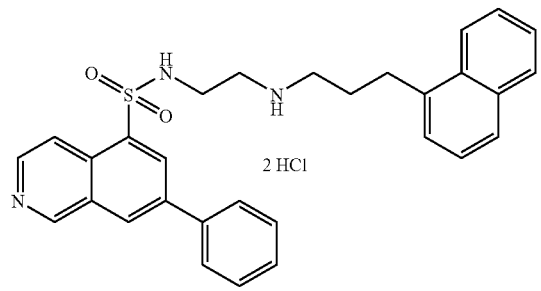

Stir a mixture of 7-phenyl-isoquinoline-5-sulfonic acid (2-amino-ethyl)-amide (0.25 mmol, 1.0 eq) and 3-naphthalen-1-yl-propionaldehyde (0.25 mmol, 1.0 eq) in 1,2-dichloroethane (DCE) (2.0 mL) at room temperature for six (6) hours, and then add sodium triacetoxyborohydride (0.6 mmol, 2.4 eq). Stir overnight, then dilute the mixture with CH$_3$OH, and apply to a cation exchange column (10 g), wash with a mixture of, CH$_3$OH and CH$_2$Cl$_2$ (1:1), then NH$_3$ (2.0 M in CH$_3$OH). Purify the residue on silica gel (gradient 10% CH$_3$OH in CH$_2$Cl$_2$) to give 100 mg the free amine product as oil. Dissolve the free amine in CH$_3$OH (15 mL) and treat dropwise with 37% HCl aqueous solution (1.0 mL) with stirring. Concentrate the resultant solution and dried under vacuum at 37° C. to give the title compound as a white powder. $^1$H NMR (DMSO-d$_6$, 400 MHz): 9.65 (1H, s), 8.85 (2H, br), 8.75 (1H, s), 8.69 (1H, d, J=6.0 Hz), 8.64 (1H,s), 8.53 (1H, t, J=6.0 Hz), 8.07 (1H, d, J=8.0 Hz), 7.91 (2H, d, J=7.6 Hz), 7.78 (1H, d, J=8.0 Hz), 7.49-7.61 (4H, s), 7.46 (1H, d, J=7.6 Hz), 7.35 (1H, d, J=7.2 Hz), 3.12-3.15 (2H, m), 3.07 (2H, t, J=7.6 Hz), 2.95-3.02 (4H, m), 1.93-1.99 (2H, m). IS-MS, m/e 582.58 (m+1)

Using a procedure similar to that described in Example 1 and using the appropriate starting materials, the following compounds may be prepared and isolated as the hydrochloride salt. The skilled artisan will recognize that the compounds exemplified below can be converted from their free base form to the hydrochloride salt by using excess hydrochloric acid in an appropriate solvent, with the exception of Example 71, which is prepared as the monohydrochloride salt by addition of a stoichiometric amount of aqueous HCl and lyophylization.

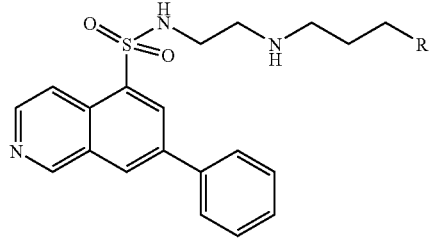

| Ex # | Prep # | R | Data |
|---|---|---|---|
| 2 | 2 | 4-trifluoromethylphenyl | $^1$H NMR (DMSO-$d_6$, 400 MHz): 9.64 (1H, s), 8.88 (2H, br), 8.85 (1H, s), 8.72-8.74 (1H, m), 8.69 (1H, t, J = 6.0 Hz), 8.64 (1H, d, J = 2.0 Hz), 8.51 (1H, d, J = 6.6 Hz), 7.91 (2H, d, J = 6.8 Hz), 7.63 (2H, d, J = 8.4 Hz), 7.59 (2H, d, J = 7.6 Hz), 7.50 (1H, t, J = 6.0 Hz), 7.41 (2H, d, J = 7.6 Hz), 3.11-3.15 (2H, m), 2.95-2.97 (2H, m), 2.84-2.86 (2H, m), 2.69 (2H, t, J = 8.0 Hz), 1.85-1.88 (2H, m) IS-MS, m/e 514.3 (m + 1) |
| 3 | 3 | 4-nitrophenyl | $^1$H NMR (DMSO-$d_6$, 400 MHz): 9.77 (1H, s), 9.11 (2H, br), 8.95 (1H, s), 8.86 (1H, t, J = 5.6 Hz), 8.81 (1H, d, J = 6.0 Hz), 8.73 (1H, s), 8.65 (1H, d, J = 5.6 Hz), 8.19 (2H, d J = 7.6 Hz), 7.97 (2H, d, J = 7.6 Hz), 7.73 (2H, d, J = 8.0 Hz), 7.55 (1H, d, J = 7.6 Hz), 7.51 (2H, d, J = 8.4 Hz), 3.18-3.21 (2H, m), 2.98-3.02 (2H, m), 2.77-2.79 (2H, m), 2.79 (2H, t, J = 7.6 Hz), 1.89-1.96 (2H, m) IS-MS, m/e 491.38 (m + 1) |
| 4 | 4 | 4-bromophenyl | $^1$H NMR (DMSO-$d_6$, 400 MHz): 9.58 (1H, s), 8.78-8.79 (3H, s), 8.62 (1H, d, J = 6.0 Hz), 8.62 (1H, t, J = 6.0 Hz), 8.57 (1H, d, J = 1.2 Hz), 8.45 (1H, d, J = 6.4 Hz), 7.85 (2H, d, J = 7.2 Hz), 7.53 (2H, t, J = 7.6 Hz), 7.45 (1H, d, J 7.0 Hz), 7.40 (2H, d, J = 8.0 Hz), 7.09 (2H, d, J = 8.4 Hz), 3.05-3.07 (2H, m), 2.88-2.90 (2H, m), 2.77-2.79 (2H, m), 2.51 (2H, t, J = 7.6 Hz), 1.75-1.77 (2H, m) IS-MS, m/e 526.0 (m + 1) |
| 5 | 5 | 3-cyanomethylphenyl | $^1$H NMR (DMSO-$d_6$, 400 MHz): 9.62 (1H, s), 8.84 (2H, br), 8.74 (1H, d, J = 6.8 Hz), 8.65-8.67 (1H, m), 8.50 (1H, d, J = 6.0 Hz), 7.91 (2H, d, J = 7.6 Hz), 7.60 (2H, t, J = 8.0 Hz), 7.49-7.52 (1H, m), 7.36 (1H, d, J = 7.6 Hz), 7.23-7.29 (3H, m), 7.16 (1H, s), 7.03 (1H, s), 3.13-3.15 (2H, m), 2.93-3.15 (4H, m), 2.64 (2H, t, J = 8.0 Hz), 1.82-1.85 (2H, m) IS-MS, m/e 582.58 (m + 1) |
| 6 | 6 | 2-methoxycaxbonylphenyl | $^1$H NMR (DMSO-$d_6$, 400 MHz): 9.62 (1H, s), 8.96 (2H, br), 8.89 (1H, s), 8.77 (1h, br), 8.68 91H, s), 8.59-8.60 (1h, m), 7.93 (2H, d, J = 7.6 Hz), 7.79 (1H, d, J = 7.2 Hz), 7.60 (2H, t, J = 6.8 Hz), 7.51 (2H, t, J = 7.6 Hz), 7.32 (2H, t, J = 6.4 Hz), 3.81 (3h, s), 3.15-3.17 (2H, m), 2.97-2.97 (2H, m), 2.86-2.88 (2H, m), 1.83-1.85 (2H, m) IS-MS, m/e 504.63 (m + 1) |
| 7 | 51 | 2-[1,4]diazepin-1-yl-phenyl | $^1$H NMR (DMSO-$d_6$, 400 MHz): 9.70 (1H, s), 9.23 (2H, br), 9.13 (2H, br), 8.90 (1H, s), 8.81-8.83 (1H, m), 8.76 (1H, d, J = 6.4 Hz), 8.68 (1H, s), 8.60 (1H, d, J = 6.0 Hz), 7.93 (2H, d, J = 7.2 Hz), 7.57 (2H, t, J = 7.6 Hz), 7.51 (1H, t, J = 6.8Hz), 7.14-7.20 (3H, m), 7.03-7.07 (2H, m), 3.19-3.28 (8H, m), 2.91-2.96 (6H, m), 2.63-2.64 |

| | | | |
|---|---|---|---|
| | | | (2H, m), 2.10-2.12 (2H, m), 1.86-1.88 (2H, m) |
| | | | IS-MS, m/e 544.58 (m + 1) |
| 8 | 7 | biphenyl-2-yl | $^1$H NMR (DMSO-d$_6$, 400 MHz): 8.84 (1H, s), 8.74 (2H, br), 8.61-8.65 (2H, m), 8.47-8.48 (1H, m), 7.90 (2H, d, J = 7.6 Hz), 7.59 (2H, t, J = 7.6 Hz), 7.50 (1H, t, J = 7.2 Hz), 7.41-7.42 (2H, m), 7.37-7.39 (1H, m), 7.24-7.29 (5H, m), 7.13-7.16 (2H, m), 3.06-3.07 (2H, m), 2.86-2.90 (2H, m), 2.68-2.70 (2H, m), 2.54-2.56 (2H, m), 1.67-1.70 (2H, m) |
| | | | IS-MS, m/e 522.58 (m + 1) |
| 9 | 8 | 2-phenoxyphenyl | $^1$H NMR (DMSO-d$_6$, 400 MHz): 8.84-8.86 (3H, m), 8.74-8.74(1H, m), 8.71-8.72 (1H, m), 8.67 (1H, d, J = 5.6 Hz), 8.53-8.54 (1H, m), 7.91 (2H, d, J = 7.6 Hz), 7.57-7.61 (2H, m), 7.29-7.34 (3H, m), 7.20-7.23 (2H, m), 7.08-7.11 (2H, m), 6.90 (2H, d, J = 8.8 Hz), 6.79-7.82 (1H, m), 3.10-3.12 (2H, m), 2.92-2.94 (2H, m), 2.83-2.85 (2H, m), 2.57 (2H, t, J = 7.6 Hz), 1.82-1.84 (2H, m) |
| | | | IS-MS, m/e 538.70 (m + 1) |
| 10 | 52 | 2-(N-morpholinyl)phenyl | $^1$H NMR (DMSO-d$_6$, 400 MHz): 9.70 (1H, s), 8.94 (2H, br), 8.90 (1H, s), 8.75-8.80 (1H, m), 8.68 (1H, d, J = 2.0 Hz), 8.59 (2H, d, J = 6.4 Hz), 7.92 (2H, d, J = 7.2 Hz), 7.59 (2H, t, J = 7.6 Hz), 7.51 (1H, t, J = 7.2 Hz), 7.10-7.20 (3H, m), 7.03 (1H, t, J = 6.8 Hz), 3.69-3.70 (4H, m), 3.14-3.17 (2H, m), 2.93-2.96 (2H, m), 2.48-2.86 (2H, m), 2.74-2.78 (2H, m), 2.62 (2H, t, J = 8.0 Hz), 1.85-1.89 (2H, m) |
| | | | IS-MS, m/e 531.69 (m + 1) |
| 11 | 53 | 2-piperazin-1-yl-phenyl) | $^1$H NMR (DMSO-d$_6$, 400 MHz): 9.71 (1H, s), 9.21 (2H, br), 9.17 (2H, br), 8.86-8.90 (2H, m), 8.76 (2H, d, J = 6.4 Hz), 8.69 (1H, s), 8.61 (1H, d, J = 6.0 Hz), 7.94 (2H, d, J = 6.8 Hz), 7.59 (2H, t, J = 7.6 Hz), 7.51 (1H, t, J = 7.6 Hz), 7.17-7.26 (2H, m), 7.05-7.10 (2H, m), 3.20-3.24 (6H, m), 2.86-2.97 (6H, m), 2.85-2.87 (2H, m), 2.62 (2H, t, J = 7.2 Hz), 1.88-1.90 (2H, m) |
| | | | IS-MS, m/e 530.71 (m + 1) |
| 12 | 9 | 2-isopropylphenyl | $^1$H NMR (DMSO-d$_6$, 400 MHz): 9.62 (1H, s), 8.84 (1H, s), 8.74-8.76 (3H, m), 8.66 (1H, t, J = 5.6 Hz), 8.63 (1H,s), 8.49 (1H, d, J = 5.6 Hz), 7.91 (2H, d, J = 7.6 Hz), 7.59 (2H, t, J = 8.0 Hz), 7.50 (1H, t, J = 6.8 Hz), 7.25 (1H, d, J = 7.6 Hz), 7.14-7.17 (1H, m), 7.07 (2H, d, J = 4.0 Hz), 3.04-3.12 (3H, m), 2.97-2.97 (4H, m), 2.60 (2H, t, J = 7.6 Hz), 1.73-1.76 (2H, m), 1.14(6H, J 6.8 Hz). |
| | | | IS-MS, m/e 488.69 (m + 1) |
| 13 | 10 | 2-cyanophenyl | $^1$H NMR (DMSO-d$_6$, 400 MHz): 9.61 (1H, s), 8.83 (1H, s), 8.72-8.74 (4H, m), 8.60-8.61 (2H, m), 8.47 (1H, d, J = 6.0 Hz), 7.90 (2H, d, J = 8.4 Hz), 7.80 (1H, d, J = 7.6 Hz), 7.57-7.62 (3H, m), 7.40-7.52 (4H, m), 3.14-3.15 (2H, m), 2.92-3.04 (4H, m), 2.80 (2H, t, J = 8.0 Hz), 1.88-1.91 (2H, m) |
| | | | IS-MS, m/e 471.60 (m + 1) |
| 14 | 11 | 2-phenylsulfonylphenyl | $^1$H NMR (DMSO-d$_6$, 400 MHz): 9.63 (1H, s), 8.85 (3H, br), 8.69-8.74 (2H, m), 8.64 (1H, s), 8.51 (1H, d, J = 6.0Hz), 8.06 (1H, d, J = 8.0 Hz), 7.91 (2H, d, J = 8.0 Hz), 7.85 (2H, d, J = 8.0 Hz), 7.64-7.66 (2H, m), 7.56-7.62 (4H, m), 7.42-7.50 (2H, m(, 7.41 (1H, d, J = 7.6 Hz), 3.14-3.15 (2H, m), 2.93-2.95 (2H, m), 2.78-2.81 (4H, m), 1.72-1.74 (2H, m) |
| | | | IS-MS, m/e 586.75 (m + 1) |
| 15 | 54 | 2-N-piperidinylphenyl | $^1$H NMR (DMSO-d$_6$, 400 MHz): 9.78 (1H, s), 9.23 (1H, br), 8.78-8.92 (2H, m), 8.68-8.74 (3H, m), 7.95 (2H, d, J = 7.2 Hz), 7.51-7.59 (3H, m), 7.09-7.33 (3h, m), 3.19-3.21 (2H, m), 3.05-3.07 (6H, m), 2.47-2.49 (6H, m), 1.93-1.95 (2H, m)m 1.73-1.74 (2H, m), |

|   |   |   | -continued |
|---|---|---|---|
|   |   |   | 1.57-1.58 (2H, m)<br>IS-MS, m/e 529.70 (m + 1) |
| 16 | 12 | 2-propylphenyl | ¹H NMR (DMSO-d₆, 400 MHz): 9.66 (1H, s), 8.87 (3H, br), 8.72-8.74 (2H, m), 8.65-8.67 (1H, m), 8.55 (1H, d, J = 6.0 Hz), 7.92 (2H, d, J = 6.4 Hz), 7.58 (2H, d, J = 8.0 Hz), 7.51 (1H, t, J = 6.8 Hz), 7.09-7.10 (4H, m), 3.13-3.15 (2H, m), 2.90-2.97 (4H, m), 2.48-2.56 (6H, m), 1.77-1.79 (2H, m), 1.48-1.50 (2H, m), 0.90 (2H, t, .1 = 3.2 Hz)<br>IS-MS, m/e 488.67 (m + 1) |
| 17 | 47 | 2-(2-hydroxyethyl)phenyl | ¹H NMR (300 MHz, CD₃OD) δ 9.99 (s, 1H) 9.15 (d, 1H, J = 6.7 Hz), 9.07 (d, 1H, J = 1.6 Hz), 9.03 (s, 1H), 8.81 (d, 1H, J = 6.7 Hz), 7.97 (d, 2H, J = 7.0 Hz), 7.58-7.68 (m, 3H), 7.15-7.24 (m, 4H), 3.76 (t, 2H, J = 7.3 Hz), 3.22-3.30 (m, 4H), 3.14 (t, 2H, J = 7.7 Hz), 2.90 (t, 2H, J = 7.2 Hz), 2.80 (t, 2H, J = 7.7 Hz), 2.03 (q, 2H, J = 7.6 Hz).<br>ESIMS: m/z 490 (M + H)⁺. |
| 18 | 13 | 3-hydroxyphenyl | ¹H NMR (300 MHz, CD₃OD) δ 9.95 (s, 1H) 9.11 (d, 1H, J = 6.5 Hz), 9.04 (S. 1H), 9.01 (s, 1H), 8.79 (d, 1H, J = 6.5 Hz), 7.93 (d, 2H, J = 8.1 Hz), 7.54-7.66 (m, 3H), 7.10 (t, 1H, J = 8.1 Hz), 6.61-6.70 (m, 3H), 3.16-3.26 (m, 4H), 3.05 (t, 2H, J = 8.0 Hz), 2.66 (t, 2H, J = 8.0 Hz), 2.01 (q, 2H, J = 8.0 Hz).<br>ESIMS: m/z 462 (M + H)⁺. |
| 19 | 46 | 4-hydroxyphenyl | ¹H NMR (CD₃OD): δ 9.96 (br. s, 1H), 9.15 (d, J = 6.4 Hz, 1H), 9.05 (d, J = 8.71 Hz, 2H), 8.79 (d, J = 5.8 Hz, 1H), 7.94 (d, J = 6.97 Hz, 2H), 7.6 (m, 3H), 7.06 (d, J = 8.71 Hz, 2H), 6.72 (d, J = 8.1 Hz, 2H), 3.19 (m, 4H), 3.0 (m, 2H), 2.63 (t, J = 7.3 Hz, 2H), 1.98 (m, 2H).<br>MS m/z 462.1 (M + H)⁺. |
| 20 | 14 | 4-(N,N-dimethylcarboxamido)phenyl | ¹H NMR (CD₃OD): δ 10.01 (bs, 1H) 9.17 (bd, J = 6.9 Hz, 1H), 9.07 (bs, 1H), 9.04 (bs, 1H), 8.80 (bd, J = 7.3 Hz, 1H), 7.95 (bd, J = 7.3 Hz, 2H), 7.53-7.68 (m, 3H), 7.34 and 7.39 (AA'BB' system, J = 8.2 Hz, 4H), 3.16-3.29 (m, 4H), 3.04-3.14 (m, 5H), 3.00 (bs, 3H), 2.79 (t, J = 7.7 Hz, 2H), 2.06 (quint, J = 7.9 Hz, 2H).<br>ESIMS: m/z 517 [M + H]⁺. |
| 21 | 15 | 4-(N-propylsulfonamido)phenyl | ¹H-NMR (DMSO-d6): 10.00 (bs, 1H), 9.16 (d, 1H, J = 6.5 Hz), 9.07 (d, 1H, J = 1.8 Hz), 9.04 (bs, 1H), 8.80 (d, 1H, J = 6.5 Hz), 7.96 (d, 2H, J = 8.5 Hz), 7.78 (d, 2H, J = 8.3 Hz), 7.54-7.66 (m, 3H), 7.46 (d, 2H, J = 8.3 Hz), 3.22-3.33 (m, 4H), 3.08-3.13 (m, 2H), 2.77-2.84 (m, 4H), 2.05-2.14 (m, 2H), 1.40-1.49 (m, 2H), 0.87 (t, 3H, J = 7.5Hz).<br>MS Data (ESI+): m/z 567.1 [M + H]. |
| 22 | 16 | 2-hydroxyphenyl | ¹H NMR (CD₃OD): δ 9.96 (bs, 1H), 9.11 (bd, J = 5.7 Hz, 1H), 9.04 (s, 1H), 9.01 (s, 1H), 8.79 (bs, 1H), 7.94 (bd, J = 8.1 Hz, 2H), 7.52-7.68 (m, 3H), 7.09 (d, J = 7.3 Hz, 1H), 7.04 (t, J = 8.1 Hz, 1H), 6.72-6.81 (m, 2H), 3.13-3.28 (m, 4H), 3.05 (bt, J = 7.3 Hz, 2H), 2.71 (bt, J = 7.0 Hz, 2H), 1.95-2.10 (m, 2H).<br>ESIMS: m/z 462 [M + H]⁺. |
| 23 | 17 | 4-(N-propylcarboxamido)phenyl | ¹HNMR (300 MHz, CD₃OD) δ 9.96 (s, 1H), 9.12 (d, 1H, J = 7.3 Hz), 9.05 (d, 1H, J = 1.5 Hz), 9.01 (s, 1H), 8.79 (d, 1H, J = 7.3 Hz), 7.94 (d, 2H, J = 7.3 Hz), 7.77 (d, 2H, J= 8.1 Hz), 7.56-7.66 (m, 3H), 7.35 (d, 2H, J = 8.1 Hz), 3.33 (t, 2H, J = 7.3 Hz), 3.18-3.27 (m, 4H), 3.08 (t, 2H, J = 7.3 Hz), 2.80 (t, 2H, J = 7.3 Hz), 2.06 (q, 2H, J = 7.3 Hz), 1.62 (sex, 2H, J = 7.3 Hz), 0.97 (t, 3H, J = 7.3 Hz).<br>ESIMS: m/z 531 (M + H)⁺. |
| 24 | 18 | 4-(N,N-dimethylsulfonamido)phenyl | ¹H NMR (CD₃OD): δ 9.89 (br. s, 1H), 8.90 (m, 1H), 8.98 (d, J = 1.5 Hz, 1H), 8.95 (d, J = 2.01 Hz, 1H), 8.78 (br. s, 1H), 7.92 (m, 2H), 7.68 (d, J = 8.07 Hz, 1H), 7.62 (m, 2H), 7.57 (m, 3H), 3.23 (m, 4H), 3.1 (m, 2H), 2.85 (t, J = 7.7 Hz, 2H), 2.67 (s, 6H), 2.09 (m, 2H).<br>MS m/z 553.2 (M + H)⁺. |

| | | -continued | |
|---|---|---|---|
| 25 | 19 | 4-aminophenyl cyclopropanecarboxylic acid amide | $^1$H NMR (300 MHz, CD$_3$OD) δ 9.97 (s, 1H), 9.13 (d, 1H, J = 7.3 Hz), 9.05 (d, 1H, J = 1.6 Hz), 9.02 (s, 1H), 8.79 (d, 1H, J = 7.3 Hz), 7.94 (d, 2H, J = 7.3 Hz), 7.56-7.66 (m, 3H), 7.48 (d, 2H, J = 8.1 Hz), 7.18 (d, 2H, J = 8.1 Hz), 3.18-3.28 (m, 4H), 3.05 (t, 2H, J = 7.3 Hz), 2.70 (t, 2H, J = 7.3 Hz), 2.01 (q, 2H, J = 7.3 Hz), 1.71-1.79 (m, 1H), 0.92-0.96 (m, 2H), 0.81-0.91 (m, 2H) ESIMS: m/z 529 (M + H)$^+$. |
| 26 | 20 | 4-aminophenyl propionic acid amide | $^1$H NMR (CD$_3$OD): δ 10.02 (s, 1H), 9.18 (d, J = 6.8 Hz, 1H), 9.07 (s, 1H), 9.04 (s, 1H), 8.79 (d, J = 6.8 Hz, 1H), 7.95 (d, J = 7.3 Hz, 2H), 7.51-7.66 (m, 3H), 7.47 (d, J = 8.1 Hz, 2H), 7.17 (d, J = 8.9 Hz, 2H), 3.23-3.29 (m, 2H), 3.14-3.23 (m, 2H), 3.04 (bt, J = 8.1 Hz, 2H), 2.69 (t, J = 7.3 Hz, 2H), 2.37 (q, J = 7.6 Hz, 2H), 2.01 (quint, J = 7.7 Hz, 2H), 1.19 (t, J = 7.6 Hz, 3H). ESIMS: m/z 517 [M + H]$^+$. |
| 27 | 21 | 4-(1,1,2,2-tetrafluoroethoxy)phenyl | $^1$H NMR (DMSO-d$_6$, 400 MHz): 9.69 (1H, s), 8.89 (2H, br), 8.76-8.78 (2H, m), 8.68 (1H, s), 8.56 (1H, s), 7.95 (2H, d, J = 7.2 Hz), 7.61 (2H, d, J = 6.4 Hz), 7.54-7.55(1H, m), 7.31 (2H, d, J = 7.6 Hz), 7.21 (2H, d, J = 8.4 Hz), 3.15-3.16 (2H, m), 2.99-3.04 (2H, m), 2.88-2.89 (2H, m), 2.64-2.65 (2H, m), 1.87-1.88 (2H, m) IS-MS, m/e 562.62 (m + 1) |
| 28 | 22 | 4-aminophenyl acetic acid amide | $^1$H NMR (CD$_3$OD): δ 10.02 (br. s, 1H), 9.18 (d, J = 6.7 Hz, 1H), 9.07 (m, 2H), 8.80 (d, J = 7.15 Hz, 1H), 8.78 (br. s, 1H), 7.96 (d, J = 7.40 Hz, 2H), 7.92 (m, 2H), 7.62 (m, 3H), 7.45 (d, J = 8.24 Hz, 2H), 7.17 (d, J = 8.25 Hz, 2H), 3.26 (m, 2H), 3.18 (m, 2H), 3.04 (m, 2H) 2.69 (t, J = 7.4 Hz, 2H), 2.11 (s, 3H), 2.04 (m, 2H). MS m/z 503.1 (M + H)$^+$. |
| 29 | 23 | 4-carboxamidophenyl | $^1$H NMR (300 MHz, CD$_3$OD) δ 10.00 (s, 1H), 9.17 (d, 1H, J = 7.3 Hz), 9.07 (d, 1H, J = 1.6 Hz), 9.04 (s, 1H), 8.80 (d, 1H, J = 7.3 Hz), 7.95 (d, 2H, J = 7.3 Hz), 7.83 (d, 2H, J = 8.1 Hz), 7.57-7.66 (m, 3H), 7.36 (d, 2H, J = 8.1 Hz), 3.19-3.28 (m, 4H), 3.08 (t, 2H, J = 7.3 Hz), 2.81 (t, 2H, J = 7.3 Hz), 2.07 (q, 2H, 7.3 Hz). ESIMS: m/z 489 (M + H)$^+$. |
| 30 | 24 | 4-difluoromethoxyphenyl | $^1$H NMR (DMSO-d$_6$, 400 MHz): 9.70 (1H, s), 8.91 (2H, br), 8.77-8.79 (1H, m), 8.68-8.69 (1H, m), 8.58 (1H, d, J = 6.4 Hz), 7.95 (2H, d, J = 6.8 Hz), 7.53-7.63 (3H, m), 7.35-7.39 (1H, m), 7.20-7.27 (2H, m), 7.02-7.17 (2H, m), 3.17-3.18 (2H, m), 2.99-3.00 (2H, m), 2.86-2.88 (2H, m), 2.62 (2H, t, J = 7.2 Hz), 1.85-1.87 (2H, m) IS-MS, m/e 511.60 (m + 1) |
| 31 | 25 | 3-methoxyphenyl | $^1$H NMR (DMSO): δ 9.62(s, 1H), 8.93-8.73 (m, 4H), 8.70 (t, J = 5.7 Hz, 1H), 8.67 (d, J = 1.8 Hz, 2H), 8.55 (d, J = 6.5 Hz, 1H), 7.98-7.92 (m, 2H), 7.66-7.60 (m, 2H), 7.54 (tt, J1 = 2.0 Hz, J2 = 7.4Hz, 1H), 7.25-7.19 (m, 1H), 6.81-6.75(m, 3H), 3.75 (s, 3H), 3.16 (q, J = 6.4 Hz, 2H), 3.05-2.95 (m, 2H), 2.93-2.81 (m, 2H), 2.60 (t, J = 7.6 Hz, 2H), 1.87 (p, J = 7.2 Hz, 2H) LCMS: m/z 476 (M + H)$^+$ 474(M − H)$^-$. |
| 32 | 26 | 3-cyanophenyl | $^1$H NMR (CD$_3$OD): δ 9.99 (bs, 1H), 9.15 (bd, J = 7.3 Hz, 1H), 9.06 (s, 1H), 9.03 (s, 1H), 8.80 (d, J = 7.3 Hz, 1H), 7.95 (d, J = 7.3 Hz, 2H), 7.46-7.69 (m, 7H), 3.17-3.28 (m, 4H), 3.09 (bt, J = 7.7 Hz, 2H), 2.80 (t, J = 7.7 Hz, 2H), 2.06 (quint, J = 7.9 Hz, 2H). ESIMS: m/z 571 [M + H]$^+$. |
| 33 | 27 | 4-cyanophenyl | $^1$H NMR (CD$_3$OD): δ 9.98 (br. s, 1H), 9.14 (d, J = 6.39 Hz, 1H), 9.04 (d, J = 7.31 Hz, 2H), 8.80 (br. s, 1H), 7.94 (d, J = 7.31 Hz, 2H), 7.62 (m, 5H), 7.46 (d, J = 7.31 Hz, 2H), 3.22 (m, 4H), 3.08 (t, J = 7.72 Hz, 2H), 2.82 (t, |

| | | | -continued |
|---|---|---|---|
| 34 | 28 | 4-aminophenyl methoxyacetic acid amide | J = 7.72 Hz, 2H), 2.01 (m, 2H).<br>MS m/z 471.2 (M + H)+.<br>1H-NMR (DMSO-d6): δ 10.01 (bs, 1H), 9.17 (d, 1H, J = 5.8 Hz), 9.06 (bs, 1H), 9.03 (bs, 1H), 8.79 (bd, 1H, J = 5.8 Hz), 7.94 (d, 2H, J = 7.5 Hz), 7.54-7.63 (m, 3H), 7.51 (d, 2H, J = 8.7 Hz), 7.20 (d, 2H, J = 8.7 Hz), 4.01 (s, 2H), 3.47 (s, 3H), 3.16-3.20 (m, 2H), 3.02-3.07 (m, 2H), 2.74-2.79 (m, 2H), 2.70 (d, 2H, J = 7.5 Hz), 1.96-2.07 (m, 2H).<br>MS (ESI+): m/z 533.2 [M + H] |
| 35 | 29 | 4-methylsulfanylphenyl | 1H NMR (CD3OD): δ 9.93 (bs, 1H), 9.07 (d, J = 6.7 Hz, 1H), 9.02 (d, J = 1.6 Hz, 1H), 8.99 (s, 1H), 8.78 (bd, J = 7.3 Hz, 1H), 7.89-7.97 (m, 2H), 7.53-7.67 (m, 3H), 7.17 and 7.22 (AA'BB' system, J = 8.6 Hz, 4H), 3.14-3.27 (m, 4H), 3.05 (bt, J = 8.0 Hz, 2H), 2.70 (t, J = 7.5 Hz, 2H), 2.44 (s, 3H), 2.06 (quint, J = 7.8 Hz, 2H).<br>ESIMS: m/z 492 [M + H]+. |
| 36 | 64 | 5-fluoro-biphenyl-2-yl | 1H NMR (DMSO-d6, 400 MHz): δ 9.64 (1H, s), 8.84 (1H, d, J = 1.6 Hz), 8.73 (2H, br), 8.63-8.65 (1H, m), 8.61 (1H, d, J = 2.4 Hz), 8.50 (1H, d, J = 6.4 Hz), 7.90 (2H, d, J = 6.0 Hz), 7.60 (2H, t, J = 7.2 Hz), 7.43-7.46 (1H, m), 7.34-7.36 (2H, m), 7.30-7.32 (2H, m), 7.27-7.29 (2H, m), 7.15 (1H, dt, J, = 2.4 Hz, J2 = 8.4 Hz), 6.98 (1H, dd, J1 = 3.2 Hz, J2 = 9.6 Hz), 3.05-3.09 (2H, m), 2.87-2.89 (2H, m), 2.68-2.70 (2H,m), 2.50-2.52 (2H,m), 1.65-1.68 (2H, m).<br>IS-MS, m/e 540.50 (m + 1) |
| 37 | 30 | 2,4-bistrifluoromethylphenyl | 1H NMR (DMSO-d6, 400 MHz): δ 9.65 (1H, s), 8.95 (2H, br), 8.86 (1H, d, J = 1.2 Hz), 8.75 (1H, d, J = 6.4 Hz), 8.71 (1H, t, J = 6.0 Hz), 8.65 (1H, d, J = 2.0 Hz), 8.53 (1H, d, J = 6.0 Hz), 8.03 (1H, d, J = 8.4 Hz), 7.96 (1H, s), 7.92 (2H, d, J = 8.2 Hz), 7.74 (2H, d, J = 8.4 Hz), 7.59 (2H, d, J = 7.6 Hz), 7.48-7.52 (1H, m), 3.13-3.18 (2H, m), 2.87-3.00 (4H, m), 2.85 (2H, t, J = 7.6 Hz), 1.85-1.93 (2H, m)<br>IS-MS, m/e 582.58 (m + 1) |
| 38 | 31 | 2-chloro-4-nitrophenyl | 1H NMR (DMSO-d6, 400 MHz): δ 9.69 (1H, s), 9.03 (2H, br), 8.88 (1H, s), 8.76-8.77 (2H, m), 8.66 (1H, d, J = 2.0 Hz), 8.57 (1H, d, I = 6.4 Hz), 8.25 (1H, d, J = 2.0 Hz), 8.14 (1H, dd, J1 = 2.4 Hz, J2 = 8.4 Hz), 7.92 (2H, d, J = 7.6 Hz), 7.64 (1H, d, J = 8.8 Hz), 7.59 (2H, t, J = 8.0 Hz), 7.48-7.52 (1H, m), 3.15-3.17 (2H, m), 2.29-2.94 (4H, m), 2.83 (2H, t, J = 8.0 Hz), 1.86-1.89 (2H, m)<br>IS-MS. m/e 526.03 (m + 1) |
| 39 | 32 | 2-methyl-5-nitrophenyl | 1H NMR (DMSO-d6, 400 MHz): δ 8.98 (2H, br), 8.90 (1H, s), 8.76 (1H, t, J = 6.0 Hz), 8.68 (1H, d, J = 2.0 Hz), 8.59 (1H, br), 8.08 (1H, d, J = 1.2 Hz), 8.02 (1H, dd, J1 = 2.4 Hz, J2 = 8.2 Hz), 7.95 (2H, d, J = 7.6 Hz), 7.64 (2H, d, J = 6.8 Hz), 7.52-7.60 (1H, m), 7.43 (1H, d, J = 8.0 Hz), 3.16-3.18 (2H, m), 2.95-3.16 (4H, m), 2.73 (2H, t, J = 8.0 Hz), 2.39 (3H, s), 1.82-1.86 (2H, m)<br>IS-MS, m/e 505.62 (m + 1) |
| 40 | 33 | 2-methyl-4-nitrophenyl | 1H NMR (DMSO-d6, 400 MHz): δ 9.67 (1H, s), 9.03 (2H, br), 8.88 (1H, s), 8.75-8.79 (2H, m), 8.67 (1H, s), 8.56 (1H, d, J = 6.0 Hz), 8.03 (1H, s), 7.98 (1H, dd, J1 = 2.4 Hz, J2 = 8.4 Hz), 7.92 (2H, d, J = 7.2 Hz), 7.57-7.61 2H, m), 7.48-7.51 (1H, m), 7.32-7.39 (1H, m), 3.18-3.19 (2H, m), 2.92-2.97 (4H, m), 2.70 (2H, t, J = 8.0 Hz), 2.36 (3H, s), 1.81-1.85 (2H, m)<br>IS-MS, m/e 504.61 (m + 1) |
| 41 | 34 | 6-chloro-biphenyl-3-yl | 1H NMR (DMSO-d6, 400 MHz): δ 9.62 (1H, s), 8.84 (1H, s), 8.72-8.76 (3H, m), 8.62-8.64 2H, m), 8.48 (1H, d, J = 6.4 Hz), 7.90 (2H, d, J = 7.6 Hz), 7.58 (2H, t, J = 7.6 Hz), 7.39-7.49 (6H, m), 7.20-7.22 (2H, m), 3.10-3.12 (2H, m), 2.95-2.97 (2H, m), 2.84-2.85 (2H, |

| | | | |
|---|---|---|---|
| | | | -continued |
| | | | m), 2.63 (2H, t, J = 8.0 Hz), 1.94-1.86 (2H, m)<br>IS-MS, m/e 557.13 (m + 1) |
| 42 | 65 | 5-nitro-biphenyl-2-yl | ¹H NMR (DMSO-d₆, 400 MHz): δ 9.68 (1H, s), 8.87-8.90 (3H, m), 8.72-8.74 (2H, m), 8.64 (1H, m), 8.55 (1H, d, J = 5.2 Hz), 8.18 (1H, d, J = 8.8 Hz), 7.90-7.93 (3H, m), 7.57-7.61 (3H, m), 7.42-7.48 (5H, m), 7.36 (2H, d, J = 7.6 Hz), 3.09-3.11 (2H, m), 2.87-2.89 (2H, m), 2.71-2.73 (2H, m), 2.66 (2H, t, J = 6.8 Hz), 171-1.74(2H, m)<br>IS-MS, m/e 567.68 (m + 1) |
| 43 | 66 | 5-trifluoromethyl-biphenyl-2-yl | ¹H NMR (DMSO-d₆, 400 MHz): δ 9.64 (1H, s), 8.85 (1H, s), 8.76-8.78 (2H, m), 8.65-8.67 (1H, m), 8.61-8.63 (1H, m), 8.50 (1H, d, J = 5.2 Hz), 7.90 (2H, d, J = 7.6 Hz), 7.69 (1H, d, J = 8.4 Hz), 7.54-7.56 (2H, m), 7.50-7.51 (2H, m), 7.39-7.44 (3H, m), 3.06-3.08 (2H, m), 2.87-2.89 (2H, m), 2.71-2.73 (2H, m), 2.59-2.61 (2h, m), 1.73-1.75 (2H, m)<br>IS-MS, m/e 590.70 (m + 1) |
| 44 | 55 | 4-chloro-2-(N-piperazinyl)phenyl | ¹H NMR (DMSO-d₆, 400 MHz): δ 9.63 (1H, s), 9.10 (2H, br), 8.85 (1H, s), 8.77 (1H, t, J = 5.2 Hz), 8.73 (1H, d, J = 6.0 Hz), 8.64 (1H, s), 8.51 (1H, d, J = 6.4 Hz), 7.92 (2H, d, J = 7.6 Hz), 7.59 (2H, d, J = 8.0 Hz), 7.50 (1H, t, J = 6.8 Hz), 7.21 (1H, d, J = 8.4 Hz), 7.21 (2H, t, J = 8.0 Hz), 3.16-3.23 (6H, m), 2.97-3.00 (6H, m), 2.85-2.87 (2H, m), 2.60 (2H, t, J = 8.0 Hz), 1.84-1.86 (2H, m)<br>IS-MS, m/e 565.15 (m + 1) |
| 45 | 67 | 5-chloro-3'-trifluoromethyl-biphenyl-2-yl | ¹H NMR (DMSO-d₆, 400 MHz): δ 9.61 (1H, s), 8.82 (1H, s), 8.69 (2H, br), 8.68 (2H, s), 8.46 (1H, d, J = 5.2 Hz), 7.90 (2H, d, J = 8.0 Hz), 7.76 (1H, d, J = 8.4 Hz), 7.62-7.68 (2H, m), 7.56-7.58 (2H, m), 7.42-7.50 (2H, m), 7.36 (1H, d, J = 8.0), 7.28 (2H, d, J = 6.8 Hz), 3.05-3.07 (2H, m), 2.86-2.88 (2H, m), 2.69-2.71 (2H, m), 2.51-2.53 (2H, m), 1.65-1.67 (2H, m)<br>IS-MS, m/e 625.13 (m + 1) |
| 46 | 68 | 5-chloro-biphenyl-2-yl | ¹H NMR (DMSO-d₆, 400 MHz): δ 9.64(1H, s), 8.84 (1H, s), 8.75 (2H, br), 8.65 (1H, t, J = 5.6 Hz), 8.62 (1H, s), 8.49 (1H, d, J = 6.4 Hz), 7.91 (2H, d, J = 7.2 Hz), 7.59 (2H, t, J = 7.2 Hz), 7.50 (1H, t, J = 7.2 Hz), 7.39-7.44 (3H, m), 7.19-7.35 (3H, m), 7.18 (1H, d, J = 8.0 Hz), 3.20-3.22 (2H, m), 3.06-3.08 (2H, m), 3.05-3.07 (2H, m), 1.65-1.68 (2H, m)<br>IS-MS, m/e 557.20 (m + 1) |
| 47 | 69 | 5-chloro-3'-nitro-biphenyl-2-yl | ¹H NMR (DMSO-d₆, 400 MHz): δ 9.60 (1H, s), 8.82 (1H, s), 8.71 (1H, br), 8.64 (2H, br), 8.59 (2H, s), 8.45 (1H, d, J = 6.8 Hz), 8.25 (1H, d, J = 8.4 Hz), 8.10 (1H, s), 7.89 (2H, d, J = 7.6 Hz), 7.80 (1H, d, J = 7.6 Hz), 7.73 (1H, t, J = 7.6 Hz), 7.59 (2H, t, J = 7.6 Hz), 7.46-7.50 (2H, m), 7.33-7.39 (2H, m), 3.04-3.05 (2H, m), 2.86-2.88 (2H, m), 2.71-2.73 (2H, m), 2.52-2.54 (2H, m), 1.64-1.66 (2H, m)<br>IS-MS, m/e 602.13 (m + 1) |
| 48 | 35 | 4-chloro-2-fluorophenyl | ¹H NMR (DMSO-d₆, 400 MHz): δ 9.67 (1H, s), 8.85 (1H, s), 8.74 (2H, br), 8.67-8.66 (1H, m), 8.52-8.53 (1H, m), 7.90-7.91 (2H, m), 7.57-7.58 (3H, m), 7.48-7.49 (1H, m), 7.27-7.29 (2H, m), 7.19-7.20 (1H, m), 3.33-3.34 (2H, m), 3.21-3.22 (2H, m), 2.58-2.59 (2H, m), 2.52-2.54 (2H, m), 1.80-1.83 (2H, m)<br>IS-MS, m/e 499.02 (m + 1) |
| 49 | 50 | 4-chloro-2-(4-methyl-piperazin-1-yl)-phenyl | ¹H NMR (DMSO-d₆, 400 MHz): δ 10.55 (1H, s), 9,67 (1H, s), 9.25 (2H, br), 8.83-8.88 (2H, br), 8.74-8.75 (1H, m), 8.67-8.69 (1H, m), 8.56-8.57 (1H, m), 7.93-7.94 (2H, m), 7.51-7.58 (3H, m), 7.12-7.20 (3H, m), 3.39-3.40 (2H, m), 2.97-3.20 (12H, m), 2.83 (3H, s), 2.60-2.61 (2H, m), 1.89-1.90 (2H, m)<br>IS-MS, m/e 579.20 (m + 1) |

| | | -continued | |
|---|---|---|---|
| 50 | 49 | 4-chloro-2-pyrrolidin-1-yl-phenyl | $^1$H NMR (300 MHz, CD$_3$OD) δ 9.77 (s, 1H), 8.94 (d, 1H, J = 1.6 Hz), 8.88 (d, 1H, J = 6.8 Hz), 8.87 (s, 1H), 8.74 (d, 1H, J = 6.8 Hz), 7.93 (d, 2H, J = 7.0 Hz), 7.52-7.64 (m, 3H), 7.40-7.42 (m, 1H), 7.33 (d, 1H, J = 8.0 Hz), 7.22 (s, 1H), 3.52-3.58 (m, 4H), 3.21-3.28 (m, 4H), 3.15 (t, 2H, J = 7.8 Hz), 2.95 (t, 2H, J = 7.8 Hz), 2.22-2.17 (m, 4H), 2.06 (t, 2H, J = 7.8 Hz). ESIMS : m/z 549 (M + H)$^+$. |
| 51 | 56 | 4-chloro-2-morpholin-4-yl-phenyl | $^1$H NMR (CD$_3$OD): δ 10.02 (s, 1H), 9.19 (bd, J = 7.3 Hz, 1H), 9.07 (bd, J = 9.7 Hz, 2H), 8.81 (d, J = 7.3 Hz, 1H), 7.96 (d, J = 7.3 Hz, 2H), 7.54-7.70 (m, 3H), 7.27 (bt, J = 7.3 Hz, 2H), 7.15 (bd, J = 8.1 Hz, 1H), 3.90 (m, 2H), 3.27 (m, 2H), 3.22 (m, 2H), 3.11 (bt, J = 8.0 Hz, 2H), 2.99 (m, 4H), 2.83 (t, J = 7.7 Hz, 2H), 2.09 (m, 2H). ESIMS: m/z 565 [M + H]$^+$. |
| 52 | 57 | 4-chloro-2-(1,1-dioxo-thiomorpholin-4-yl)-phenyl | $^1$H NMR (300 MHz, CD$_3$OD) δ 9.96 (s, 1H), 9.16 (d, 1H, J = 7.0 Hz), 9.09 (s, 1H), 9.04 (s, 1H), 8.82 (d, 1H, J = 7.0 Hz), 7.96 (d, 2H, J = 7.2 Hz), 7.52-7.62 (m, 3H), 7.28-7.35 (m, 2H), 7.15 (dd, 1H, J = 8.1, 1.6 Hz), 3.38-3.46 (m, 10 Hz), 3.28 (t, 2H, J = 7.6 Hz), 3.18 (t, 2H, J = 7.6 Hz), 2.82 (t, 2H, J = 7.6 Hz), 2.11 (q, 2H, J = 7.6 Hz). ESIMS: m/z 613 (M + H)$^+$. |
| 53 | 70 | 4-chloro-2-piperidin-4-yl-phenyl | $^1$H NMR (CD$_3$OD): δ 9.92 (bs, 1H), 8.95-9.12 (m, 3H), 8.78 (bd, J = 7.0 Hz, 1H), 7.95 (bd, J = 8.0 Hz, 2H), 7.52-7.67 (m, 3H), 7.17-7.30 (m, 3H), 3.44-3.55 (m, 3H), 3.31-3.41 (m, 3H), 3.14-3.27 (m, 5H), 2.82 (bt, J = 8.2 Hz, 2H), 1.83-2.06 (m, 6H). ESIMS: m/z 563 [M + H]$^+$. |
| 54 | 58 | 4-chloro-2-(3-methyl-piperazin-1-yl)-phenyl | $^1$H NMR (CD$_3$OD): δ 9.93 (bs, 1H), 8.96-9.12 (m, 3H), 8.78 (bd, J = 6.7 Hz, 1H), 7.95 (bd, J = 7.6 Hz, 2H), 7.52-7.67 (m, 3H), 7.28 (d, J = 8.3 Hz, 1H), 7.23 (d, J = 1.9 Hz, 1H), 7.17 (dd, J = 1.9 and 8.3 Hz, 1H), 3.71 (m, 1H), 3.43-3.52 (m, 2H), 2.97-3.28 (m, 9H), 2.75-2.88 (m, 3H), 2.00-2.13 (m, 2H), 1.38 (d, J = 6.7 Hz, 3H). ESIMS: m/z 578 [M + H]$^+$. |
| 55 | 59 | 4-chloro-2-(1-methyl-pyrrolidin-3-yloxy)-phenyl | $^1$H NMR (CD$_3$OD): δ 9.98 (bs, 1H), 9.15 (bd, J = 7.0 Hz, 1H), 9.08 (dd, J = 1.6 and 7.0 Hz, 1H), 9.02 (bs, 1H), 8.80 (bd, J = 6.7 Hz, 1H), 7.93-8.01 (m, 2H), 7.53-7.67 (m, 3H), 7.19 (d, J = 7.8 Hz, 1H), 6.94-7.02 (m, 2H), 5.19-5.31 (m, 1H), 3.76-4.17 (m, 2H), 3.41-3.56 (m, 2H), 3.17-3.25 (m, 3H), 3.06-3.16 (m, 3H), 2.99 (s, 3H), 2.65-2.85 (m, 3H), 2.23-2.50 (m, 1H), 2.03 (quint, J = 7.4 Hz, 2H). ESIMS: m/z 579 [M + H]$^+$. |
| 56 | 60 | 4-chloro-2-(pyrrolidin-3-yloxy)-phenyl | $^1$H NMR (300 MHz, CD$_3$OD) δ 9.96 (s, 1H), 9.12 (d, 1H, J 6.5 Hz), 9.06 (d, 1H, J = 1.6 Hz), 9.01 (s, 1H), 8.79 (d, 1H, J = 6.5 Hz), 7.97 (d, 2H, J = 7.3 hz), 7.56-7.65 (m, 3H), 7.19 (d, 1H, J = 8.1 Hz), 7.04 (d, 1H, J = 1.6 Hz), 6.97 (dd, 1H, J = 8.1, 1.6 Hz), 5.24-5.28 (m, 1H), 3.48-3.70 (m, 4H), 3.29 (t, 2H, j = 7.3 Hz), 3.20 (t, 2H, J = 7.2 Hz), 3.10 (t, 2H, J = 7.3 Hz), 2.66-2.78 (m, 2H), 2.36 (t, 2H, J = 7.3 Hz), 2.01 (q, 2H, J = 7.3 Hz). ESIMS : m/z 565 (M + H)$^+$. |
| 57 | 71 | 2-(1-acetyl-piperidin-4-yl)-4-chloro-phenyl | $^1$H NMR (CD$_3$OD): δ 10.00 (bs, 1H), 9.12-9.22 (m, 1H), 8.98-9.10 (m, 2H), 8.80 (bs, 1H), 7.88-7.99 (m, 2H), 7.51-7.68 (m, 3H), 7.09-7.27 (m, 3H), 4.59-4.73 (m, 1H), 3.97-4.11 (m, 1H), 3.01-3.32 (m, 8H), 2.70-2.90 (m, 3H), 2.15 (s, 3H), 1.91-2.07 (m, 2H), 1.51-1.89 (m, 4H). ESIMS: m/z 605 [M + H]$^+$. |
| 58 | 48 | 2-(2-hydroxy-ethyl)-4-nitro-phenyl | $^1$H NMR (300 MHz, CD$_3$OD) δ 9.94 (s, 1H), 9.08 (s, 1H), 9.00-9.04 (m, 2H), 8.79 (s, 1H), 8.14 (s, 1H), 8.03 (d, 1H, J = 8.0 Hz), 7.93 (d, 2H, J = 7.3 Hz), 7.55-7.65 (m, 3H), 7.46 (d, 1H, J = 8.0 Hz), 3.83 (t, 2H, J = 5.6 Hz), 3.17-3.32 (m, 6H), 2.98 (t, 2H, J = 5.6 Hz), |

| | | | |
|---|---|---|---|
| | | | -continued |
| | | | 2.90 (t, 2H, J = 7.2 Hz), 2.05 (q, 2H, J = 7.2 Hz).<br>ESIMS m/z 535 (M + H)+. |
| 59 | 61 | 4-chloro-2-(2-dimethylamino-ethoxy)-phenyl | $^1$H NMR (CD$_3$OD): δ 9.38 (br. s, 1H), 8.7 (m, 2H), 8.42 (d, J = 5.6 Hz, 1H), 8.35 (br. s, 1H), 7.74 (d, J = 7.2 Hz, 2H), 7.5 (m, 3H), 6.94 (d, J = 7.7 Hz, 1H), 6.82 (m, 2H), 4.0 (t, J = 5.7 Hz, 2H), 3.47 (s, 6H), 2.98 (t, J = 5.7 Hz, 2H) 2.73 (m, 4H), 2.6 (m, 2H), 2.48 (m, 2H), 2.3 (m, 2H).<br>MS m/z 567.2 (M + H)+. |
| 61 | 36 | 4-nitro-2-trifluoromethylphenyl | $^1$H NMR (DMSO-d$_6$, 400 MHz): δ 9.03 (2H, br), 8.89 (1H, s), 8.76 (1H, t, J = 6.0 Hz), 8.67 (1H, d, J = 1.6 Hz), 8.58 (1H, m), 8.51 (1H, dd, J$_1$ = 2.0 Hz, J$_2$ = 8.4 Hz), 8.42 (1H, d, J = 2.0 Hz), 7.95 (2H, d, J = 7.6 Hz), 7.83 (1H, d, J = 8.8 Hz), 7.64 (2H, t, J = 6.0 Hz), 7.54 (1H, t, J = 6.8 Hz), 3.18-3.19 (2H, m), 3.01-3.16 (4H, m), 2.92 (2H, t, J = 8.0 Hz), 1.91-1.93 (2H, m)<br>IS-MS, m/e 559.60 (m + 1) |
| 62 | 37 | 2-carbomethoxyl-4-nitrophenyl | $^1$H NMR (DMSO-d$_6$, 400 MHz): δ 9.68 (1H, s), 8.92 (2H, br), 8.88 (1H, s), 8.77 (1H, s), 8.73 (1H, t, J = 6.0 Hz), 8.67 (1H, d, J = 1.6 Hz), 8.58 (1H, d, J = 2.4 Hz), 8.55 (1H, d, J = 6.0 Hz), 8.39 (1H, dd, J$_1$ = 2.0 Hz, J$_2$ = 8.0 Hz), 7.95 (2H, d, J = 7.6 Hz), 8.68 (1H, d, J = 8.4 Hz), 7.62 (2H, d, J = 7.6 Hz), 7.54 (1H, t, J = 8.0 Hz), 3.91 (3H, s), 3.15-3.18 (2H, m), 2.94-3.06(4H, m), 1.88-1.90 (2H, m)<br>IS-MS, m/e 549.62 (m + 1) |
| 63 | 38 | 2-methoxy-4-nitrophenyl | $^1$H NMR (DMSO-d$_6$, 400 MHz): δ 9.73 (1H, s), 8.98 (2H, br), 8.92 (1H, s), 8.79-8.81 (1H, m), 8.69 (1H, d, J = 7.2 Hz), 8.61 (1H, d, J = 5.6 Hz), 7.96 (2H, d, J = 7.6 Hz), 7.81-7.84 (2H, m), 7.51-7.79 (4H, m), 7.46 (1H, d, J = 8.4 Hz), 3.93 (3H, s), 3.18-3.20 (2H, m), 2.98-3.00(2H, m), 2.70 (2H, t, J = 7.6 Hz), 1.85-1.88 (2H, m)<br>IS-MS, m/e 521.60 (m + 1) |
| 64 | 39 | 2-carboxy-4-nitrophenyl | $^1$H NMR (DMSO-d$_6$, 400 MHz): δ 8.88 (1H, s), 8.71 (2H, br), 8.68-8.70 (1H, m), 8.66 (1H, s), 8.59 (1H, d, J = 2.4 Hz), 8.54-8.56 (1H, m), 8.36 (1H, dd, J1 = 2.4 Hz, J2 = 8.6 Hz), 7.94 (2H, d, J 8.4 Hz), 7.60-7.65 (3H, m), 7.53-7.55 (1H, m), 3.13-3.15 (2H, m), 3.08 (2H, t, J = 7.6 Hz), 2.99-3.01 (2H, m), 2.92-2.94 (2H, m), 1.87-1.89 (2H, m)<br>IS-MS, m/e 535.60 (m + 1) |
| 65 | 40 | 2,4-dichlorophenyl | $^1$H NMR (CD$_3$OD): δ 9.98 (s, 1H), 9.14 (d, J = 7.3 Hz, 1H), 9.05 (s, 1H), 9.03 (s, 1H), 8.79 (d, J = 7.3 Hz, 1H), 7.95 (d, J = 7.3 Hz, 2H), 7.52-7.67 (m, 3H), 7.45 (d, J = 1.6 Hz, 1H), 7.35 (d, J = 8.9 Hz, 1H), 7.29 (dd, J = 1.6 and 8.9 Hz, 1H), 3.18-3.28 (m, 4H), 3.11 (bt, J = 8.1 Hz, 2H), 2.85 (t, J = 7.7 Hz, 2H), 2.04 (quint, J = 8.1 Hz, 2H).<br>ESIMS: m/z 512 [(M + H)+, $^{35}$Cl], 514 [(M + H)+, $^{37}$Cl]. |
| 66 | 41 | 2,3-dichlorophenyl | $^1$H NMR (300 MHz, CD$_3$OD) δ 9.98 (s, 1H), 9.13 (d, 1H, J = 7.0 Hz), 9.05 (d, J = 1.7 Hz), 9.02 (s, 1H), 8.79 (d, 1H, J = 7.0 Hz), 7.95 (d, 2H, J = 7.6 Hz), 7.56-7.65 (m, 3H), 7.42 (dd, 1H, J = 7.5, 1.7 Hz), 7.31 (dd, 1H, J = 1.7, 8.1 Hz), 7.26 (dd, 1H, J = 7.5, 8.1 Hz), 3.21-3.27 (m, 4H), 3.13 (t, 2H, J = 7.6 Hz), 2.92 (t, 2H, J = 7.6 Hz), 2.06 (q, 2H, J = 7.6 Hz).<br>ESIMS : m/z 514 (m + H)+. |
| 67 | 42 | 4-cyano-3-trifluoromethylphenyl | $^1$H NMR (300 MHz, CD$_3$OD) δ 9.96 (s, 1H), 9.11 (d, 1H, J = 7.3 Hz), 9.04 (d, 1H, J = 1.6 Hz), 9.01 (s, 1H), 8.79 (d, 1H, J = 7.3 Hz), 7.93-7.96 (m, 3H), 7.85 (s, 1H), 7.73 (d, 1H, J = 8.1 Hz), 7.56-7.65 (m, 3H), 3.18-3.27 (m, 4H), 3.11 (t, 2H, J = 8.0 Hz), 2.92 (t, 2H, J = 8.0 Hz), 2.09 (quin, 2H, J = 8.0 Hz)<br>ESIMS: m/z 539 (M + H)+. |

| 68 | 43 | 2,3-difluorophenyl | $^1$H NMR (CD$_3$OD): δ 9.97 (m, 1H), 9.08-9.18 (m, 1H), 8.98-9.07 (m, 2H), 8.79 (bd, J = 7.0 Hz, 1H), 7.91-7.98 (m, 2H), 7.52-7.68 (m, 3H), 7.06-7.21 (m, 3H), 3.16-3.28 (m, 4H), 3.11 (bt, J = 8.1 Hz, ZN), 2.83 (t, J = 7.9 Hz, 2H), 2.05 (quint, J = 7.9 Hz, 2H). ESIMS: m/ 482 [M + H $^+$. |
| 69 | 63 | 4-chloro-2-(2-morpholin-4-yl-ethoxy)-phenyl | $^1$H-NMR (CD$_3$OD): δ 9.96 (bs, 1H), 9.11 (d, 1H, J = 5.2 Hz), 9.06 (d, 1H, J = 1.7 Hz), 8.99 (bs, 1H), 8.81 bs, 1H), 7.93-7.98 (m, 2H), 7.53-7.65 (m, 3H), 7.19 (d, 1H, J = 8.1 Hz), 7.08 (d, 1H, J = 1.7 Hz), 6.98 (dd, 1H, J$_1$ = 8.1 Hz, J$_2$ = 1.7 Hz), 4.46 (t, 2H, J = 4.6 Hz), 4.01-4.10 (m, 2H), 3.86-3.94 (m, 2H), 3.78 (d, 1H, J = 5.2 Hz), 3.74 (d, 1H, J = 4.6 Hz), 3.60-3.64 (m, 2H), 3.26-3.42 (m, 4H), 3.20-3.22 (m, 2H), 3.09-3.15 (m, 2 H), 2.77 (t, 2H, J = 7.5 Hz), 1.98 (m, 2H). MS (ESI+): m/z 609.2 [M + H]. |
| 70 | 44 | 2,4-difluorophenyl | $^1$H NMR (CD$_3$OD): δ 9.94 (br. s, 1H), 9.08 (d, J = 6.86 Hz, 1H), 9.02 (d, J = 2.01 Hz, 1H), 8.99 (d, J = 1.62 Hz, 1H), 8.78 (d, J = 6.86 Hz, 1H), 7.94 (m, 2H), 7.6 (m, 3H), 7.33 (m, 1H), 6.93 (m, 2H), 3.22 (m, 4H), 3.09 (m, 2H), 7.96 (d, J = 7.40 Hz, 2H), 7.92 (m, 2H), 7.62 (m, 3H), 7.45 (d, J = 8.24 Hz, 2H), 7.17 (d, J = 8.25 Hz, 2H), 3.26 (m, 4H), 3.08 (m, 2H), 2.75 (t, J = 7.77 Hz, 2H), 2.01 (m, 2H). MS m/z 482.1 (M + H)$^+$. |
| 71 | 45 | 4-(pyrrolidine-1-sulfonyl)-phenyl | $^1$H NMR (DM50): δ 9.69(s, 1H), 8.94-8.64 (M, 6H), 8.53 (d, J = 4.0 Hz, 1H), 7.95 (dt, J$_1$ = 1.4 Hz, J$_2$ = 7.1 Hz, 2H), 7.75 (dt, J$_1$ = 1.7 Hz, J$_2$ = 8.3 Hz, 2H), 7.63 (tt, J$_1$ = 1.8 Hz, J$_2$ = 7.6 Hz, 2H), 7.54 (tt, J$_1$ = 1.8 Hz, J$_2$ = 7.6 Hz, 1H), 7.50 (d, J = 8.4 Hz, 2H), 3.22-3.09 (m, 6H), 3.06-2.86 (m, 4H), 2.74 (t, J = 7.6 Hz, 2H), 1.91 (p, J = 7.6 Hz, 2H), 1.68-1.61 (m, 4H). LCMS: m/z 579 (M + H)$^+$ 577(M − H)$^−$ |

Example 72

7-Phenyl-isoquinoline-5-sulfonic acid [2-(3-(4-aminophenyl)-propylamino)-ethyl]-amide salt dihydrochloride

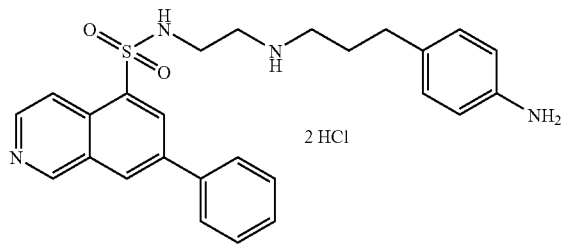

2 HCl

Add 7-Phenyl-isoquinoline-5-sulfonic acid [2-(3-(4-nitrophenyl)-propylamino)-ethyl]-amide (Example 3, 0.2 g, 0.4 mmol) to a solution of di-tert-butyl dicarbonate (0.13 g, 0.8 mmol) and DMAP (0.005 g, 0.04 mmol) in acetonitrile (1.4 mL). After completion of reaction (TLC) evaporate the solution and purify the residue by silica gel chromatography eluting with ethyl acetate-hexanes to afford the bis-carbamate. ESIMS: m/z 287 (M+H)$^+$. Reduce the bis-carbamate (0.124 g) in ethanol (50 mL) with 5% palladium on carbon (0.02 g) under a hydrogen atmosphere (60 lbs) overnight. Filter and evaporate the reaction, load the residue onto a cation exchange resin (10 g), wash with methanol, then elute the product with 2M methanolic ammonia. After evaporation, treat the residue with a solution of hydrochloric acid (4M) in dioxane for 2 hours at room temperature. Evaporate the reaction, and purify the residue by preparative HPLC to afford the title compound (0.01 g). $^1$H NMR (DMSO): δ9.61 (s, 1H), 8.84 (d, J=1.5 Hz, 1H), 8.76(d, J=6.1 Hz, 3H), 8.63(d, J=1.5 Hz, 1H), 8.60(t, J=6.1 Hz, 1H), 8.47(d, J=5.7 Hz, 1H), 7.94(d of t, J1=1.3 Hz, J2=7.3 Hz, 2H), 7.63 (tt, J1-1.7 Hz, J2=7.3 Hz, 2H), 7.54(tt, J1=1.3 Hz, J2=7.5 Hz, 1H), 7.28-7.13 (m, 3H), 3.74 (bs, 2H), 3.14 (q, J=6.0 Hz, 2H). 3.00(p, J=5.3 Hz, 2H), 2.94-2.84(m, 2H) 2.61(t, J=7.5 Hz, 2H) 1.85(p, J=7.5 Hz, 2H). LCMS: m/z 461 (M+H)$^+$, 459(M−H).

Example 73

7-Phenyl-isoquinoline-5-sulfonic acid [2-(3-hydroxy-3-(4-nitrophenyl)-propylamino)-ethyl]-amide diyhrochloride

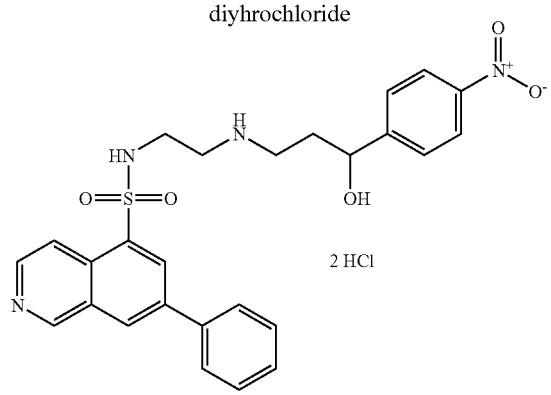

2 HCl

Add 1-(4-nitrophenyl)propenone (46 mg, 0.26 mmol) to a slurry of 7-phenyl-isoquinoline-5-sulfonic acid (2-aminoethyl)-amide (100 mg, 0.25 mmol) and triethyl amine (0.035 mL, 0.25 mmol) in 1:1 THF:methanol (4 mL). After 30 min, add a large excess of sodium borohydride. Stir 30 min, apply to a cation exchange resin (10 g), wash with methanol (50 mL), and elute product from resin with 2M methanolic ammonia (50 mL). Chromatograph the residue on a silica gel cartridge (11 g), eluting with a dichloromethane-methanol gradient to afford the freebase of the title compound (25 mg, 20%). The free base is slurried with aqueous HCl and lyophilized to provide HCl salt of title compound. $^1$H NMR (DMSO-d$_6$): δ9.62 (s, 1H), 8.83 (d, J=2.0 Hz, 1H), 8.72 (d, J=5.9 Hz, 1H), 8.66-8.61 (m, 2H), 8.48 (d, J=6.6 Hz, 1H), 8.19 (d, J=9.0 Hz, 2H), 7.90 (d, J=8.6 Hz, 2H), 7.62-7.56 (m, 4H), 7.50 (tt, J=7.5, 1.2 Hz, 1H), 4.81 (dd, J=8.6, 4.1 Hz, 1H), 3.12 (q, J=6.6 Hz, 2H), 3.01-2.92 (m, 4H), 1.99-1.89 (m, 1H), 1.89-1.77 (m, 1H). ESIMS: m/z 507 (M+H)$^+$.

Example 74

7-Phenyl-isoquinoline-5-sulfonic acid [2-(3-hydroxy-3-(4-fluorophenyl)-propylamino)-ethyl]-amide

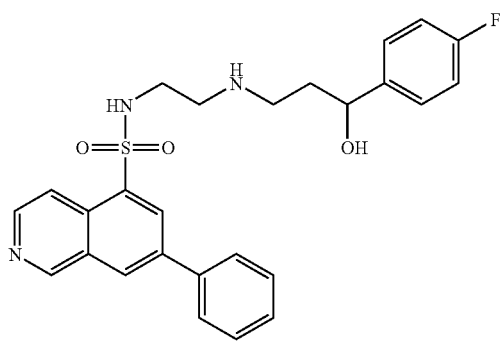

Add 1-(4-fluorophenyl)propenone (61 mg, 0.40 mmol) to a solution of isoquinoline-5-sulfonic acid (2-{[bis-(4-methoxy-phenyl)-methyl]-amino}-ethyl)-amide (150 mg, 0.27 mmol) in THF (0.27 mL). Stir at room temperature for 20 hours, dilute with THF (1 mL) and methanol (2 mL), and add sodium borohydride (10 mg, 0.27 mmol). After 10 minutes, apply the reaction to 10 g of cation exchange resin, wash with methanol (50 mL), and elute product from resin with 2M methanolic ammonia (50 mL). Evaporate, and chromatograph the residue using a methanol-dichloromethane gradient. Dissolve a portion of the resulting material in dichloromethane (5 mL) containing trifluoroacetic acid (0.07 mL), and add 5 equivalents of thiophenol scavenger resin. After 2 hours, filter and evaporate, and chromatograph the residue using a methanol-dichloromethane gradient to provide the title compound. $^1$H NMR (DMSO-d$_6$): δ9.57 (s, 1H), 8.80 (d, J=1.8 Hz, 1H), 8.72 (d, J=6.2 Hz, 1H), 8.60 (d, J=1.8 Hz, 1H), 8.45 (d, J=6.2 Hz, 1H), 7.90 (d, J=7.0 Hz, 2H), 7.62 (t, J=7.0 Hz, 2H), 7.52 (t, J=7.6 Hz, 1H), 7.30 (dd, J=8.9, 5.7 Hz, 2H), 7.11 (t, J=8.3 Hz, 2H), 4.57 (t, J=5.7 Hz, 1H), 2.99 (t, J=6.7 Hz, 2H), 2.72-2.54 (m, 4H), 1.67-1.56 (m, 2H). ESIMS: m/z 480 (M+H)$^+$.

Example 75

7-Phenyl-isoquinoline-5-sulfonic acid [2-(3-hydroxy-3-(4-cyanophenyl)-propylamino)-ethyl]-amide, dihydrochloride salt

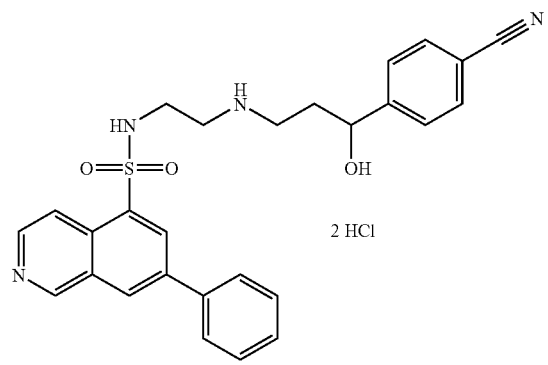

Prepare the free base of the title compound according to example 74 substituting 1-(4-cyanophenyl)propenone for 1-(4-fluorophenyl)propenone. Dissolve in aqueous hydrochloric acid and lyophylize to afford the title salt. $^1$H NMR (DMSO): δ9.70 (s, 1H), 8.99-8.85 (m, 3H), 8.79(d, J=5.2 Hz, 1H), 8.73(t, J=5.2 Hz, 1H), 8.68(d, J=1.3 Hz, 1H), 8.57(d, J=5.9 Hz, 1H), 7.95(d of t, J1=1.9 Hz, J2=7.3 Hz, 2H), 7.83(d of t J1=1.9 Hz, J2=8.7 Hz, 2H), 7.63 (tt, J1-1.7 Hz, J2=7.3 Hz, 2H), 7.55(tt, J1=3.3 Hz, J2=8.0 Hz, 3H), 4.79(dd, J1=3.8 Hz, J2=8.6 Hz, 1H), 3.17(q, J=6.0 Hz, 2H). 3.00(sep, J=6.0 Hz, 4H), 2.01-1.77(m, 2H). LCMS: m/z 487 (M+H)$^+$, 485(M−H)$^-$.

Example 76

7-Phenyl-isoquinoline-5-sulfonic acid [2-(3-hydroxy-3-phenyl-propylamino)-ethyl]-amide

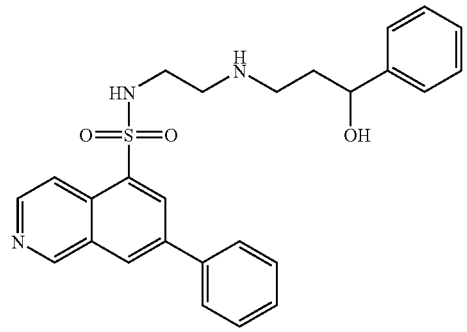

Prepare the title compound according to example 74 substituting 1-phenylpropenone for 1-(4-fluorophenyl)propenone. $^1$H NMR (DMSO-d$_6$): δ9.57 (s, 1H), 8.80 (d, J=1.3 Hz, 1H), 8.72 (d, J=6.1 Hz, 1H), 8.60 (d, J=1.6 Hz, 1H), 8.45 (d, J=6.1 Hz, 1H), 7.90 (d, J=7.9 Hz, 2H), 7.62 (t, J=7.3 Hz, 2H), 7.52 (t, J=6.7 Hz, 1H), 7.34-7.20 (m, 5H), 4.57 (t, J=6.4 Hz, 1H), 2.99 (t, J=6.4 Hz, 2H), 2.71-2.55 (m, 4H), 1.68-1.60 (m, 2H). ESIMS: m/z 462 (M+H)$^+$.

Example 77

7-Phenyl-isoquinoline-5-sulfonic acid [2-(3-hydroxy-3-(3-nitrophenyl)-propylamino)-ethyl]-amide, dihydrochloride salt

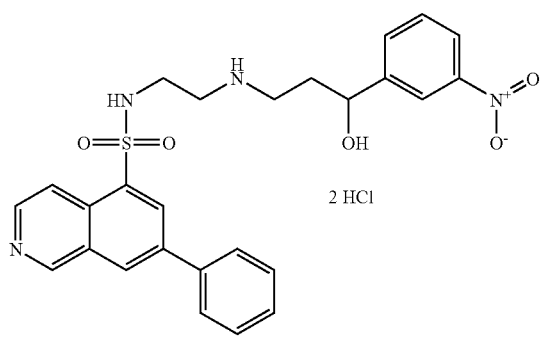

Prepare the title compound according to example 75 substituting 1-(3-nitrophenyl)-propenone for 1-(4-fluorophenyl) propenone. $^1$H NMR (DMSO): δ9.64(s, 1H), 8.98-8.81 (m, 3H), 8.75-(d, J=6.1 Hz, 1H), 8.70(t, J=5.8 Hz, 1H), 8.65(d, J=1.7 Hz, 2H), 8.52(d, J=5.5 Hz, 1H), 8.20(bs, 1H), 8.16-8.10 (m, 1H), 7.94(d, J=7.6 Hz, 1H), 7.80 (d, J=7.6 Hz, 1H), 7.69-7.58 (m, 3H), 7.55-7.49(m, 1H), 4.86(dd, J1=3.8 Hz, J2=8.4 Hz, 1H), 3.22-3.09(m, 2H), 3.08-2.92-(m, 4H), 2.07-1.81(m, 2H), LCMS: m/z 507(M+H)$^+$, 505(M−H)$^−$.

Example 78

(R)-7-Phenyl-isoquinoline-5-sulfonic acid [2-(3-hydroxy-3-phenyl-propylamino)-ethyl]-amide, dihydrochloride salt

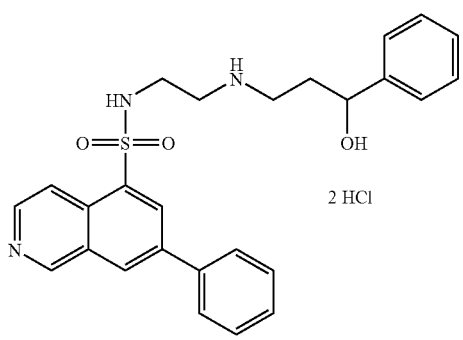

Add sodium iodide (4.29 g, 29 mmol) to a solution of (R)-(+)-3-chloro-1-phenyl-1-propanol (0.5 g, 2.93 mmol) in acetone (9.75 mL), and heat to reflux overnight. Cool and filter the suspension, then remove the volatiles under reduced pressure. Resuspend the residue in ether, filter and evaporate to afford (R)-3-iodo-1-phenyl-1-propanol (0.71 g). Add (R)-3-iodo-1-phenyl-1-propanol (0.1 g, 0.4 mmol) to a solution of 7-phenyl-isoquinoline -5-sulfonic acid (2-amino-ethyl)-amide (0.087 g, 0.27 mmol) in DMF (0.5 mL) and DCE (0.27 mL) containing diisopropylethylamine (0.094 mL, 0.53 mmol), and warm to 80° C. for 30 minutes. Cool to ambient temperature, and apply to a cation exchange resin cartridge. Wash with methanol, and elute product from the resin with 2M methanolic ammonia. Evaporate and purify the residue by silica gel chromatography using a methanol-methylene chloride gradient, followed by treatment with aqueous hydrochloric acid and lyophylization to afford the title compound. $^1$H NMR (DMSO): δ9.71(s, 1H), 9.00-8.82 (m, 3H), 8.80-8.73(m, 2H), 8.69 (d, J=1.8 Hz, 1H), 8.59 (d, J=6.2 Hz, 1H), 7.95 (dd, J1=1.5 Hz, J2=8.5 Hz, 2H), 7.62 (t, J=6.7 Hz, 2H), 7.53 (t, J=7.8 Hz, 1H), 7.38-7.29 (m, 4H), 7.28-7.21 (m, 1H), 5.50-4.67 (bs, 2H), 4.65 (dd, J1=4.5 Hz, J2=8.5 Hz, 1H), 3.23-3.10 (m, 2H), 3.06-2.86 (m, 4H), 2.00=−1.77(m, 2H). LCMS: m/z 462(M+H)$^+$460(M−H)$^−$.

Example 79

7-Phenyl-isoquinoline-5-sulfonic acid [2-(3-hydroxy-3-(4-methanesulfonyl-phenyl)-propylamino)-ethyl]-amide, dihydrochloride salt

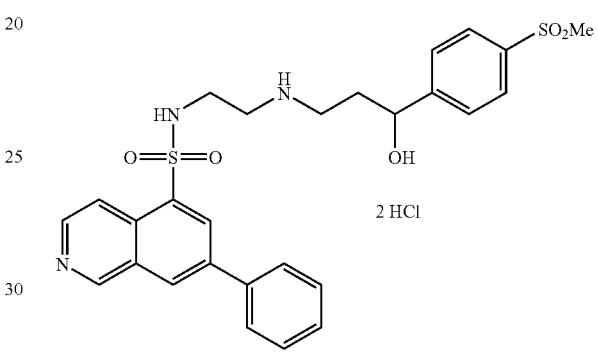

Prepare the title compound according to example 78 substituting 3-chloro-1-(4-methanesulfonyl-phenyl)-1-propanol for (R)-(+)-3-chloro-1-phenyl-1-propanol. $^1$H NMR (DMSO): δ9.69(s, 1H), 9.01-8.83(m, 3H), 8.78 (d, J=6.0 Hz, 1H), 8.73(t, J=5.6 Hz, 1H), 8.68 (d, J=1.7 Hz, 1H), 7.99-7.90 (m, 4H), 7.66-7.60 (m, 4H), 7.54 (tt, J1=2.0 Hz, J2=7.3 Hz, 1H), 5.30-4.30 (m, 3H), 3.22 (s, 3H), 3.22-3.12 (m, 2H), 3.08-2.96 (m, 4H), 2.04-1.80 (m, 2H). LCMS: m/z 540(M+H)$^+$538(M−H)$^−$.

Example 80

7-Phenyl-isoquinoline-5-sulfonic acid [2-(3-hydroxy-3-(4-trifluoromethanesulfonyl-phenyl)-propylamino)-ethyl]-amide, dihydrochloride salt

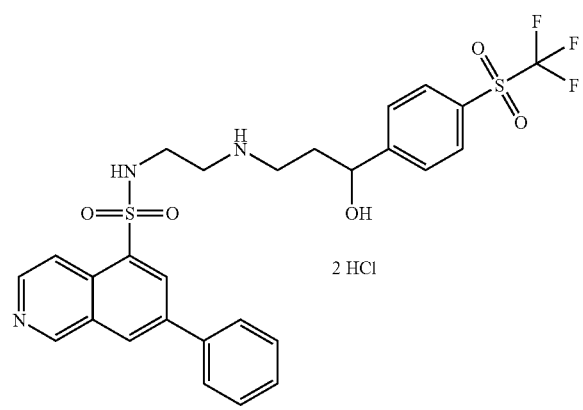

Prepare the title compound according to example 78 substituting 3-chloro-1-(4-trifluoromethanesulfonyl-phenyl)-1-propanol for (R)-(+)-3-chloro-1-phenyl-1-propanol. ¹H NMR (DMSO): δ9.63(s, 1H), 8.87-8.56 (m, 6H), 8.47 (d, J=5.8 Hz, 1H), 8.16 (d, J=8.1 Hz, 2H), 7.94 (dt J1=1.3 Hz, J2=7.0 Hz, 2H), 7.82 (d, J=8.4 Hz, 2H), 7.63 (tt, J1=1.7 Hz, J2=7.5 Hz, 2H), 7.53 (tt, J1=1.3 Hz, J2=7.2 Hz, 1H), 5.97 (bs, 1H), 4.90 (dd, J1=3.5 Hz, J2=8.3 Hz, 1H), 3.17-2.96 (m, 6H), 2.06-1.79 (m, 2H). LCMS: m/z 594(M+H)⁺592(M–H)⁻

Example 81

(R)-7-Phenyl-isoquinoline-5-sulfonic acid [2-(3-hydroxy-3-(4-nitrophenyl)-propylamino)-ethyl]-amide, mesylate salt

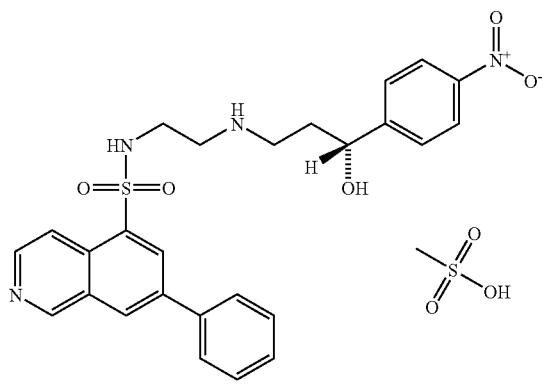

Prepare the free base of the title compound according to example 78 substituting 1-(R)-3-chloro-1-(4-nitrophenyl)-1-propanol for (R)-(+)-3-chloro-1-phenyl-1-propanol. Dissolve in absolute ethanol, and add 1M methanesulfonic acid in ethanol (1 equiv) with stirring to provide a suspension of the salt. Warm the solution to reflux, and add water dropwise to achieve complete dissolution. Chill to 0° C., filter, wash with absolute ethanol, and dry under reduced pressure to afford the title salt. ¹H NMR (DMSO): δ 9.60(S, 1H), 8.83 (d, J=1.5 Hz, 1H), 8.75(d, J=6.0 Hz, 1H), 8.60 (d, J=2.0 Hz, 1H), 8.47 (t, J=5.6 Hz, 1H), 8.43 (d, J=5.9 Hz, 1H), 8.45-8.32 (m, 2H), 8.24 (dt, J=8.7, 2.3 Hz, 2H), 7.90(d, J=7.3 Hz, 2H), 7.65-7.60 (m, 4H), 7.53 (tt, J=7.3, 1.5 Hz, 1H), 5.93 (bs, 1H), 4.86-4.81 (m, 1H), 3.13-2.98 (m, 6H), 2.35 (s, 3H), 2.00-1.80 (m, 2H). LCMS: m/z 507(M+H)⁺505(M–H)⁻.

Example 82

(S)-7-Phenyl-isoquinoline-5-sulfonic acid [2-(3-hydroxy-3-(4-nitrophenyl)-propylamino)-ethyl]-amide, mesylate salt

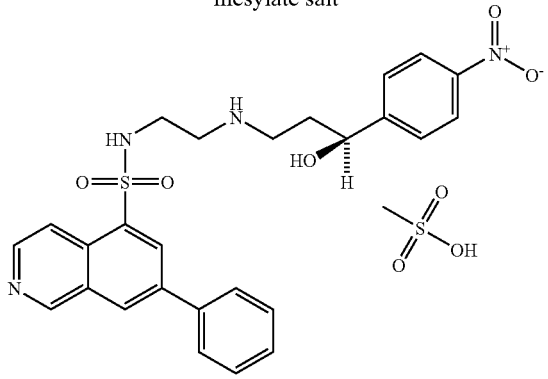

Prepare the title compound according to example 81 substituting 1-(S)-3-chloro-1-(4-nitrophenyl)-1-propanol for (R)-(+)-3-chloro-1-phenyl-1-propanol. ¹H NMR (DMSO): δ9.60(S, 1H), 8.34 (d, J=1.3 Hz, 1H), 8.76(d, J=6.3 Hz, 1H), 8.55-8.30 (m, 4H), 8.25 (t of d, J1=1.8 J2=9.0 Hz, 2H), 7.93(d, J=1.3 Hz, 1H), 7.91 (s, 1H), 7.66-7.60 (m, 4H), 7.54 (tt, J1=1.3 Hz, J2=7.3 Hz, 1H), 5.93 (bs, 1H), 4.83 (dd, J1=3.8 Hz, J2=8.3 Hz, 1H), 3.16-2.94 (m, 6H), 2.32 (s, 3H), 2.01-1.78 (m, 2H). LCMS: m/z 507(M+H)⁺505(M–H)⁻.

Example 83

(±)-7-Phenyl-isoquinoline-5-sulfonic acid [2-(2-hydroxy-3-(4-nitrophenyl)-propylamino)-ethyl]-amide dihydrochloride

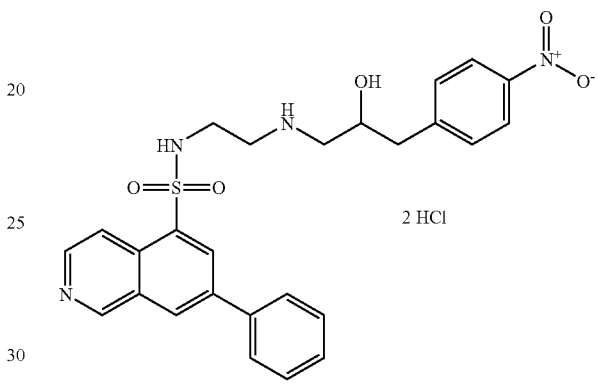

Reflux a solution of 7-Phenyl-isoquinoline-5-sulfonic acid (2-amino-ethyl)-amide (272 mg, 0.83 mmol as free base) and 2-(4-nitro-benzyl)-oxirane (149 mg, 0.83 mmol) in 10 ml of EtOH for 48 hours. Cool to room temperature, evaporate the solvent under reduced pressure, and purify the crude by flash chromatography (CH₂Cl₂-MeOH (3%)) affording the title compound (48%) as free base. Form the hydrochloride salt by treating a dicloromethane solution of the free base with 5 equivalents of HCl (2M in ether) during 1 hour at room temperature and evaporating the solvent in vacuo (99%). ¹H NMR (CD₃OD): δ9.97 (s, 1H), 9.12 (d, J=7.0 Hz, 1H), 9.04 (d, J=8.1 Hz, 1H), 9.03 (s, 1H), 8.78 (d, J=6.97 Hz, 1H), 8.18 (d, J=8.7 Hz, 2H), 7.94 (d, J=7.0 Hz, 2H), 7.6 (m, 6H), 4.2 (m, 1H), 3.25 (m, 5H), 2.95 (m, 3H). MS m/z 507.2 (M+H)⁺.

Example 84

7-Phenyl-isoquinoline-5-sulfonic acid [2-(2-hydroxy-3-phenyl-propylamino)-ethyl]-amide, dihydrochloride salt Prepare the title compound according to example 83 substituting 2-(4-nitrobenzyl)-oxirane for 2-benzyloxirane. ¹H NMR (DMSO-d₆, 400 MHz): 9.63 (1H, s), 8.85 (1H, s), 8.74 (2H, d, J=1.6 Hz), 8.63 (2H, s), 8.48 (1H, d, J=5.6 Hz), 7.90 (2H, d, J=8.0 Hz), 7.60 (2H, d, J=7.6 Hz), 7.51 (1H, t, J=7.2 Hz), 7.27 (2H, d, J=7.6 Hz), 7.19 (3H, t, J=8.0 Hz), 3.93-3.94 (2H, m), 3.10-3.15 (2H, m), 2.91-2.99 (4H, m), 2.73-2.75 (1H, m), 2.48 (2H, d, J=1.6 Hz) IS-MS, m/e 462.1 (m+1).

Example 85

7-Phenyl-isoquinoline-5-sulfonic acid [2-(2-hydroxy-3-(4-nitrophenyl)-propylamino)-ethyl]-amide, dihydrochloride salt, Enantiomer 1

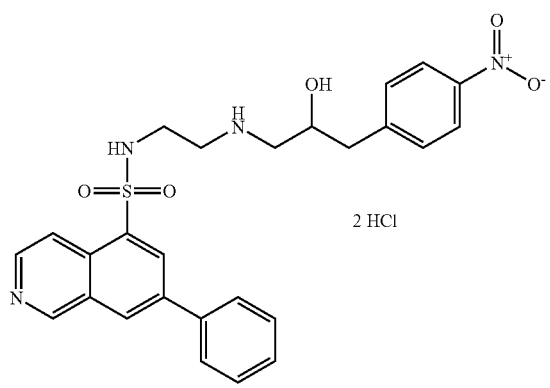

Prepare the racemate of the title compound according to example 83, and separate the enantiomer by preparative chiral HPLC to afford the less-retained isomer. Treat with aqueous hydrochloric acid and lyophylize to obtain the title compound. ¹H NMR (DMSO): δ9.66(s, 1H), 8.91-8.82(m, 2H), 8.77(d, J=6.3 Hz, 1H), 8.70-8.60(m, 3H), 8.51(d, J=6.3 Hz, 1H), 8.19(d, J=8.5 Hz, 1H), 7.94(d of t, J1=8.3 Hz, 3 Hz, 2H), 7.63 (t, J=7.5 Hz, 2H), 7.58-7.48(m, 3H), 4.10-3.99(m, 1H), 3.18(q, J=6.4 Hz, 2H), 3.09-2.74(m,7H). LCMS: m/z 507 (M+H)⁺, 505(M−H). 40% IPA 60% Heptane 0.2% DMEA on a Chiral pak AD (0.46×15 cm) 1.0 ml/min, 20 ul inj, 225 nm. Ret Time (min) 7.27

Example 86

7-Phenyl-isoquinoline-5-sulfonic acid [2-(2-hydroxy-3-(4-nitrophenyl)-propylamino)-ethyl]-amide, dihydrochloride salt, Enantiomer 2

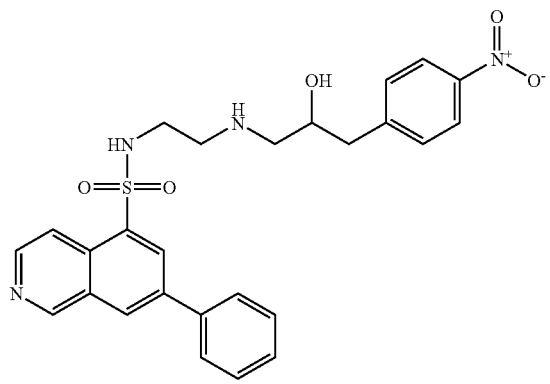

According to example 85, further elution affords the second isomer of the title compound. Treat with aqueous hydrochloric acid and lyophylize to obtain the title compound. ¹H NMR (DMSO): δ9.66(s, 1H), 8.91-8.82(m, 2H), 8.77(d, J=6.3 Hz, 1H), 870-8.60(m, 3H), 8.51(d, J=6.3 Hz, 1H), 8.19(d, J=8.5 Hz, 1H), 7.94(d of t, J1=8.3 Hz, 3 Hz, 2H), 7.63 (t, J=7.5 Hz, 2H), 7.58-7.48(m, 3H), 4.10-3.99(m, 1H), 3.18 (q, J=6.4 Hz, 2H), 3.09-2.74(m,7H). LCMS: m/z 507 (M+H)⁺, 505(M−H). 40% IPA 60% Heptane 0.2% DMEA on a Chiral pak AD (0.46×15 cm) 1.0 ml/min, 20 ul inj, 225 nm. Ret Time (min) 8.43

Example 87

7-Phenyl-isoquinoline-5-sulfonic acid [2-(2,3-dihydroxy-3-(4-nitrophenyl)-propylamino)-ethyl]-amide, dihydrochloride salt

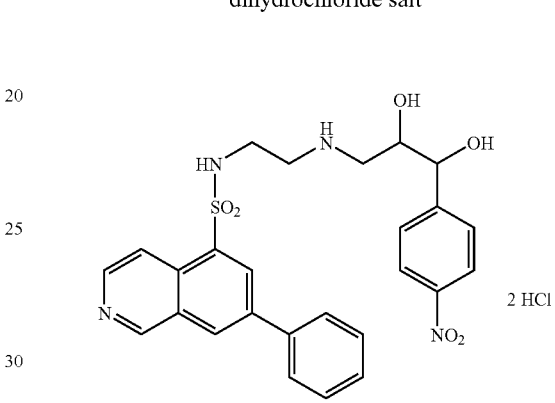

Add 4M HCl/dioxane solution (400 μL, 1.60 mmol) to a solution of [2,3-dihydroxy-3-(4-nitro-phenyl)-propyl]-[2-(7-phenyl-isoquinoline-5-sulfonylamino)-ethyl]-carbamic acid tert-butyl ester (100 mg, 0.16 mmol in CH₂Cl₂ (3 mL) and CH₃OH (2 mL) at room temperature under argon, and stir the mixture for 2 hours. Evaporate the solvent and wash the salt several times with Et₂O and dry, to obtain the title compound. ¹H NMR (CD₃OD): δ9.95 (bs, 1H), 8.94-9.12 (m, 3H), 8.78 (m, 1H), 8.24 (m, 2H), 7.94 (m, 2H), 7.52-7.72 (m, 5H); 4.82-4.97 (m, 1H, under H₂O signal), 4.07-4.15 (m, 1H), 3.05-3.31 (m, 6H).

Example 88

7-Phenyl-isoquinoline-5-sulfonic acid [2-(2,3-dihydroxy-3-(4-nitrophenyl)-propylamino)-ethyl]-amide, dihydrochloride salt, Isomer 1

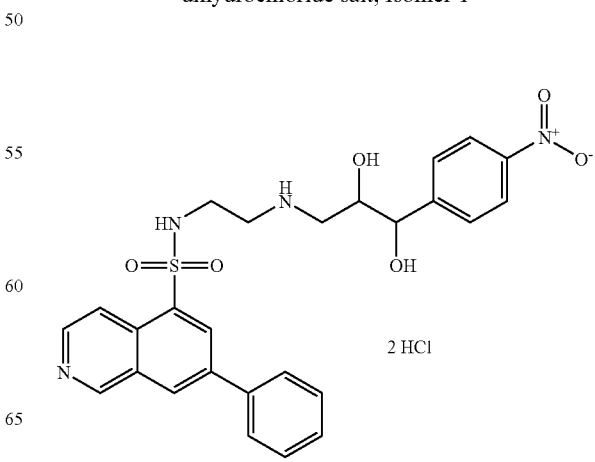

Using chiral HPLC resolution, separate both enantiomers of [2,3-dihydroxy-3-(4-nitro-phenyl)-propyl]-[2-(7-phenyl-isoquinoline-5-sulfonylamino)-ethyl]-carbamic acid tert-butyl ester (ChiralPak AD, hexane/EtOH 20:80, 0.75 mL/min). Obtain the title compound by treatment of with 4M HCl/ dioxane solution.

$^1$H NMR (CD$_3$OD): δ9.95 (bs, 1H), 8.94-9.12 (m, 3H), 8.78 (m, 1H), 8.24 (m, 2H), 7.94 (m, 2H), 7.52-7.72 (m, 5H), 4.82-4.97 (m, 1H, under H$_2$O signal), 4.07-4.15 (m, 1H), 3.05-3.31 (m, 6H). ESIMS: m/z 523 [M+H]$^+$. e.e.>98%

Example 89

7-Phenyl-isoquinoline-5-sulfonic acid [2-(2,3-dihydroxy-3-(4-nitrophenyl)-propylamino)-ethyl]-amide, dihydrochloride salt, Isomer 2

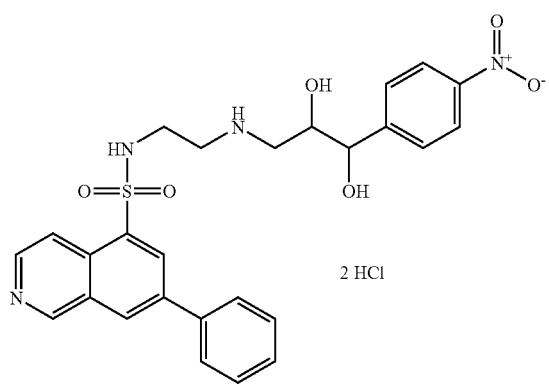

Using chiral HPLC resolution, separate both enantiomers of [2,3-dihydroxy-3-(4-nitro-phenyl)-propyl]-[2-(7-phenyl-isoquinoline-5-sulfonylamino)-ethyl]-carbamic acid tert-butyl ester (ChiralPak AD, hexane/EtOH 20:80, 0.75 mL/min). Obtain the title compound by treatment with 4M HCl/dioxane solution and evaporation.

$^1$H NMR (CD$_3$OD): δ9.95 (bs, 1H), 8.94-9.12 (m, 3H), 8.78 (m, 1H), 8.24 (m, 2H), 7.94 (m, 2H), 7.52-7.72 (m, 5H), 4.82-4.97 (m, 1H, under H$_2$O signal), 4.07-4.15 (m, 1H), 3.05-3.31 (m, 6H). ESIMS: m/z 523 [M+H]$^+$. e.e.>98%

Example 90

7-(4-aminophenyl)-isoquinoline-5-sulfonic acid [2-(3-(4-nitrophenyl)-propylamino)-ethyl]-amide, trihydrochloride salt

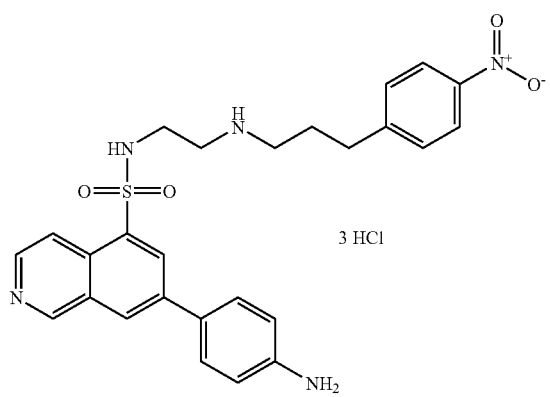

Prepare the title compound according to a procedure similar to example 97, substituting 7-(4-amino-phenyl)-isoquinoline-5-sulfonic acid (2-amino-ethyl)-amide (from preparation 91) for 7-(3-difluoromethylphenyl)-isoquinoline-5-sulfonic acid (2-amino-ethyl)-amide. $^1$H NMR (DMSO-d$_6$, 400 MHz): 9.05 (2H, br), 8.82 (1H, s), 8.65 (1H, t, J=5.2 Hz), 8.65 (1H, s), 8.60 (1H, s), 8.15 (2H, d, J=8.0 Hz), 7.88 (2H, d, J=8.4 Hz), 7.48 (2H, d, J=8.4 Hz), 7.22 (2H, m), 3.13-3.15 (2H, m), 2.95-2.97 (2H, m), 2.82-2.84 (2H, m), 2.75 (2H, t, J=7.6 Hz), 1.86-1.88 (2H, m). IS-MS, m/e 506.60 (m+1).

Example 91

7-(2-hydroxy-phenyl)-isoquinoline-5-sulfonic acid {2-[3-(4-nitro-phenyl)-propylamino]-ethyl}-amide dihydrochloric acid

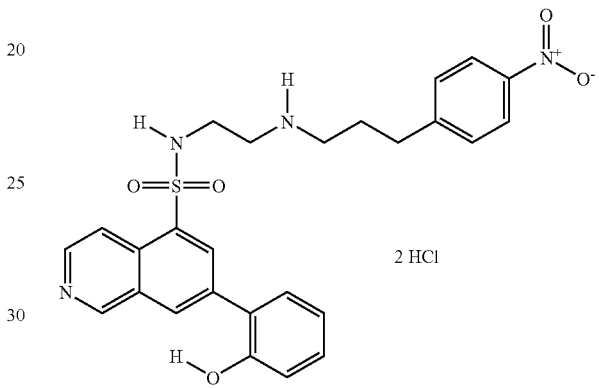

Prepare the title compound from {2-[7-(2-hydroxy-phenyl)-isoquinoline-5-sulfonylamino]-ethyl}-[3-(4-nitro-phenyl)-propyl]-carbamic acid tert-butyl ester, following a procedure similar to Example 98, to give 0.094 g of a yellow solid in 98% yield. ES Positive Ion MS [M+H]$^+$ ion observed: m/z 507. $^1$H-NMR (DMSO-d$_6$) δ 10.09 (br s, 1H), 9.67 (br s, 1H), 8.85 (br s, 2H), 8.74 (br s, 1H), 8.69 (d, J=8.4 Hz, 2H), 8.61-8.62 (m, 1H), 8.54 (br d, J=5.3 Hz, 1H), 8.14 (d, J=8.8 Hz, 2H), 7.46-7.51 (m, 3H), 7.29 (t, J=7.9 Hz, 1H), 7.06 (d, J=7.9 Hz, 1H), 6.98 (t, J=7.5 Hz, 1H), 3.08-3.14 (br m, 2H), 2.95 (br s, 2H), 2.85 (br s, 2H), 2.74 (t, J=7.9 Hz; 2H), 1.85-1.89 (m, 2H).

Example 92

7-(3-aminophenyl)-isoquinoline-5-sulfonic acid [2-(3-(4-nitrophenyl)-propylamino)-ethyl]-amide, trihydrochloride salt

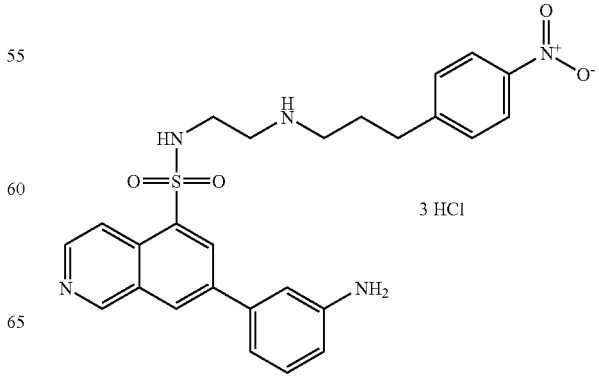

Prepare the title compound according to a procedure similar to example 97, substituting 7-(3-amino-phenyl)-isoquinoline-5-sulfonic acid (2-amino-ethyl)-amide (from preparation 92) for 7-(3-difluoromethylphenyl)-isoquinoline-5-sulfonic acid (2-amino-ethyl)-amide. $^1$H NMR (DMSO-d$_6$, 400 MHz): 9.22 (2H, br), 8.87 (2H, s), 8.66 (2H, s), 8.15 (2H, d, J=8.4 Hz), 7.84-7.88 (2H, m), 7.65 (2H, t, J=7.6 Hz), 7.48 (2H, d, J=8.4 Hz), 7.42 (1H, d, J=7.2 Hz), 3.19-3.21 (2H, m), 2.96-2.98 (2H, m), 2.92-2.94 (2H, m), 2.76 (2H, t, J=7.6 Hz), 1.89-1.92 (2H, m) IS-MS, m/e 506.60 (m+1).

Example 93

7-(3-fluorophenyl)-isoquinoline-5-sulfonic acid [2-(3-(4-nitrophenyl)-propylamino)-ethyl]-amide

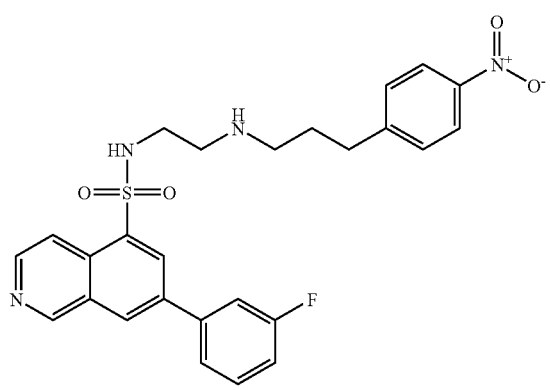

Prepare the title compound according to a procedure similar to example 97, substituting 7-(3-fluoro-phenyl)-isoquinoline-5-sulfonic acid (2-amino-ethyl)-amide (from preparation 91) for 7-(3-difluoromethylphenyl)-isoquinoline-5-sulfonic acid (2-amino-ethyl)-amide, but omitting treatment with hydrochloric acid to afford the free base. $^1$H NMR (DMSO-d$_6$, 400 MHz): 9.52 (1H, s), 8.80 (1H, s), 8.69 (1H, d, J=6.0 Hz), 8.57 (1H, d, J=2.0 Hz), 8.44 (1H, d, J=6.0 Hz), 8.09 (2H, d, J=8.4 Hz), 7.63-7.71 (2H, m), 7.57-7.61 (1H, m), 7.30-7.36 (3H, m), 2.94 (2H, t, J=6.0 Hz), 2.54 (2H, t, J=7.2 Hz), 2.42 (2H, t, J=6.4 Hz), 2.23 (2H, t, J=6.8 Hz), 1.21-1.46 (2H, m). IS-MS, m/e 509.30 (m+1).

Example 94

7-(3-methanesulfonylamino-phenyl)-isoquinoline-5-sulfonic acid {2-[3-(4-nitro-phenyl)-propylamino]-ethyl}-amide, dihydrochloride salt

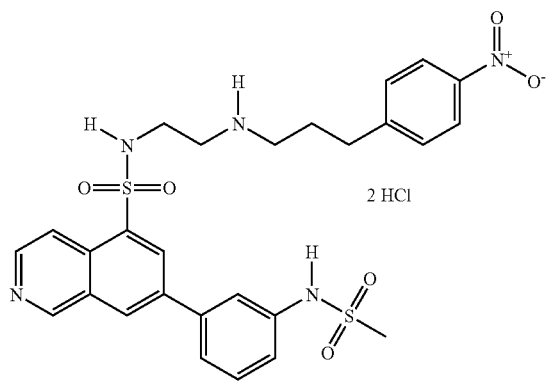

Prepare the title compound from [3-(4-nitro-phenyl)-propyl]-[2-(7-pyridin-3-yl-isoquinoline-5-sulfonylamino)-ethyl]-carbamic acid tert-butyl ester, following a procedure similar to Example 98. ES Positive Ion MS [M+H]$^+$ ion observed: m/z 584. EA for C$_{27}$H$_{29}$N$_5$O$_6$S$_2$.2 HCl: Calculated: C, 49.39; H, 4.76; N, 10.67 Found: C, 49.16; H, 4.82; N, 10.43.

Example 95

7-(3-Amino-phenyl)-isoquinoline-5-sulfonic acid {2-[3-(5-chloro-3'-nitro-biphenyl-2-yl)-propylamino]-ethyl}-amide, trihydrochloride salt

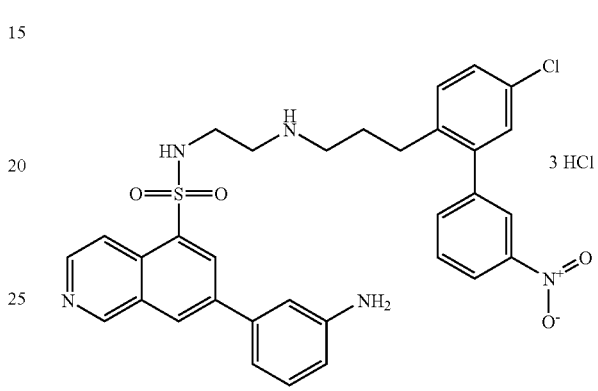

Prepare the title compound according to a procedure similar to example 97, substituting 7-(3-amino-phenyl)-isoquinoline-5-sulfonic acid (2-amino-ethyl)-amide (from preparation 92) for 7-(3-difluoromethylphenyl)-isoquinoline-5-sulfonic acid (2-amino-ethyl)-amide, and substituting 3-(5-chloro-3'-nitro-biphenyl-2-yl)-propionaldehyde (from preparation 69 for 3-(4-nitrophenyl)-propionaldehyde. $^1$H NMR (DMSO-d$_6$, 400 MHz): 8.74 (1H, s), 8.68 (3H, br), 8.58 (1H, s), 8.54 (1H, s), 8.44 (1H, s), 8.24 (1H, d, J=8.8 Hz), 8.09 (1H, s), 7.79 (1H, d, J=7.6 Hz), 7.72 (1H, t, J=8.0 Hz), 7.44-7.46 (3H, m), 7.37 (1H, d, J=7.6 Hz), 7.32 (1H, d, J=2.0 Hz), 3.02-3.04 (2H, m), 2.85-2.87 (2H, m), 2.67-2.69 (2H, m), 2.46-2.48 (2H, m), 1.62-1.64 (2H, m)
IS-MS, m/e 617.15 (m+1)

Example 96

7-(4-methanesulfonylaminophenyl)-isoquinoline-5-sulfonic acid {2-[3-(4-nitro-phenyl)-propylamino]-ethyl}-amide, dihydrochloride salt

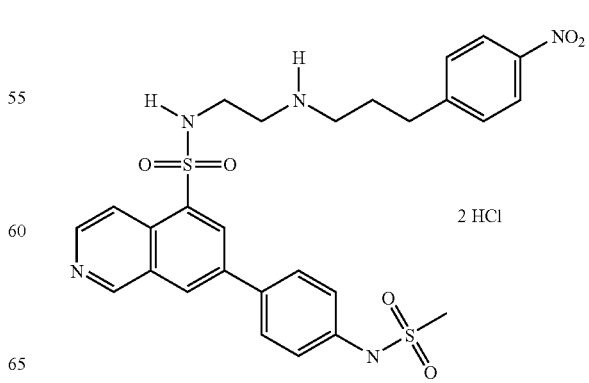

Prepare the title compound according to a procedure similar to example 97, substituting 7-(4-methanesulfonylaminophenyl)-isoquinoline-5-sulfonic acid (2-amino-ethyl)-amide (from preparation 94) for 7-(3-difluoromethylphenyl)-isoquinoline-5-sulfonic acid (2-amino-ethyl)-amide. $^1$H NMR (DMSO-d$_6$, 400 MHz): 10.06 (1H, s), 8.93 (2H, br), 8.80 (1H, s), 8.70 (1H, t, J=6.4 Hz), 8.62 (1H, s), 8.52 (1H, s), 8.15 (2H, d, J=8.0 Hz), 7.91 (2H, d, J=8.0 Hz), 7.48 (2H, d, J=8.4 Hz), 7.40 (2H, d, J=8.0 Hz), 3.12-3.15 (2H, m), 3.06 (3H, s), 2.95-2.97 (2H, m), 2.82-2.84 (2H, m), 2.75 (2H, t, J=8.0 Hz), 1.86-1.89 (2H, m). IS-MS, m/e 584.69 (m+1)

Example 97

7-(3-Difluoromethylphenyl)-isoquinoline-5-sulfonic acid {2-[3-(4-nitro-phenyl)-propylamino]-ethyl}-amide, dihydrochloride salt

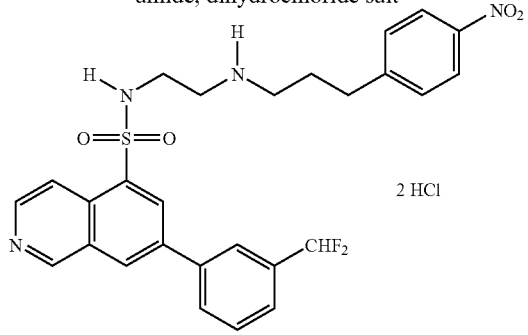

Dissolve 7-(3-Difluoromethylphenyl)-isoquinoline-5-sulfonic acid (2-amino-ethyl)-amide (0.060 g, 0.16 mmol) in a mixture of dichloromethane and methanol (5:1, 15 mL). To the solution add 3-(4-nitrophenyl)-propionaldehyde (0.043 g, 0.24 mmol) as a solution in dichloromethane and stir overnight. Add sodium borohydride (0.025 g, 0.67 mmol). Evaporate the solvent and purify the residue by silica gel chromatography to give the free base of the desired compound (0.042 g, 48% yield): $^1$H NMR (CDCl$_3$/CD$_3$OD): δ9.40 (s, 1H), 8.70 (m, 2H), 8.40 (m, 2H), 8.10 (m, 2H), 7.85 (m, 2H), 7.62 (m, 2H), 7.26 (m, 2H), 6.73 (t, J=52.1 Hz, 1H), 3.00 (m, 2H), 2.64 (m, 4H), 2.42 (t, J=7.0 Hz, 2H), 1.67 (m, 2H). ESIMS: m/z 541 (M+H)$^+$. Form the dihydrochloride salt by suspending the free base in ethyl acetate, cooling to 0° C., and adding 4M HCl in 1,4-dioxane dropwise. Filter the precipitate and wash with dichloromethane then dry in vacuum to give the desired compound.

Example 98

7-(4-hydroxy-phenyl)-isoquinoline-5-sulfonic acid {2-[3-(4-nitro-phenyl)-propylamino]-ethyl}-amide, dihydrochloride salt

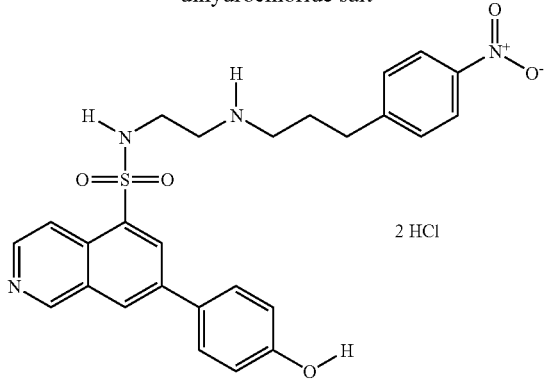

To {2-[7-(4-hydroxy-phenyl)-isoquinoline-5-sulfonylamino]-ethyl}-[3-(4-nitro-phenyl)-propyl]-carbamic acid tert-butyl ester, (0.090 g, 0.148 mmol) in 6 ml (1:1) CH$_2$Cl$_2$/MeOH bubble HCl (g) for several minutes, then stir for 1 h and filter to give 0.0859 g of 7-(4-hydroxy-phenyl)-isoquinoline-5-sulfonic acid {2-[3-(4-nitro-phenyl)-propylamino]-ethyl}-amide dihydrochloric acid in 100% yield. ES Positive Ion MS [M+H]$^+$ ion observed: m/z 507. $^1$H-NMR (DMSO-d$_6$) δ9.62 (s, 1H), 8.93 (br s, 2H), 8.75 (s, 1H), 8.69-8.71 (m, 2H), 8.61 (s, 1H), 8.52 (d, J=6.2 Hz, 1H), 8.15 (d, J=8.8 Hz, 2H), 7.75 (d, J=8.8 Hz, 2H), 7.48 (d, J=8.8 Hz, 2H), 6.96 (d, J=8.4 Hz, 2H), 3.10-3.15 (br m, 2H), 2.90-3.00 (br s, 2H), 2.87 (br s, 2H), 2.75 (t, J=7.5 Hz; 2H), 1.87-1.90 (m, 2H).

Example 99

7-(3-hydroxy-phenyl)-isoquinoline-5-sulfonic acid {2-[3-(4-nitro-phenyl)-propylamino]-ethyl}-amide, dihydrochloride salt

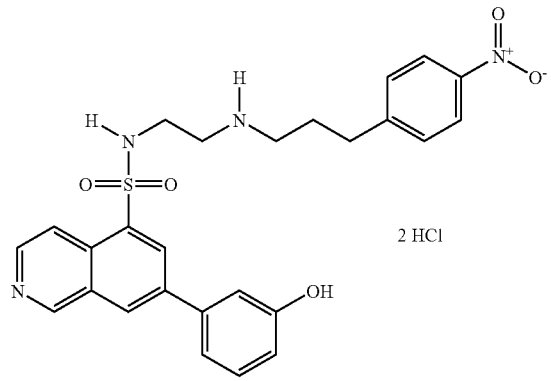

Prepare the title compound from {2-[7-(3-hydroxy-phenyl)-isoquinoline-5-sulfonylamino]-ethyl)-[3-(4-nitro-phenyl)-propyl]-carbamic acid tert-butyl ester, following a procedure similar to example 98. ES Positive Ion MS [M+H]$^+$ ion observed: m/z 507; $^1$H-NMR (DMSO-d$_6$) 89.66 (s, 1H), 9.60-9.90 (br s, 1H). 8.92 (br s, 2H), 8.80 (s, 1H), 8.68-8.74 (m, 2H), 8.58 (s, 1H), 8.52 (d, J=6.2 Hz, 1H), 8.14 (d, J=8.8 Hz, 2H), 7.47 (d, J=8.8 Hz, 2H), 7.37 (t, J=7.5 Hz, 1H), 7.30 (d, J=7.5 Hz, 1H), 7.26 (s, 1H), 6.89 (d, J=7.9 Hz, 1H), 3.11-3.13 (br m, 2H), 2.95 (br s, 2H), 2.86 (br s, 2H), 2.74 (t, J=7.5 Hz; 2H), 1.86-1.89 (m, 2H).

Using a procedure similar to that described in Example 1 and using the appropriate starting materials, the following compounds may be prepared and isolated as the dihydrochloride salt, with the exception of Example 106, which is prepared by preparative HPLC using an acetonitrile-0.1% TFA mobil phase system to afford the final compound as a bis-trifluoroacetate salt.

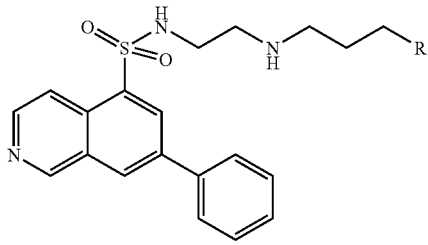

| Ex # | Prep # | R | Data |
|---|---|---|---|
| 100 | 95 | 4-methanesulfonyl-phenyl | NMR (DMSO-d6): 1.92 (m, CH2), 2.74 (t, J = 7.5 Hz, CH2), 2.87 (bs, CH2), 2.99 (bs, CH2), 3.18 (s, CH3), 3.21 (m, CH2), 7.41-7.64 (m, 5H, Ar), 7.85 (d, 2H, J = 8.0 Hz, Ar), 7.91 (AB system, 4H, Ar), 8.71-8.98 (m, 5H, Ar), 9.21 (bs 2H, NH2), 9.84 (bs 1H, NH) LCMS (ESI): 524 (M + H) |
| 101 | 96 | 3-nitro-phenyl | $^1$H NMR (DMSO): δ 9.55 (s, 1H), 8.76 (d, J = 1.5 Hz, 1H), 8.71 (d, J = 6.2 Hz, 1H), 8.61 (d, J = 2.2 Hz, 1H,), 8.47 (d, J = 6.2 Hz, 1H), 8.04 (tt, J1 = 1.7 Hz, J2 = 7.7 Hz, 1H), 8.00 (t, J = 1.7 Hz, 1H), 7.90 (dt, J1 = 1.3 Hz, J2 = 7.1 Hz, 2H), 7.63-7.48 (m, 6H), 3.34 (bs, 2H), 2.96 (t, J = 6.2 Hz, 2H), 2.60 (t, J = 7.5 Hz, 2H), 2.47 (t, J = 6.2 Hz, 2H), 2.27 (t, J = 7.0 Hz, 2H), 1.50 (p, J = 7.0 Hz, 2H). LCMS: m/z 491 (M + H)$^+$, 489 (M − H). |
| 102 | 97 | 4-trifluoromethanesulfonyl-phenyl | $^1$H NMR (DMSO): δ 9.61 (bs, 1H)), 8.90-8.72 (m, 4H), 8.67-8.58 (m, 2H), 8.48 (d, J = 6.2 Hz, 1H), 8.10 (d, J = 8.4 Hz, 2H), 7.94 (d, J = 7.8 Hz, 2H), 7.71 (d, J = 8.4 Hz, 2H), 7.63 (t J = 7.4 Hz, 2H), 7.57-7.50 (m, 1H), 3.15 (q, J = 6.3 Hz, 2H), 3.01 (p, J = 5.6 Hz, 2H), 2.97-2.88 (m,2H), 2.84 (t, J = 7.6 Hz, 2H), 1.94 (p, J = 7.5 Hz, 2H). LCMS: m/z 578 (M + H)$^+$, 576 (M − H). |
| 103 | 98 | 2-ethyl-4-nitro-phenyl | $^1$H NMR (CD$_3$OD): δ 1.30 (t, J = 7.5 Hz, 3H), 2.05 (quint, J = 7.9 Hz, 2H), 2.76-2.92 (m. 4H), 3.12-3.29 (m, 6H), 7.45 (d, J = 8.6 Hz, 1H), 7.53-7.67 (m, 3H), 7.91-7.98 (m, 2H), 8.02 (m, 1H), 8.10 (m, 1H), 8.79 (m, 1H), 8.97-9.16 (m, 3H), 9.96 (m, 1H). ESIMS: m/z 519.5 [M + H]$^+$. |
| 104 | 99 | 4-cyano-2-methyl-phenyl | $^1$H NMR (DMSO): δ 9.66 (s, 1H), 8.96-8.85 (m, 3H), 8.77 (d, J = 4.4 Hz, 1H), 8.70 (t, J = 5.6 Hz, 1H), 8.66 (d, J = 2.1 Hz, 1H), 8.53 (d, J = 5.6 Hz, 1H), 7.94 (dt, J1 = 1.3 Hz, J2 = 7.0 Hz, 2H), 7.67-7.58 (m, 4H), 7.53 (tt, J1 = 1.3 Hz, J2 = 7.3 Hz, 1H), 7.35 (d, J = 7.9 Hz, 1H), 3.17 (q, J = 6.6 Hz, 2H), 3.05-2.88 (m, 4H), 2.68 (t, J = 7.6 Hz, 2H), 2.31 (s, 3H), 1.83 ( p, J = 7.4 Hz, 2H). LCMS: m/z 485 (M + H)$^+$, 483 (M − H). |
| 105 | 100 | 3-hydroxy-4-nitro-phenyl | $^1$H NMR (300 MHz, CD$_3$OD) δ 2.06 (quin, 2H, J = 7.3 hz), 2.78 (t, 1H, J = 7.3 Hz), 3.09 (t, 2H, J = 7.3 Hz), 3.17-3.26 (m, 4H), 6.93 (d, 1H, J = 8.8 Hz), 7.05 (s, 1H), 7.55-7.65 (m, 3H), 7.93 (d, 2H, J = 7.3 Hz), 8.03 (d, 1H, J = 8.8 Hz), 8.78 (d, 1H, J = 6.5 Hz), 9.01 (s, 1H), 9.04 (s, 1H), 9.12 (d, 1H, J = 6.5 Hz), 9.96 (1H). ESIMS: m/z 507 (M +H)$^+$. |
| 106 | 101 | 4-cyano-3-hydroxy-phenyl | $^1$H NMR (CD$_3$OD): δ 9.01 (br. s, 1H), 8.89 (br. s, 1H) 8.87 (d, J = 13.4 Hz, 2H), 7.87 (d, J = 7.73 Hz, 2H), 7.58 (m, 4H), 7.41 (d, J = 6.7 Hz, 1H), 6.82 (d, 1H), 6.81 (d, J = 8.2 Hz, 1H), 3.20 (m, 4H), 3.04 (m, 2H), 2.69 (m, 2H), 2.66 (s, 1H), 2.02 (m, 2H). MS m/z 487.2 (M + H)$^+$. |

Prepare the following compounds as the free base using reductive amination conditions found in Example 1, with the exception of treatment with hydrochloric acid.

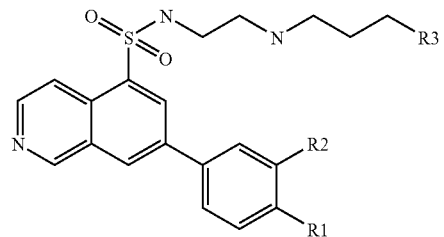

| Ex # | Prep# | R1 | R2 | R3 | Data |
|------|-------|----|----|----|------|
| 107 | 102, 104 | H | OH | 3-hydroxyphenyl | $^1$H NMR (DMSO-$d_6$, 400 MHz) δ: 9.46 (1H, d, J=0.8 Hz), 8.62 (1H, d, J=6.0 Hz), 8.60 (1H, d, J=1.2 Hz), 8.51 (1H, d, J=1.6 Hz), 8.40 (1H, d, J=6.0 Hz), 7.70 (2H, d, J=7.2 Hz), 6.98 (1H, t, J=7.6 Hz), 6.94 (2H, d, J=8.8 Hz), 6.52-6.46 (3H, m), 2.89 (2H, t, J=6.0 Hz), 2.39 (2H, t, J=6.0 Hz), 2.30 (2H, t, J=8.4 Hz), 2.18 (2H, t, J=7.2 Hz), 1.41-1.35 (2H, m). IS-MS. m/e: 478.2 (m + 1). |
| 108 | 103, 105 | OH | H | 2-flouro-4-methoxyphenyl | $^1$H NMR (DMSO-$d_6$, 400 MHz) δ: 9.45 (1H, s), 8.61 (1H, d, J=6.4 Hz), 8.59 (1H, br), 8.51 (1H, d, J=2.0 Hz), 8.39 (1H, d, J=5.6 Hz), 7.69 (2H, d, J=8.4 Hz), 6.98 (1H, t, J=9.6 Hz), 6.93 (2H, d, J=8.8 Hz), 6.72-6.69 (2H, m), 3.67 (3H, s), 2.87 (2H, t, J=6.0 Hz), 2.42-2.39 (4H, m), 2.22 (2H, t, J=7.2 Hz), 1.41-1.37 (2H, m). IS-MS, m/e: 510.2 (m + 1). |
| 109 | 102, 105 | OH | H | 3-hydroxyphenyl | $^1$H NMR (DMSO-$d_6$, 400 MHz) δ: 9.52 (1H, s), 8.67 (2H, d, J=6.0 Hz), 8.52 (1H, d, J=1.6 Hz), 8.42 (1H, d, J=6.0 Hz), 7.36 (1H, t, J=7.6 Hz), 7.27 (1H, d, J=8.4 Hz), 7.23 (1H, t, J=2.4), 6.98 (1H, t, J=8.0 Hz), 6.88-6.86 (1H, m), 6.52-6.46 (3H, m), 2.89 (2H, t, J=6.4 Hz), 2.40 (2H, t, J=6.4 Hz), 2.30 (2H, t, J=8.0 Hz), 2.18 (2H, t, J=6.4 Hz), 1.39-1.35 (2H, m). IS-MS, m/e: 478.2 (m + 1). |
| 110 | 103, 104 | H | OH | 2-fluoro-4-l methoxyphenyl | $^1$H NMR (DMSO-$d_6$, 400 MHz) δ: 9.50 (1H, s), 8.67-8.51 (2H, m), 8.42 (1H, d, J=6.0 Hz), 7.36 (1H, d, J=8.0 Hz), 7.35 (1H, t, J=8.0 Hz), 7.27-7.23 (2H, m), 7.00 (1H, t, J=10.4 Hz), 6.89-6.86 (1H, m), 6.72-6.70 (2H, m), 3.67 (3H, s), 2.89 (2H, t, J=6.0 Hz), 2.42-2.39 (4H, m), 2.22 (2H, t, J=7.2 Hz), 1.41-1.37 (2H, m). IS-MS, m/e: 510.2 (m + 1). |

Example 111

7-Phenyl-isoquinoline-5-sulfonic acid (2-[3-(4-cyano-phenyl)-2-hydroxy-propylamino]-ethyl}-amide, dihydrochloride salt

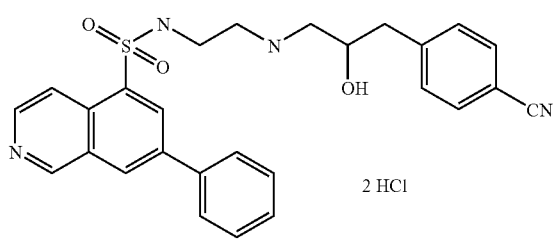

2 HCl

Irradiate a slurry of 7-phenyl-isoquinoline-5-sulfonic acid (2-amino-ethyl)-amide (276 mg, 0.84 mg as free base) and 4-oxiranylmethyl-benzonitrile (134 mg, 0.84 mmol, Preparation 106) in 10 ml of EtOH in a microwave oven at 140° C. (700 W) for 10 min. After cooling at room temperature, evaporate in vacuo and purify the crude by silica gel chromatography (CH$_2$Cl$_2$-ammonia (2M in MeOH) (3%)) affording the free base (150 mg, 26%). Form the salt by treating a dicloromethane solution of the free base with 5 equivalents of HCl (2M in ether) during 1 hour at room temperature and evaporating the solvent under reduced pressure (99%). $^1$H NMR (CD$_3$OD): δ10.02 (br. s, 1H), 9.15 (m, 1H), 9.06 (m, 2H), 8.82 (m, 1H), 7.96 (d, J=7.5 Hz, 2H), 7.6 (m, 5H), 7.48 (d, J=7.38 Hz, 2H), 4.18 (m, 1H), 3.2-2.8 (m, 5H). MS m/z 487 (M+H)$^+$.

According to the general procedure found in example 87, prepare the following compounds as the dihydrochloride salt.

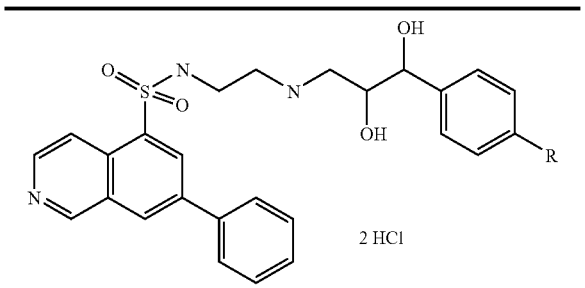

2 HCl

| Ex # | Prep# | R | Data |
|---|---|---|---|
| 112 | 107 | CN | $^1$H NMR (CD$_3$OD): δ3.05-3.28 (m, 6H), 4.08 (m, 1H), 4.79 (m, 1H), 7.53-7.68 (m, 5H), 7.73 (d, 2H, J=8.1 Hz), 7.94 (m, 2H), 8.77 (m, 1H), 8.94-9.11 (m, 3H), 9.92 (m, 1H). ESIMS: m/z 503.5 [M + H]$^+$. |
| 113 | 108 | SO$_2$CF3 | $^1$H NMR (CD$_3$OD): δ9.99 (br. s, 1H), 9.14 (d, J=6.2 Hz, 1H), 9.04 (d, J=8.3 Hz, 2H), 8.81 (br. s, 1H), 8.1 (d, J=8.3 Hz, 2H), 7.96 (d, J=7.5 Hz, 2H), 7.88 (d, J=8.3 Hz, 2H), 7.62 (m, 3H), 4.94 (d, J=2.95 Hz, 1H), 4.16 (m, 1H), 4.08 (m, 1H), 3.75 (t, J=12.7 Hz, 1H), 3.45 (d, J=11.8 Hz, 1H), 3.28 (m, 3H). MS m/z 610.1 (M + H)$^+$. |

Example 114

7-Phenyl-isoquinoline-5-sulfonic acid {2-[3-(4-nitro-phenyl)-propylamino]-ethyl}-amide, dihydrochloride

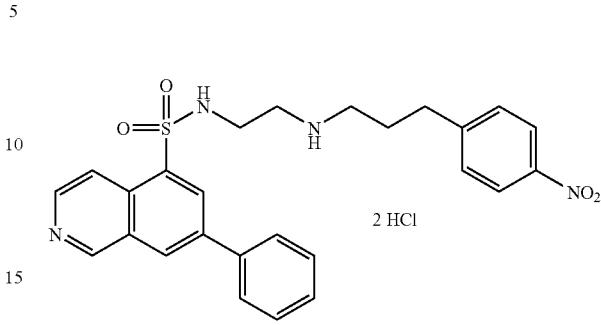

2 HCl

Bubble gaseous HCl through a solution of [3-(4-Nitro-phenyl)-propyl]-[2-(7-phenyl-isoquinoline-5-sulfonylamino)-ethyl]-carbamic acid tert-butyl ester (1.9 g, 2.9 mmol) in methanol/dichloromethane (1:1) with cooling for 15 minutes. Remove the solvent under reduced pressure to afford the title compound as a foam.

Example 115

7-Phenyl-isoquinoline-5-sulfonic acid {2-[3-(4-nitro-phenyl)-propylamino]-ethyl}-amide, dimesylate

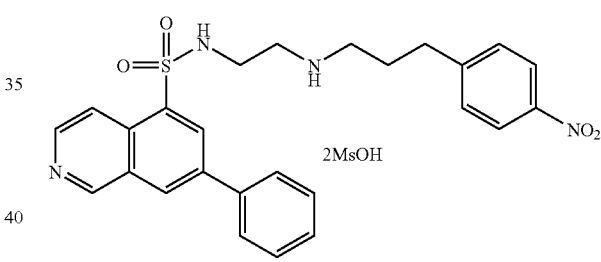

2MsOH

Combine [3-(4-Nitro-phenyl)-propyl]-[2-(7-phenyl-isoquinoline-5-sulfonylamino)-ethyl]-carbamic acid tert-butyl ester (1 g, 1.52 mmol) and isopropyl alcohol in a 100 mL flask. Heat the flask to obtain homogeneity. Add methanesulfonic acid (0.3 mL, 4.57 mmol) and heat to 70° C. for 3 hours. Slowly cool to room temperature and filter the solids. Recrystallize the solids from hot isopropyl alcohol and water to afford the title compound as a white solid. $^1$H NMR (DMSO, 500.0 MHz): δ 9.64 (s, 1H), 8.87 (s, 1H), 8.77 (d, 1H, J=6 Hz), 8.63 (s, 1H), 8.52 (apparent t, 1H, J=4.5 Hz), 8.48 (d, 1H, J=7 Hz), 8.43 (br s, 2H), 8.20 (d, 2H, J=7 Hz), 7.92 (d, 2H, J=7.5 Hz), 7.63 (t, 2H, J=7.5 Hz), 7.48-7.56 (m, 3H), 3.00-3.10 (m, 2H), 2.95-3.04 (m, 2H), 2.90-2.92 (m, 2H), 2.77 (t, 2H, J=7.5 Hz), 2.33 (s, 3H), 2.32 (s, 3H), 1.89 (p, 2H, J=7 Hz).

The compounds of the present invention can be administered alone or in the form of a pharmaceutical composition, that is, combined with pharmaceutically acceptable carriers, or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, for purposes of stability, convenience of crystallization, increased solubility, and the like.

Thus, the present invention provides pharmaceutical compositions comprising a compound of the Formula (I) and a pharmaceutically acceptable diluent.

The compounds of Formula (I) can be administered by a variety of routes. In effecting treatment of a patient afflicted with disorders described herein, a compound of Formula (I) can be administered in any form or mode that makes the compound bioavailable in an effective amount, including oral and parenteral routes. For example, compounds of Formula (I) can be administered orally, by inhalation, or by the subcutaneous, intramuscular, intravenous, transdermal, intranasal, rectal, occular, topical, sublingual, buccal, or other routes. Intravenous (IV) administration is generally preferred for treatment of the disorders described herein. However, intravenous administration is not the only preferred route. For example, the oral route may be preferred as a matter of convenience or to avoid potential complications related to intravenous administration. When the compound of Formula (I) is administered through the intravenous route, an intravenous bolus or slow infusion is preferred.

One skilled in the art of preparing formulations can readily select the proper form and mode of administration depending upon the particular characteristics of the compound selected, the disorder or condition to be treated, the stage of the disorder or condition, and other relevant circumstances. (*Remington's Pharmaceutical Sciences,* 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as povidone, hydroxypropyl cellulose, microcrystalline cellulose, gum tragacanth or gelatin; excipients such as dicalcium phosphate, starch, or lactose; disintegrating agents such as alginic acid, Primogel, corn starch and the like; lubricants such as talc, hydrogenated vegetable oil, magnesium stearate or Sterotex; glidants such as colloidal silicon dioxide; and sweetening agents, such as sucrose, aspartame, or saccharin, or a flavoring agent, such as peppermint, methyl salicylate or orange flavoring, may be added. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, coatings. Thus, tablets or pills may be coated with sugar, shellac, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

The compounds of Formula (I) are inhibitors of Akt1 activity. The inhibitory activity of the compounds of Formula (I) may be demonstrated by the methods below.

Akt1 Phosphorylation Assay

The assay described measures the phosphorylation of Crosstide by active human Akt1 and other Akt isoforms. Crosstide contains a consensus sequence derived from Akt substrates GSK3b and forkhead transcription factors (FKs). The $^{33}$P-labeled Crosstide substrate is captured by phosphocellulose membrane filter plates.

Enzyme and Substrate

Active human recombinant Akt1 (full-length) purified from Sf9 insect cells is from Upstate Biotechnology, Inc. (Cat. #14-276, 405 µg/ml). Crosstide substrate, $NH_2$-GR-PRTSSFAEG-COOH (M.W.1164) is purchased from Multiple Peptide System (Cat. # L59/GR145-153).

Standard Assay Solutions

Solution (A): 20% DMSO (dimethylsulphoxide) or Compound in 20% DMSO; Solution (B): Assay Buffer Mix: 31.25 µM Crosstide, 37.5 mM $MgCl_2$, 87.5 mM HEPES, pH 7.3, 50 µM ATP γ-$^{33}$P-ATP, 0.05 µCi/µl; Solution (C): Akt Kinase Mix: 31.25 mM HEPES, pH 7.3; 1 mM DTT, 25 nM UBI Akt1.

Procedure for Phosphocellulose Filter-Binding Assay

Ten µl of Solution (A) are first mixed with 20 µl Solution (B). The enzymatic reaction is initiated by adding 20 µl Solution (C) to the mixture. (Final concentration or amount in a 50-µl reaction mix: 4% DMSO or various compound concentration in 4% DMSO; 12.5 µM Crosstide; 15 mM $MgCl_2$; 35 mM HEPES, pH7.3; 20 µM ATP; 1 µCi γ-$^{33}$P-ATP; 0.4 mM DTT; 10 nM UBI Akt1.) The reactions are performed in 96-well microtiter plates.

After 30 minutes at room temperature, the reaction is terminated by adding 80 µl of 10% $H_3PO_4$. An aliquot of 100 µl from each well is transferred to the phosphocellulose filter plate (Millipore MultiScreen, Catalog #MAPHN0B50). After 30 minutes, the reaction mix is filtered with a Millipore manifold following by 3 washes with 0.5% $H_3PO_4$. The filter is then vacuum-dried and the plate is fitted onto a Packard carrier. 100 µl/well Microscint20 are added and the contents are counted in a Packard Top Count.

Representative compounds of Formula (I) selected from compounds described herein as EXAMPLES, when tested in the above assay, are demonstrated to have $IC_{50}$ values of $\leq 2$ µM:

a) 7-Phenyl-isoquinoline-5-sulfonic acid {2-[3-(4-nitrophenyl)-propylamino]-ethyl}-amide, dihydrochloride salt;

b) 7-Phenyl-isoquinoline-5-sulfonic acid {2-[3-(4-bromophenyl)-propylamino]-ethyl}-amide, dihydrochloride salt;

c) 7-Phenyl-isoquinoline-5-sulfonic acid {2-[3-(2-[1,4]diazepin-1-yl-phenyl)-propylamino]-ethyl}-amide, tetrahydrochloride salt;

d) 7-Phenyl-isoquinoline-5-sulfonic acid {2-[3-(2-(piperazin-1-yl-phenyl)-propylamino]-ethyl}-amide, tetrahydrochloride salt;

e) 7-Phenyl-isoquinoline-5-sulfonic acid {2-[3-(3-hydroxyphenyl)-propylamino]-ethyl}-amide, dihydrochloride salt;

f) 7-Phenyl-isoquinoline-5-sulfonic acid {2-[3-(4-hydroxyphenyl)-propylamino]-ethyl}-amide, dihydrochloride salt;

g) 7-Phenyl-isoquinoline-5-sulfonic acid {2-[3-(4-(N-propylamino-sulfonyl)phenyl)-propylamino]-ethyl}-amide, dihydrochloride salt;

h) 7-Phenyl-isoquinoline-5-sulfonic acid {2-[3-(4-(N,N-dimethyl-aminosulfonyl)phenyl)-propyl-amino]-ethyl}-amide, dihydrochloride salt;

i) 7-Phenyl-isoquinoline-5-sulfonic acid {2-[3-(4-(cyclopropyl-carbonylamino)phenyl)-propylamino]-ethyl}-amide, dihydrochloride salt;

j) 7-Phenyl-isoquinoline-5-sulfonic acid {2-[3-(4-(1,1,2,2-tetrafluoroethoxy)phenyl)-propylamino]-ethyl}-amide, dihydrochloride salt;

k) 7-Phenyl-isoquinoline-5-sulfonic acid {2-[3-(4-acetamidophenyl)-propylamino]-ethyl}-amide, dihydrochloride salt;

l) 7-Phenyl-isoquinoline-5-sulfonic acid {2-[3-(4-difluoromethoxy-phenyl)-propylamino]-ethyl}-amide, dihydrochloride salt;

m) 7-Phenyl-isoquinoline-5-sulfonic acid {2-[3-(3-methoxyphenyl)-propylamino]-ethyl}-amide, dihydrochloride salt;

n) 7-Phenyl-isoquinoline-5-sulfonic acid {2-[3-(3-cyanophenyl)-propylamino]-ethyl}-amide, dihydrochloride salt;

o) 7-Phenyl-isoquinoline-5-sulfonic acid {2-[3-(4-cyanophenyl)-propylamino]-ethyl}-amide, dihydrochloride salt;

p) 7-Phenyl-isoquinoline-5-sulfonic acid {2-[3-(4-methylthiophenyl)-propylamino]-ethyl}-amide, dihydrochloride salt;

q) 7-Phenyl-isoquinoline-5-sulfonic acid {2-[3-(5-fluorobiphenyl-2-yl)-propylamino]-ethyl}-amide, dihydrochloride salt;

r) 7-Phenyl-isoquinoline-5-sulfonic acid {2-[3-(2-chloro-4-nitrophenyl)-propylamino]-ethyl}-amide, dihydrochloride salt;

s) 7-Phenyl-isoquinoline-5-sulfonic acid {2-[3-(2-methyl-5-nitrophenyl)-propylamino]-ethyl}-amide, dihydrochloride salt;

t) 7-Phenyl-isoquinoline-5-sulfonic acid {2-[3-(2-methyl-4-nitrophenyl)-propylamino]-ethyl}-amide, dihydrochloride salt;

u) 7-Phenyl-isoquinoline-5-sulfonic acid {2-[3-(5-nitrobiphenyl-2-yl)-propylamino]-ethyl}-amide, dihydrochloride salt;

v) 7-Phenyl-isoquinoline-5-sulfonic acid {2-[3-(4-chloro-2-piperazin-1-yl-phenyl)-propylamino]-ethyl}-amide, tetrahydrochloride salt;

w) 7-Phenyl-isoquinoline-5-sulfonic acid {2-[3-(5-chloro-3'-nitro-biphenyl-2-yl)-propylamino]-ethyl)}-amide, dihydrochloride salt;

x) 7-Phenyl-isoquinoline-5-sulfonic acid {2-[3-(4-chloro-2-(4-methyl-piperazin-1-yl)-phenyl)-propylamino]-ethyl}-amide, tetrahydrochloride salt;

y) 7-Phenyl-isoquinoline-5-sulfonic acid {2-[3-(4-chloro-2-(1,1-dioxo-thiomorpholin-4-yl)-phenyl)-propylamino]-ethyl}-amide, trihydrochloride salt;

z) 7-Phenyl-isoquinoline-5-sulfonic acid {2-[3-(4-chloro-2-(piperidin-4-yl)-phenyl)-propylamino]-ethyl}-amide, trihydrochloride salt;

aa) 7-Phenyl-isoquinoline-5-sulfonic acid {2-[3-(4-chloro-2-(3-methyl-piperazin-1-yl)-phenyl)-propylamino]-ethyl}-amide, tetrahydrochloride salt;

bb) 7-Phenyl-isoquinoline-5-sulfonic acid {2-[3-(4-chloro-2-(1-methyl-pyrrolidin-3-yl)oxy-phenyl)-propylamino]-ethyl}-amide, trihydrochloride salt;

cc) 7-Phenyl-isoquinoline-5-sulfonic acid {2-[3-(4-chloro-2-(pyrrolidin-3-yl)oxy-phenyl)-propylamino]-ethyl}-amide, trihydrochloride salt;

dd) 7-Phenyl-isoquinoline-5-sulfonic acid {2-[3-(2-(2-hydroxy-ethyl)-4-nitro-phenyl)-propylamino]-ethyl}-amide, dihydrochloride salt;

ee) 7-Phenyl-isoquinoline-5-sulfonic acid {2-[3-(4-chloro-2-(2-dimethylamino-ethoxy)-phenyl)-propylamino]-ethyl}-amide, dihydrochloride salt;

ff) 7-Phenyl-isoquinoline-5-sulfonic acid {2-[3-(2-methoxycarbonyl-4-nitrophenyl)-propylamino]-ethyl}-amide, dihydrochloride salt;

gg) 7-Phenyl-isoquinoline-5-sulfonic acid {2-[3-(2-methoxy-4-nitrophenyl)-propylamino]-ethyl}-amide, dihydrochloride salt;

hh) 7-Phenyl-isoquinoline-5-sulfonic acid {2-[3-(2-carboxy-4-nitrophenyl)-propylamino]-ethyl}-amide, dihydrochloride salt;

ii) 7-Phenyl-isoquinoline-5-sulfonic acid {2-[3-(2,4-dichlorophenyl)-propylamino]-ethyl}-amide, dihydrochloride salt;

jj) 7-Phenyl-isoquinoline-5-sulfonic acid {2-[3-(2,3-dichlorophenyl)-propylamino]-ethyl}-amide, dihydrochloride salt;

kk) 7-Phenyl-isoquinoline-5-sulfonic acid {2-[3-(4-cyano-3-trifluoromethylphenyl)-propylamino]-ethyl}-amide, dihydrochloride salt;

ll) 7-Phenyl-isoquinoline-5-sulfonic acid {2-[3-(2,3-difluorophenyl)-propylamino]-ethyl}-amide, dihydrochloride salt;

mm) 7-Phenyl-isoquinoline-5-sulfonic acid (2-{3-[4-chloro-2-(2-morpholino-4-yl-ethoxy)-phenyl]-propylamino}-ethyl)-amide, dihydrochloride salt;

nn) 7-Phenyl-isoquinoline-5-sulfonic acid {2-[3-(2,4-difluorophenyl)-propylamino]-ethyl}-amide, dihydrochloride salt;

oo) 7-Phenyl-isoquinoline-5-sulfonic acid [2-(3-(4-aminophenyl)-propylamino)-ethyl]-amide, dihydrochloride salt;

pp) 7-Phenyl-isoquinoline-5-sulfonic acid [2-(3-hydroxy-3-(4-nitrophenyl)-propylamino)-ethyl]-amide, dihydrochloride salt;

qq) 7-Phenyl-isoquinoline-5-sulfonic acid [2-(3-hydroxy-3-(4-cyanophenyl)-propylamino)-ethyl]-amide, dihydrochloride salt;

rr) 7-Phenyl-isoquinoline-5-sulfonic acid [2-(3-hydroxy-3-(3-nitrophenyl)-propylamino)-ethyl]-amide, dihydrochloride salt;

ss) 7-Phenyl-isoquinoline-5-sulfonic acid [2-(3-hydroxy-3-(4-methanesulfonyl-phenyl)-propylamino)-ethyl]-amide, dihydrochloride salt;

tt) 7-Phenyl-isoquinoline-5-sulfonic acid [2-(3-hydroxy-3-(4-trifluoromethanesulfonyl-phenyl)-propylamino)-ethyl]-amide, dihydrochloride salt;

uu) (R)-7-Phenyl-isoquinoline-5-sulfonic acid [2-(3-hydroxy-3-(4-nitrophenyl)-propylamino)-ethyl]-amide, mesylate salt;

vv) (S)-7-Phenyl-isoquinoline-5-sulfonic acid [2-(3-hydroxy-3-(4-nitrophenyl)-propylamino)-ethyl]-amide, mesylate salt;

ww) 7-Phenyl-isoquinoline-5-sulfonic acid [2-(2-hydroxy-3-(4-nitrophenyl)-propylamino)-ethyl]-amide, dihydrochloride salt;

xx) 7-Phenyl-isoquinoline-5-sulfonic acid [2-(2-hydroxy-3-(4-nitrophenyl)-propylamino)-ethyl]-amide isomer 1, dihydrochloride salt;

yy) 7-Phenyl-isoquinoline-5-sulfonic acid [2-(2-hydroxy-3-(4-nitrophenyl)-propylamino)-ethyl]-amide isomer 2, dihydrochloride salt;

zz) 7-Phenyl-isoquinoline-5-sulfonic acid [2-(2,3-dihydroxy-3-(4-nitrophenyl)-propylamino)-ethyl]-amide, dihydrochloride salt;

aaa) 7-Phenyl-isoquinoline-5-sulfonic acid [2-(2,3-dihydroxy-3-(4-nitrophenyl)-propylamino)-ethyl]-amide isomer 1, dihydrochloride salt;

bbb) 7-Phenyl-isoquinoline-5-sulfonic acid [2-(2,3-dihydroxy-3-(4-nitrophenyl)-propylamino)-ethyl]-amide isomer 2, dihydrochloride salt;

ccc) 7-(4-aminophenyl)-isoquinoline-5-sulfonic acid [2-(3-(4-nitrophenyl)-propylamino)-ethyl]-amide, trihydrochloride salt;

ddd) 7-(2-hydroxy-phenyl)-isoquinoline-5-sulfonic acid {2-[3-(4-nitro-phenyl)-propylamino]-ethyl}-amide, dihydrochloride salt;

eee) 7-(3-aminophenyl)-isoquinoline-5-sulfonic acid [2-(3-(4-nitrophenyl)-propylamino)-ethyl]-amide, trihydrochloride salt;

fff) 7-(3-fluorophenyl)-isoquinoline-5-sulfonic acid [2-(3-(4-nitrophenyl)-propylamino)-ethyl]-amide;

ggg) 7-(3-methanesulfonylamino-phenyl)-isoquinoline-5-sulfonic acid {2-[3-(4-nitro-phenyl)-propylamino]-ethyl}-amide, dihydrochloride salt;

hhh) 7-(4-hydroxy-phenyl)-isoquinoline-5-sulfonic acid {2-[3-(4-nitro-phenyl)-propylamino]-ethyl}-amide, dihydrochloride salt;

iii) 7-(3-hydroxy-phenyl)-isoquinoline-5-sulfonic acid {2-[3-(4-nitro-phenyl)-propylamino]-ethyl}-amide, dihydrochloride salt;

jjj) 7-Phenyl-isoquinoline-5-sulfonic acid {2-[3-(4-methanesulfonyl-phenyl)-propylamino]-ethyl}-amide, dihydrochloride salt;

kkk) 7-Phenyl-isoquinoline-5-sulfonic acid {2-[3-(3-nitro-phenyl)-propylamino]-ethyl}-amide, dihydrochloride salt;

lll) 7-Phenyl-isoquinoline-5-sulfonic acid {2-[3-(4-trifluoromethanesulfonyl-phenyl)-propylamino]-ethyl}-amide, dihydrochloride salt;

mmm) 7-Phenyl-isoquinoline-5-sulfonic acid {2-[3-(2-ethyl-4-nitro-phenyl)-propylamino]-ethyl}-amide, dihydrochloride salt;

nnn) 7-Phenyl-isoquinoline-5-sulfonic acid {2-[3-(4-cyano-2-methyl-phenyl)-propylamino]-ethyl}-amide, dihydrochloride salt;

ooo) 7-Phenyl-isoquinoline-5-sulfonic acid {2-[3-(3-hydroxy-4-nitro-phenyl)-propylamino]-ethyl}-amide, dihydrochloride salt, ppp) 7-Phenyl-isoquinoline-5-sulfonic acid {2-[3-(4-cyano-3-hydroxy-phenyl)-propylamino]-ethyl}-amide, bis-trifluoroacetate salt;

qqq) 7-(3-Hydroxy-phenyl)-isoquinoline-5-sulfonic acid {2-[3-(3-hydroxy-phenyl)-propylamino]-ethyl}-amide;

rrr) 7-(4-Hydroxy-phenyl)-isoquinoline-5-sulfonic acid {2-[3-(2-fluoro-4-methoxy-phenyl)-propylamino]-ethyl}-amide;

sss) 7-(4-Hydroxy-phenyl)-isoquinoline-5-sulfonic acid {2-[3-(3-hydroxy-phenyl)-propylamino]-ethyl}-amide;

ttt) 7-(3-Hydroxy-phenyl)-isoquinoline-5-sulfonic acid {2-[3-(2-fluoro-4-methoxy-phenyl)-propylamino]-ethyl}-amide;

uuu) 7-Phenyl-isoquinoline-5-sulfonic acid {2-[3-(4-cyano-phenyl)-2-hydroxy-propylamino]-ethyl}-amide, dihydrochloride salt, dihydrochloride salt;

vvv) 7-Phenyl-isoquinoline-5-sulfonic acid {2-[3-(4-cyano-phenyl)-2,3-dihydroxy-propylamino]-ethyl}-amide, dihydrochloride salt;

www) 7-Phenyl-isoquinoline-5-sulfonic acid {2-[2,3-dihydroxy-3-(4-trifluoromethanesulfonyl-phenyl)-propylamino]-ethyl}-amide, dihydrochloride salt.

xxx) 7-Phenyl-isoquinoline-5-sulfonic acid {2-[3-(4-nitro-phenyl)-propylamino]-ethyl}-amide, dihydrochloride salt yyy) 7-Phenyl-isoquinoline-5-sulfonic acid {2-[3-(4-nitro-phenyl)-propylamino]-ethyl}-amide, dimesylate salt.

Cell-Based Target Inhibition Assay

As substrates of Akt, the family of forkhead transcription factors (FKs) includes three members: FKHRL1, FKHR and AFX. They share a high degree of sequence homology and are involved in the transcription of pro-apoptotic genes. There are three sites for phosphorylation by Akt: T32/S253/S315 in FKHRL1, T24/S256/S318 in FKHR and T28/S193/S258 in AFX. When phosphorylated, FKs are translocated from nucleus to cytoplasm, thus rendered non-functional.

The following experimental protocol is designed to validate the mechanism of action of Akt inhibitors in cells by measuring the level of inhibition of FK phosphorylation. Ideally, an Akt inhibitor should inhibit the level of FK phosphorylation in a dose-dependent manner, with little effect on the level of phospho-Akt, total Akt or total FK.

Akt1 activity requires phosphorylation at residues T308 and S473. The status of phospho-S473 is used to monitor level of phospho-Akt. Complete inactivation of FK proteins as transcription factors requires phosphorylation of three sites, T32, S253 and S315. The status of phospho-T32 is used to monitor the level of phospho-FK in cells.

Procedure for the Immunoblot-Based Target Inhibition Assay in Cells

Cell Lines:

(a) Cancer cell lines with elevated phospho-Akt as a result of loss of PTEN activity. They include but are not limited to the following: breast cancer: MDA-MB468, MDA-MB436, HCT1937, and BT549 (PTEN−/−); prostate cancer: PC3, LNCaP and its derivatives, LN T1.16, LN T2.9 (PTEN−/−); glioblastoma: U87MG, DBTRG005MG (PTEN−/−). (b) Cancer cell lines with elevated phospho-Akt as a result of reduced PTEN activity. They include but are not limited to the following: Ovarian cancer: A2780 (PTEN+/−). (c) Cancer cell lines with deregulated PI3-kinase activity. They include but are not limited to the following: ovarian cancer: OVCAR3, SKOV3.

For mechanism-validation of the activity of an Akt inhibitor, MDA-MB-468 and U87MG are routinely used. A2780, LNCAP and PC3 have also been used in studies with select sets of Akt inhibitors and shown to respond similarly as MDA-MB-468. Other cell lines having features of (a), (b) and/or (c) above may also be used.

Antibodies:

Primary antibodies include anti-Akt antibody for total Akt (Cell Signaling, cat. # 9272); anti-phospho-S473 Akt (Cell Signaling, Cat. # 92711); anti-FKHRL1 (Upstate Biotechnology, Cat. # 06-951), anti-phospho-T32 FKHRL1 (Upstate Biotechnology, cat. #06-952). Goat anti-rabbit IgG (H+L)-HRP conjugate (BioRad, Cat. # 170-6515) is used as the secondary antibody.

Experimental Protocol (A) Treatment of Cells with Akt1 Inhibitors and Preparation of Cell Lysates:

Target cells (e.g. MDA-MB-468, U87MG, American Type Culture Collection, ATCC) from an exponentially growing culture are plated at $2 \times 10^6$ per 10-cm plate in 10 ml culture media and incubated at 37° C. On the day of treatment, the overnight culture media is replaced with 10 ml of fresh media. Serial dilutions of test compounds are made in 100% DMSO. The volume of each dilution added to the culture should be less than 50 μl so that final DMSO concentration does not exceed 0.5%. An equivalent volume of DMSO is added to the sham-treated control, and a positive control prepared in the same manner is also included. After 30 minutes of treatment, the media is removed. After washing with ice-cold PBS (phosphate-buffered saline), cells are lysed with 100 μl of RIPA buffer (50 mM TRIS pH 7.4, 150 mM NaCl, 1 mM EDTA, 1% NP-40, 0.25% sodium deoxycholate, 1 mM NaF, 1 mM $Na_2VO_4$, and Roche Protease Inhibitor Cocktail tablet, Cat. # 1836170). After removal of the particular fraction, the protein concentration in the cytoplasmic extracts is determined using Pierce BCA assay in microtiter format with BSA as a standard. After adjusting protein concentration, aliquots of the cell lysates are mixed with 4X gel sample buffer (3:1) and stored in −80° C. freezer. (4x gel sample buffer contains 0.25M Tris-HCl, pH 6.8; 40% glycerol; 8% sodium dodecyl sulfate, 0.02% bromophenol blue; and 1.0M 2-mercaptoethanol)

(B) Electrophoresis and Immunoblotting Procedures:

After brief heating at 100° C., equal amounts of cell lysates in gel sample buffer are loaded on 8-16% gradient gels. Electrophoresis is performed by standard procedure. Separated proteins in the gels are transferred to 0.2-micron nitrocellulose membranes using Invitrogen Transfer Buffer (Invitrogen, Cat. #LC3675) adjusted to contain 20% methanol. The blots are blocked with 5% non-fat Carnation milk in TBS/Tween 20 and probed with the primary antibody diluted in 5% milk in TBS/Tween overnight at 4° C. After washings with TBS/Tween, the secondary antibody diluted in 5% milk in TBS/Tween 20 and incubated for 60 min at room temperature. The blots are washed with TBS/Tween and water, and then immersed in Pierce Super Signal West Durra Extended Duration chemiluminescent substrate (Pierce, Cat. # 34075), following vendor's procedure. X-ray films are then exposed to the blots for a short time (10-120 seconds). The intensity of the protein bands of interest is scanned with a Flour-S-MultiImager and quantityOne Software (BioRad).

In Vitro Anti-Proliferation Assay

This following assay measures quantitatively the effect of Akt1 inhibitors on the proliferation and survival of target-relevant human cancer cell lines in culture. The assay employs alamarBlue™ dye as an indicator of viable cells. The model cell lines chosen are those with elevated phospho-Akt activity that arises as a result of defects in the tumor suppressor, PTEN.

Cell Lines:

(a) Cancer cell lines with elevated phospho-Akt as a result of loss of PTEN activity. They include but are not limited to the following: breast cancer: MDA-MB468, MDA-MB-436, HCT1937, and BT549 (PTEN−/−); prostate cancer: PC3, LNCaP and its derivatives, LN T1.16, LN T2.9 (PTEN−/−); glioblastoma: U87MG, DBTRG005MG (PTEN−/−). (b) Cancer cell lines with elevated phospho-Akt as a result of reduced PTEN activity: They include but are not limit to the following: Ovarian cancer: A2780 (PTEN+/−) and (c) Cancer cell lines with deregulated PI3-kinase activity: They include but are not limited to the following: ovarian cancer: OVCAR3, SKOV3.

For the anti-proliferation studies with Akt1 inhibitors, MDA-MB468 and U87MG are used routinely. The results from studies with both cell lines are usually in good accord. A2780, LNCaP and PC3 have also been used in studies with select sets of Akt inhibitors and shown to respond similarly as MDA-MB468 and U87MG. Other cancer cell lines having features of (a), (b) and/or (c) above may also be used.

Procedure for alamarBlue™ Cell Proliferation Assay

Target cells (e.g. MDA-MB-468, U87MG) from an exponentially growing culture are plated at 5-10,000 cells/100 μl per well in a 96-well cell culture plate and incubated overnight at 37° C. in a $CO_2$ incubator. On the day of treatment, 100 μl of serially diluted test compounds are added to the cells in triplicate, with a final DMSO concentration not exceeding 0.5%. Samples containing DMSO only and a positive control prepared in a similar manner are included as controls. Cells are incubated in a $CO_2$ incubator at 37° C. for 72 hours. To measure viable cells quantitatively, 20 μl of alamarBlue™ (Trek Diagnostic Systems, Inc., cat. # 00-100) per well is added to the cells, and the incubation continues for 4-5 hours. (Other indicators for viable cells may also be used.) Fluorescence is measured with excitation wavelength at 595 nm in SpectraFluor Plus (TeCan Instruments).

What is claimed is:

1. A compound of the formula (I):

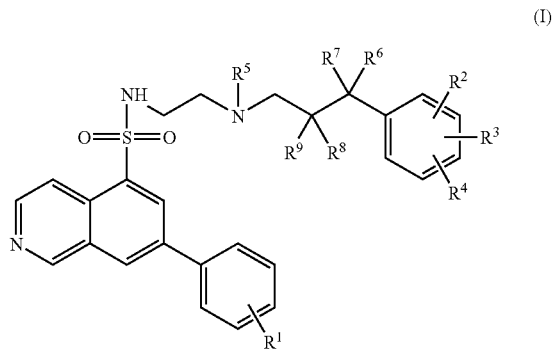

wherein $R^1$ is hydrogen, halogen, hydroxy, amino, —$CHF_2$, —$CF_3$, or —$NHSO_2CH_3$;

$R^2$, $R^3$, and $R^4$ are each independently selected from the group consisting of:

hydrogen;

halogen;

—($C_1$-$C_4$)alkyl;

—$CF_3$;

amino;

nitro;

—$(CH_2)_pOR^{10}$;

—$(CH_2)_nCN$;

—$C(O)NR^{11}R^{12}$;

—$C(O)OR^{16}$;

—$NHC(O)R^{13}$;

—$O(CH_2)_oY$;

—$SCH_3$;

—$SO_2R^{14}$;

N-morpholino;

N-piperazine or N-piperazine substituted with ($C_1$-$C_4$) alkyl;

N-pyrrolidine or N-pyrrolidine substituted with —(CH$_2$)$_p$OH;

N-1,1-dioxothiomorpholine;

N-[1,4]-diazepinyl;

phenyl or phenyl substituted with —CF$_3$, nitro, amino, halogen, hydroxy, (C$_1$-C$_4$) alkyl, (C$_1$-C$_4$)alkoxy or —NHSO$_2$CH$_3$; and piperidine or piperidine substituted on the nitrogen with —C(O)(C$_1$-C$_4$) alkyl;

or R$^2$ and R$^3$ may, together with the phenyl ring to which they are attached, form a naphthaline (benzo-fused ring) of the structure:

R$^5$, R$^6$ and R$^8$ are hydrogen;

R$^7$ and R$^9$ are each independently hydrogen or hydroxy;

R$^{10}$ is hydrogen, (C$_1$-C$_4$)alkyl, —(CF$_2$)$_t$CHF$_2$, —(CH$_2$)$_q$NR$^{17}$R$^{18}$, —(CH$_2$)$_q$O(C$_1$-C$_4$ alkyl), pyrrolidine, or phenyl;

which pyrrolidine may be optionally substituted on the nitrogen with C$_1$-C$_4$ alkyl R$^{11}$ and R$^{12}$ are each independently hydrogen or (C$_1$-C$_4$) alkyl;

R$^{13}$ is (C$_1$-C$_4$)alkyl, cyclopropyl or —(CH$_2$)—OR$^{19}$;

R$^{14}$ is (C$_1$-C$_4$)alkyl, —NR$^{20}$R$^{21}$, N-pyrrolidine, phenyl, or -CF$_3$;

R$^{16}$, R$^{17}$, R$^{18}$, R$^{19}$, R$^{20}$, and R$^{21}$ are each independently hydrogen or C$_1$-C$_4$ alkyl;

m is 0, 1, 2, or 3;

n is 0 or 1;

o is 1, 2 or 3;

p is 0, 1 or 2;

q is 1, 2, or 3;

t is 0 or 1;

Y is morpholine, pyrrolidine, or pyrrolidine substituted on the nitrogen by (C$_1$-C$_4$)alkyl;

or a pharmaceutically acceptable salt thereof.

2. The compound according to claim 1, wherein

R$^2$ is hydrogen, C$_1$-C$_4$ alkyl, or phenyl;

R$^3$ is hydrogen or hydroxy;

R$^4$ is hydrogen, halogen, nitro, cyano, —CF$_3$, —(CH$_2$)$_p$OR$^{10}$, or —SO$_2$R$^{14}$;

p is 0;

R$^{10}$ is —CHF$_2$;

R$^{14}$ is (C$_1$-C$_4$)alkyl; —CF$_3$; or —NR$^{20}$R$^{21}$, or a pharmaceutically acceptable salt thereof.

3. The compound according to claim 2 wherein R$^4$ is nitro;

or a pharmaceutically acceptable salt thereof.

4. The compound according to claim 3 wherein R$^2$ and R$^3$ are hydrogen.

5. The compound according to claim 2 wherein R$^2$ is hydrogen;

R$^3$ is hydroxy; and R$^4$ is hydrogen;

or a pharmaceutically acceptable salt thereof.

6. The compound according to claim 1, which is selected from the group consisting of:

7-Phenyl-isoquinoline-5-sulfonic acid {2-[3-(4-nitrophenyl)-propylamino]-ethyl}-amide, dihydrochloride salt;

7-Phenyl-isoquinoline-5-sulfonic acid {2-[3-(4-cyanophenyl)-propylamino]-ethyl}-amide, dihydrochloride salt;

7-Phenyl-isoquinoline-5-sulfonic acid {2-[3-(2-methyl-4-nitrophenyl)-propylamino]-ethyl}-amide, dihydrochloride salt;

(S)-7-Phenyl-isoquinoline-5-sulfonic acid [2-(3-hydroxy-3-(4-nitrophenyl)-propylamino)-ethyl]-amide, mesylate salt;

7-Phenyl-isoquinoline-5-sulfonic acid [2-(2,3-dihydroxy-3-(4-nitrophenyl)-propylamino)-ethyl]-amide isomer 1, dihydrochloride salt; and 7-Phenyl-isoquinoline-5-sulfonic acid [2-(2,3-dihydroxy-3-(4-nitrophenyl)-propylamino)-ethyl]-amide isomer 2, dihydrochloride salt.

7. A compound of the formula:

wherein R$^1$ is hydrogen, halogen, hydroxy, amino, —CHF$_2$ or —NHSO$_2$CH$_3$;

R$^2$, R$^3$, and R$^4$ are each independently:

hydrogen;

halogen;

—(C1-C4)alkyl;

—CF$_3$;

amino;

nitro;

—(CH$_2$)$_p$OR$^{10}$;

—(CH$_2$)$_n$CN;

—C(O)NR$^{11}$R$^{12}$;

—C(O)OR$^{11}$;

—NHC(O)R$^{13}$;

—O(CH$_2$)$_o$Y;

—SCH$_3$;

—SO$_2$R$^{14}$;

N-morpholino;

N-piperazine or N-piperazine substituted with (C1-C4) alkyl;

N-pyrrolidine or N-pyrrolidine substituted with —(CH$_2$)$_p$OH;

N-1,1-dioxothiomorpholine;

N-[1,4]-diazepinyl;

phenyl or phenyl substituted with —CF$_3$, nitro, amino, halogen, hydroxy, (C1-C4) alkyl, (C1-C4)alkoxy or —NHSO$_2$CH$_3$;

piperidine or piperidine substituted on the nitrogen with —C(O)(C1-C4) alkyl;

or wherein $R^2$ and $R^3$ may together with the phenyl ring of formula I form a naphthaline (benzo-fused ring) of the structure:

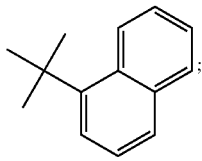

$R^5$, $R^6$ and $R^8$ are hydrogen;
$R^7$ and $R^9$ are each independently hydrogen or hydroxy;
$R^{10}$ is hydrogen, (C1-C4)alkyl, $-(CF_2)_n CHF_2$, $-(CH_2)_m NR^{11}R^{12}$, $-(CH_2)_o O(C1-C4alkyl)$, or phenyl;
$R^{11}$ and $R^{12}$ are each independently hydrogen or (C1-C4) alkyl;
$R^{13}$ is (C1-C4)alkyl, cyclopropyl or $-(CH_2)_o R^{11}$;
$R^{14}$ is (C1-C4)alkyl, $-NR^{11}R^{12}$, N-pyrrolidine, phenyl, or $-CF_3$;
m is 0, 1, 2, or 3;
n is 0 or 1;
o is 1, 2 or 3;
p is 0, 1 or 2;
Y is morpholine, pyrrolidine or pyrrolidine substituted on the nitrogen by (C1-C4)alkyl;
or a pharmaceutically acceptable salt thereof.

8. A compound selected from the group consisting of:
7-phenyl-isoquinoline-5-sulfonic acid (2-amino-ethyl)-amide;
7-(3-difluoromethylphenyl)-isoquinoline-5-sulfonic acid (2-amino-ethyl)-amide;
7-(4-aminophenyl)-isoquinoline-5-sulfonic acid (2-amino-ethyl)-amide;
7-(3-aminophenyl)-isoquinoline-5-sulfonic acid (2-amino-ethyl)-amide;
7-(3-fluorophenyl)-isoquinoline-5-sulfonic acid (2-amino-ethyl)-amide;
7-(4-methylsulfonamido)- isoquinoline-5-sulfonic acid (2-amino-ethyl)-amide;
7-(3-hydroxyphenyl)-isoquinoline-5-sulfonic acid (2-amino-ethyl)-amide;
7-(4-hydroxyphenyl)-isoquinoline-5-sulfonic acid (2-amino-ethyl)-amide;
7-(4-hydroxy-phenyl)-isoquinoline-5-sulfonic acid {2-[3-(4-nitro-phenyl)-propylamino]-ethyl}-amide, dihydrochloride salt; and
7-phenyl-isoquinoline-5-sulfonic acid {2-[3-(4-nitro-phenyl)-propylamino]-ethyl}-amide, dimesylate.

9. A pharmaceutical composition comprising a compound of claim 1, or a pharmaceutically acceptable salt thereof, in combination with a pharmaceutically acceptable carrier, excipient, or diluent.

* * * * *